(12) United States Patent
Voss et al.

(10) Patent No.: US 11,690,979 B2
(45) Date of Patent: Jul. 4, 2023

(54) EXPANDABLE INTRODUCER SHEATH TO PRESERVE GUIDEWIRE ACCESS

(71) Applicant: Abbott Laboratories, Abbott Park, IL (US)

(72) Inventors: Laveille Kao Voss, Belmont, CA (US); Kelly J. McCrystle, Menlo Park, CA (US); Arkady Kokish, Los Gatos, CA (US)

(73) Assignee: Abbott Laboratories, Abbott Park, IL (US)

( * ) Notice: Subject to any disclaimer, the term of this patent is extended or adjusted under 35 U.S.C. 154(b) by 288 days.

(21) Appl. No.: 16/951,289

(22) Filed: Nov. 18, 2020

(65) Prior Publication Data

US 2021/0069475 A1 Mar. 11, 2021

Related U.S. Application Data

(63) Continuation of application No. 15/861,970, filed on Jan. 4, 2018, which is a continuation of application
(Continued)

(51) Int. Cl.
*A61M 25/04* (2006.01)
*A61B 17/00* (2006.01)
(Continued)

(52) U.S. Cl.
CPC .......... *A61M 25/04* (2013.01); *A61B 17/0057* (2013.01); *A61B 17/0644* (2013.01);
(Continued)

(58) Field of Classification Search
CPC .......... A61M 25/0023; A61M 25/0032; A61M 2025/0035; A61M 25/0054;
(Continued)

(56) References Cited

U.S. PATENT DOCUMENTS

| 883,583 A | 3/1908 | Stallsmith |
| 1,696,018 A | 12/1928 | Schellberg |

(Continued)

FOREIGN PATENT DOCUMENTS

| EP | 0450221 A1 | 10/1991 |
| EP | 2548603 A1 | 1/2013 |

(Continued)

OTHER PUBLICATIONS

Office Action received for U.S. Appl. No. 12/696,837, dated Jan. 13, 2015.
(Continued)

*Primary Examiner* — Scott J Medway
(74) *Attorney, Agent, or Firm* — Workman Nydegger; Randy Shen

(57) ABSTRACT

An introducer sheath is described. The introducer sheath may include a tubular body. The tubular body may extend from a distal end toward a proximal end. The tubular body may include a lumen. The lumen may at least partially be defined by a wall. A channel may be disposed within the wall. The channel may be configured to receive a guidewire. The tubular body may include an expandable portion expandable to increase a cross-sectional area of the lumen.

14 Claims, 41 Drawing Sheets

Related U.S. Application Data

No. 13/835,570, filed on Mar. 15, 2013, now Pat. No. 9,889,275, which is a continuation-in-part of application No. 12/696,792, filed on Jan. 29, 2010, now Pat. No. 9,597,063, which is a continuation-in-part of application No. 11/767,947, filed on Jun. 25, 2007, now Pat. No. 8,801,744, which is a continuation-in-part of application No. 11/427,308, filed on Jun. 28, 2006, now abandoned, said application No. 13/835,570 is a continuation-in-part of application No. 11/767,947, filed on Jun. 25, 2007, now Pat. No. 8,801,744, which is a continuation-in-part of application No. 11/427,308, filed on Jun. 28, 2006, now abandoned, said application No. 13/835,570 is a continuation-in-part of application No. 12/696,837, filed on Jan. 29, 2010, now abandoned, which is a continuation-in-part of application No. 11/427,308, filed on Jun. 28, 2006, now abandoned, said application No. 13/835,570 is a continuation-in-part of application No. 11/427,308, filed on Jun. 28, 2006, now abandoned.

(51) Int. Cl.
  *A61B 17/34* (2006.01)
  *A61M 25/00* (2006.01)
  *A61M 25/06* (2006.01)
  *A61B 17/064* (2006.01)
  *A61B 90/00* (2016.01)
  *A61B 17/22* (2006.01)
  *A61B 17/068* (2006.01)

(52) U.S. Cl.
  CPC ..... *A61B 17/3439* (2013.01); *A61M 25/0017* (2013.01); *A61M 25/0662* (2013.01); *A61B 17/068* (2013.01); *A61B 2017/00668* (2013.01); *A61B 2017/0645* (2013.01); *A61B 2017/22039* (2013.01); *A61B 2017/3445* (2013.01); *A61B 2090/037* (2016.02); *A61M 2025/0024* (2013.01); *A61M 2025/0035* (2013.01)

(58) Field of Classification Search
  CPC .. A61M 2025/0025; A61M 2025/0036; A61M 2025/0037
  See application file for complete search history.

(56) References Cited

U.S. PATENT DOCUMENTS

| | | |
|---|---|---|
| 2,548,602 A | 4/1951 | Greenburg |
| 3,633,586 A | 1/1972 | Sheridan |
| 4,143,853 A | 3/1979 | Abramson |
| 4,406,656 A | 9/1983 | Hattler et al. |
| 4,411,655 A | 10/1983 | Schreck |
| 4,451,256 A | 5/1984 | Weikl et al. |
| 4,574,173 A | 3/1986 | Bennett |
| 4,596,559 A | 6/1986 | Fleischhacker |
| 4,601,713 A | 7/1986 | Fuqua |
| 4,619,643 A | 10/1986 | Bai |
| 4,747,833 A | 5/1988 | Kousai et al. |
| 4,748,982 A | 6/1988 | Horzewski et al. |
| 4,771,777 A | 9/1988 | Horzewski et al. |
| 4,883,468 A | 11/1989 | Kousai et al. |
| 4,899,729 A | 2/1990 | Gill et al. |
| 4,929,235 A | 5/1990 | Merry et al. |
| 4,940,064 A | 7/1990 | Desai |
| 4,950,257 A | 8/1990 | Hibbs et al. |
| 4,983,168 A | 1/1991 | Moorehead |
| 5,061,273 A | 10/1991 | Yock |
| 5,106,054 A | 4/1992 | Mollenauer et al. |
| 5,106,368 A | 4/1992 | Uldall et al. |
| 5,154,725 A | 10/1992 | Leopold |
| 5,176,652 A | 1/1993 | Littrell |
| 5,176,659 A | 1/1993 | Mancini |
| 5,180,372 A | 1/1993 | Vegoe et al. |
| 5,195,978 A | 3/1993 | Schiffer |
| 5,203,338 A | 4/1993 | Jang |
| RE34,327 E | 7/1993 | Kreamer et al. |
| 5,244,619 A | 9/1993 | Burnham |
| 5,250,033 A | 10/1993 | Evans et al. |
| 5,320,611 A | 6/1994 | Bonutti et al. |
| 5,324,269 A | 6/1994 | Miraki |
| 5,326,350 A | 7/1994 | Li |
| 5,354,280 A | 10/1994 | Haber et al. |
| 5,415,639 A | 5/1995 | Vandeneinde et al. |
| 5,423,774 A | 6/1995 | Fischell et al. |
| 5,447,503 A | 9/1995 | Miller |
| 5,464,398 A | 11/1995 | Haindl |
| 5,466,230 A | 11/1995 | Davila |
| 5,472,418 A | 12/1995 | Palestrant |
| 5,556,390 A | 9/1996 | Hicks |
| 5,558,737 A | 9/1996 | Brown et al. |
| 5,584,803 A | 12/1996 | Stevens et al. |
| 5,624,395 A | 4/1997 | Mikhail et al. |
| 5,647,846 A | 7/1997 | Berg et al. |
| 5,658,262 A | 8/1997 | Castaneda et al. |
| 5,674,240 A | 10/1997 | Bonutti et al. |
| 5,681,296 A | 10/1997 | Ishida |
| 5,693,025 A | 12/1997 | Stevens |
| 5,749,889 A | 5/1998 | Bacich et al. |
| 5,795,326 A | 8/1998 | Siman |
| 5,807,311 A | 9/1998 | Palestrant |
| 5,810,776 A | 9/1998 | Bacich et al. |
| 5,823,961 A | 10/1998 | Fields et al. |
| 5,827,227 A | 10/1998 | Delago |
| 5,868,717 A | 2/1999 | Prosl |
| 5,910,155 A | 6/1999 | Ratcliff et al. |
| 5,916,178 A | 6/1999 | Noone et al. |
| 5,944,691 A | 8/1999 | Querns et al. |
| 5,957,902 A | 9/1999 | Teves |
| 5,964,730 A | 10/1999 | Williams et al. |
| 5,968,009 A | 10/1999 | Siman |
| 5,993,436 A | 11/1999 | Kitou et al. |
| 6,007,522 A | 12/1999 | Agro et al. |
| 6,056,722 A | 5/2000 | Jayaraman |
| 6,183,443 B1 | 2/2001 | Kratoska et al. |
| 6,190,357 B1 | 2/2001 | Ferrari et al. |
| 6,192,568 B1 | 2/2001 | Kafrawy et al. |
| 6,210,312 B1 | 4/2001 | Nagy |
| 6,224,586 B1 | 5/2001 | Stephens |
| 6,280,433 B1 | 8/2001 | McIvor et al. |
| 6,312,374 B1 | 11/2001 | Von Hoffmann |
| 6,350,274 B1 | 2/2002 | Li |
| 6,358,266 B1 | 3/2002 | Bonutti |
| 6,416,499 B2 | 7/2002 | Paul, Jr. |
| 6,419,624 B1 | 7/2002 | Burton et al. |
| 6,450,987 B1 | 9/2002 | Kramer |
| 6,497,721 B2 | 12/2002 | Ginsburg et al. |
| 6,562,049 B1 | 5/2003 | Norlander et al. |
| 6,616,678 B2 | 9/2003 | Nishtala et al. |
| 6,630,086 B1 | 10/2003 | Goral et al. |
| 6,663,821 B2 | 12/2003 | Seward |
| 6,712,791 B2 | 3/2004 | Lui et al. |
| 6,749,600 B1 | 6/2004 | Levy |
| 6,796,976 B1 | 9/2004 | Chin et al. |
| 6,821,285 B2 | 11/2004 | Laufer et al. |
| 6,827,710 B1 | 12/2004 | Mooney et al. |
| 6,849,062 B2 | 2/2005 | Kantor |
| 6,887,417 B1 | 5/2005 | Gawreluk et al. |
| 6,923,788 B2 | 8/2005 | Kantor |
| 6,945,990 B2 | 9/2005 | Greenan |
| 7,144,386 B2 | 12/2006 | Korkor et al. |
| 7,208,001 B2 | 4/2007 | Coyle et al. |
| 7,273,486 B2 | 9/2007 | Coyle et al. |
| 7,276,045 B2 | 10/2007 | Duffy |
| 7,637,893 B2 | 12/2009 | Christensen et al. |
| 7,699,864 B2 | 4/2010 | Kick et al. |
| 7,713,193 B2 | 5/2010 | Nance et al. |
| 7,727,179 B2 | 6/2010 | Barrett |

(56) References Cited

U.S. PATENT DOCUMENTS

| | | |
|---|---|---|
| 7,762,995 B2 | 7/2010 | Eversull et al. |
| 7,803,107 B2 | 9/2010 | Carrillo |
| 7,879,021 B2 | 2/2011 | Drewes, Jr. |
| 7,896,897 B2 | 3/2011 | Gresham et al. |
| 7,912,531 B1 | 3/2011 | Chiu et al. |
| 7,967,830 B2 | 6/2011 | Ayala et al. |
| 7,974,710 B2 | 7/2011 | Seifert |
| 8,012,127 B2 | 9/2011 | Lieberman et al. |
| 8,088,143 B2 | 1/2012 | Aakerfeldt |
| 8,216,294 B2 | 7/2012 | Johnson et al. |
| 8,231,519 B2 | 7/2012 | Reichenbach et al. |
| 8,359,723 B2 | 1/2013 | Voss |
| 8,440,122 B2 | 5/2013 | Voss |
| 8,758,402 B2 | 6/2014 | Jenson et al. |
| 8,801,744 B2 | 8/2014 | Mccrystle et al. |
| 8,894,615 B2 | 11/2014 | Voss |
| 8,932,324 B2 | 1/2015 | Sibbitt et al. |
| 9,089,311 B2 | 7/2015 | Fortson et al. |
| 9,168,060 B2 | 10/2015 | Voss |
| 9,168,359 B2 | 10/2015 | Rowe et al. |
| 9,345,460 B2 | 5/2016 | Houser et al. |
| 9,352,118 B2 | 5/2016 | Rowe et al. |
| 9,597,063 B2 | 3/2017 | Voss et al. |
| 9,687,621 B2 | 6/2017 | Hoftman et al. |
| 9,889,275 B2 | 2/2018 | Voss et al. |
| 10,413,703 B2 | 9/2019 | Klocke et al. |
| 2001/0041872 A1 | 11/2001 | Paul |
| 2001/0049499 A1 | 12/2001 | Lui et al. |
| 2002/0010425 A1 | 1/2002 | Guo et al. |
| 2002/0032459 A1 | 3/2002 | Horzewski et al. |
| 2002/0072768 A1 | 6/2002 | Ginn |
| 2002/0107482 A1 | 8/2002 | Rocamora et al. |
| 2002/0183781 A1 | 12/2002 | Casey et al. |
| 2003/0004537 A1 | 1/2003 | Boyle et al. |
| 2003/0014015 A1 | 1/2003 | Tansey et al. |
| 2003/0032941 A1 | 2/2003 | Boyle et al. |
| 2003/0050604 A1* | 3/2003 | Lui .................. A61M 39/0606 604/164.05 |
| 2003/0158578 A1 | 8/2003 | Pantages et al. |
| 2003/0220667 A1 | 11/2003 | Van et al. |
| 2004/0102738 A1 | 5/2004 | Dikeman et al. |
| 2004/0116957 A1 | 6/2004 | Nishide et al. |
| 2004/0153122 A1 | 8/2004 | Palermo |
| 2004/0162578 A1 | 8/2004 | Redmond et al. |
| 2005/0027257 A1 | 2/2005 | Davey |
| 2005/0059934 A1 | 3/2005 | Wenchell et al. |
| 2005/0059990 A1 | 3/2005 | Ayala et al. |
| 2005/0065498 A1 | 3/2005 | McFerran |
| 2005/0080430 A1 | 4/2005 | Wright et al. |
| 2005/0085841 A1 | 4/2005 | Eversull et al. |
| 2005/0085842 A1 | 4/2005 | Eversull et al. |
| 2005/0131447 A1 | 6/2005 | Wahr et al. |
| 2005/0149105 A1 | 7/2005 | Leeflang et al. |
| 2005/0165439 A1 | 7/2005 | Weber et al. |
| 2005/0261663 A1 | 11/2005 | Patterson et al. |
| 2006/0287674 A1 | 12/2006 | Ginn et al. |
| 2007/0005001 A1 | 1/2007 | Rowe et al. |
| 2007/0049946 A1 | 3/2007 | Mackley et al. |
| 2007/0088322 A1 | 4/2007 | Dicarlo et al. |
| 2007/0224309 A1 | 9/2007 | Mejlhede et al. |
| 2008/0004569 A1 | 1/2008 | McCrystle et al. |
| 2008/0004571 A1 | 1/2008 | Voss |
| 2008/0051717 A1 | 2/2008 | Voss et al. |
| 2008/0097350 A1 | 4/2008 | Bell et al. |
| 2008/0215089 A1 | 9/2008 | Williams et al. |
| 2008/0312686 A1 | 12/2008 | Ellingwood |
| 2009/0054874 A1 | 2/2009 | Barron et al. |
| 2009/0171318 A1 | 7/2009 | Drewes, Jr. |
| 2009/0204052 A1 | 8/2009 | Nimkar et al. |
| 2009/0221965 A1 | 9/2009 | Osypka |
| 2009/0264832 A1 | 10/2009 | Dikeman et al. |
| 2009/0270989 A1 | 10/2009 | Conner et al. |
| 2010/0094392 A1 | 4/2010 | Nguyen et al. |
| 2010/0130936 A1 | 5/2010 | Voss |
| 2010/0130937 A1 | 5/2010 | Voss |
| 2010/0130939 A1 | 5/2010 | Voss |
| 2010/0198159 A1 | 8/2010 | Voss et al. |
| 2010/0198160 A1 | 8/2010 | Voss |
| 2010/0268163 A1 | 10/2010 | Rowe et al. |
| 2012/0041419 A1 | 2/2012 | Blanchard et al. |
| 2012/0109159 A1 | 5/2012 | Jordan et al. |
| 2012/0209221 A1 | 8/2012 | Patterson et al. |
| 2013/0085479 A1 | 4/2013 | De et al. |
| 2013/0138043 A1 | 5/2013 | Voss |
| 2013/0211324 A1 | 8/2013 | Voss et al. |
| 2013/0338595 A1 | 12/2013 | Voss |
| 2015/0088072 A1 | 3/2015 | Voss |
| 2016/0022252 A1 | 1/2016 | Zhang et al. |
| 2016/0271364 A1 | 9/2016 | Rowe et al. |
| 2018/0140801 A1 | 5/2018 | Voss et al. |

FOREIGN PATENT DOCUMENTS

| | | |
|---|---|---|
| JP | 03-289967 A | 12/1991 |
| JP | 2009-279044 A | 12/2009 |
| RU | 2117191 C1 | 8/1998 |
| WO | 98/13083 A1 | 4/1998 |
| WO | 98/29026 A2 | 7/1998 |
| WO | 2004/037333 A1 | 5/2004 |
| WO | 2005/018728 A2 | 3/2005 |
| WO | 2005/099802 A2 | 10/2005 |
| WO | 2007/005584 A1 | 1/2007 |
| WO | 2008/002915 A2 | 1/2008 |
| WO | 2009/120871 A2 | 10/2009 |

OTHER PUBLICATIONS

Office Action received for U.S. Appl. No. 12/696,837, dated Jul. 19, 2012.

Office Action received for U.S. Appl. No. 12/724,889, dated Mar. 21, 2014.

Office Action received for U.S. Appl. No. 12/724,889, dated Mar. 29, 2012.

Office Action received for U.S. Appl. No. 12/724,889, dated Oct. 10, 2014.

Office Action received for U.S. Appl. No. 12/724,889, dated Oct. 26, 2012.

Office Action received for U.S. Appl. No. 13/835,570, dated Apr. 22, 2016.

Office Action received for U.S. Appl. No. 13/835,570, dated Feb. 21, 2017.

Office Action received for U.S. Appl. No. 13/835,570, dated Jul. 28, 2014.

Office Action received for U.S. Appl. No. 13/835,570, dated Mar. 19, 2015.

Office Action received for U.S. Appl. No. 13/835,570, dated Oct. 22, 2015.

Office Action received for U.S. Appl. No. 13/835,570, dated Oct. 27, 2016.

Office Action received for U.S. Appl. No. 13/892,106, dated Apr. 30, 2015.

Office Action received for U.S. Appl. No. 13/892,106, dated Aug. 12, 2014.

Office Action received for U.S. Appl. No. 13/892,106, dated Mar. 26, 2014.

Office Action received for U.S. Appl. No. 13/892,106, dated Nov. 28, 2014.

Office Action received for U.S. Appl. No. 14/551,374, dated Mar. 21, 2017.

Office Action received for U.S. Appl. No. 14/551,374, dated May 6, 2016.

Office Action received for U.S. Appl. No. 14/551,374, dated Nov. 3, 2016.

Office Action received for U.S. Appl. No. 14/551,374, dated Oct. 16, 2017.

Office Action received for U.S. Appl. No. 15/166,473, dated May 31, 2017.

Office Action received for U.S. Appl. No. 15/166,473, dated Nov. 17, 2016.

(56) References Cited

OTHER PUBLICATIONS

Office Action recived for U.S. Appl. No. 12/696,792, dated Dec. 27, 2013.
Office Action recived for U.S. Appl. No. 13/752,137, dated Mar. 10, 2014.
Office Action recived for U.S. Appl. No. 13/892,106, dated Mar. 26, 2014.
Restriction Requirement received for U.S. Appl. No. 12/695,961, dated Feb. 13, 2012.
Restriction Requirement received for U.S. Appl. No. 12/695,975, dated Feb. 13, 2012.
Richard Vennix, Material Properties of PTFE, Engineering Polymers | Polymers Data Sheets, Matbase <<http://www.matbase.com/material/polymers/engineering/ptfe/properties>> Jan. 25, 2010.
U.S. Appl. filed Jan. 28, 2010, Voss., U.S. Appl. No. 12/695,975, U.S. Appl. No. 12/695,975.
U.S. Appl. filed Jan. 28, 2013, Voss., U.S. Appl. No. 13/752,137, U.S. Appl. No. 13/752,137.
U.S. Appl. filed Jan. 29, 2010, Voss., U.S. Appl. No. 12/696,792, U.S. Appl. No. 12/696,792.
U.S. Appl. filed Jan. 29, 2010, Voss., U.S. Appl. No. 12/696,837, U.S. Appl. No. 12/696,837.
U.S. Appl. filed Mar. 15, 2013, Voss et al., U.S. Appl. No. 13/835,570, U.S. Appl. No. 13/835,570.
U.S. Appl. filed Mar. 16, 2010, Rowe et al., U.S. Appl. No. 12/724,889, U.S. Appl. No. 12/724,889.
U.S. Appl. No. 12/695,969, filed Jan. 28, 2010, Voss., U.S. Appl. No. 12/695,969.
U.S. Appl. No. 60/695,464, filed Jun. 30, 2005, Rowe., U.S. Appl. No. 60/695,464.
U.S. Patent Application filed Jan. 29, 2010, by Voss, U.S. Appl. No. 12/696,792, U.S. Appl. No. 12/696,792.
U.S. Patent Application filed Mar. 15, 2013 by Voss et al., U.S. Appl. No. 13/835,570, U.S. Appl. No. 13/835,570.
U.S. Patent Application filed Mar. 16, 2010 by Rowe et al., U.S. Appl. No. 12/724,889, U.S. Appl. No. 12/724,889.
U.S. Patent Application filed Nov. 24, 2014, Voss, U.S. Appl. No. 14/551,374, U.S. Appl. No. 14/551,374.
U.S. Provisional Application filed Jun. 30, 2005, by Rowe, U.S. Appl. No. 60/695,464, U.S. Appl. No. 60/695,464.
U.S. Provisional Application filed Jun. 30, 2005, by Voss., U.S. Appl. No. 60/695,602, U.S. Appl. No. 60/695,602.
U.S. Provisional Application filed Jun. 30, 2005, by Rowe et al., U.S. Appl. No. 60/695,602, U.S. Appl. No. 60/695,602.
Notice of Allowance received for U.S. Appl. No. 12/695,961, dated Sep. 20, 2012.
Notice of Allowance received for U.S. Appl. No. 12/724,889, dated Sep. 14, 2015.
Notice of Allowance received for U.S. Appl. No. 13/835,570, dated Sep. 26, 2017.
Notice of Allowance received for U.S. Appl. No. 13/892,106, dated Jul. 15, 2015.
Office Action received for U.S. Appl. No. 11/427,301, dated Mar. 11, 2013.
Office Action received for U.S. Appl. No. 11/427,301, dated Oct. 27, 2010.
Office Action received for U.S. Appl. No. 11/427,306, dated Apr. 12, 2010.
Office Action received for U.S. Appl. No. 11/427,306, dated Aug. 21, 2009.
Office Action received for U.S. Appl. No. 11/427,306, dated Feb. 26, 2008.
Office Action received for U.S. Appl. No. 11/427,306, dated Mar. 5, 2009.
Office Action received for U.S. Appl. No. 11/427,306, dated Oct. 21, 2010.
Office Action received for U.S. Appl. No. 11/427,308, dated Apr. 23, 2014.
Office Action received for U.S. Appl. No. 11/427,308, dated Jul. 19, 2012.
Office Action received for U.S. Appl. No. 11/427,308, dated Mar. 29, 2011.
Office Action received for U.S. Appl. No. 11/427,308, dated May 11, 2010.
Office Action received for U.S. Appl. No. 11/427,308, dated Oct. 25, 2011.
Office Action received for U.S. Appl. No. 11/427,308, dated Sep. 15, 2010.
Office Action received for U.S. Appl. No. 11/427,308, dated Sep. 29, 2009.
Office Action received for U.S. Appl. No. 11/767,947, dated Aug. 20, 2010.
Office Action received for U.S. Appl. No. 11/767,947, dated Feb. 3, 2011.
Office Action received for U.S. Appl. No. 11/767,947, dated Feb. 27, 2012.
Office Action received for U.S. Appl. No. 11/767,947, dated Jul. 8, 2011.
Office Action received for U.S. Appl. No. 11/767,947, dated Mar. 31, 2010.
Office Action received for U.S. Appl. No. 12/695,961, dated May 11, 2012.
Office Action received for U.S. Appl. No. 12/695,969, dated Jan. 24, 2012.
Office Action received for U.S. Appl. No. 12/695,969, dated Jul. 20, 2012.
Office Action received for U.S. Appl. No. 12/695,975, dated Feb. 25, 2014.
Office Action received for U.S. Appl. No. 12/695,975, dated Jul. 14, 2014.
Office Action received for U.S. Appl. No. 12/695,975, dated May 11, 2012.
Office Action received for U.S. Appl. No. 12/695,975, dated Oct. 5, 2012.
Office Action received for U.S. Appl. No. 12/696,792, dated Jan. 20, 2016.
Office Action received for U.S. Appl. No. 12/696,792, dated Jan. 29, 2015.
Office Action received for U.S. Appl. No. 12/696,792, dated Jul. 21, 2016.
Office Action received for U.S. Appl. No. 12/696,792, dated Jul. 28, 2015.
Office Action received for U.S. Appl. No. 12/696,837, dated Apr. 25, 2014.
Loginov, Nail—Machine Translation, Aug. 10, 1998, FreePatents <<http://www.freepatent.ru/patents/2117191>>. Accessed Mar. 10, 2017.
Notice of Allowance received for U.S. Appl. No. 11/427,301, dated May 19, 2015.
Notice of Allowance received for U.S. Appl. No. 12/695,969, dated Dec. 24, 2012.
Notice of Allowance received for U.S. Appl. No. 12/696,792, dated Nov. 10, 2016.
Notice of Allowance received for U.S. Appl. No. 13/752,137, dated Jun. 23, 2014.
Notice of Allowance recived for U.S. Appl. No. 11/767,947, dated Nov. 27, 2013.
Office Action received for U.S. Appl. No. 11/427,301, dated Apr. 27, 2010.
Office Action received for U.S. Appl. No. 11/427,301, dated Jun. 8, 2012.
Office Action received for U.S. Appl. No. 11/767,947, dated Jun. 2, 2009.
Office Action received for U.S. Appl. No. 11/767,947, dated Nov. 12, 2009.
Office Action received for U.S. Appl. No. 12/695,961 dated Feb. 13, 2012.
Office Action received for U.S. Appl. No. 12/695,975, dated Dec. 16, 2014.
Office Action received for U.S. Appl. No. 12/695,975, dated Feb. 13, 2012.
Office Action received for U.S. Appl. No. 12/696,792, dated Nov. 10, 2011.

(56) References Cited

OTHER PUBLICATIONS

Office Action received for U.S. Appl. No. 12/696,837, dated Dec. 19, 2011.

* cited by examiner

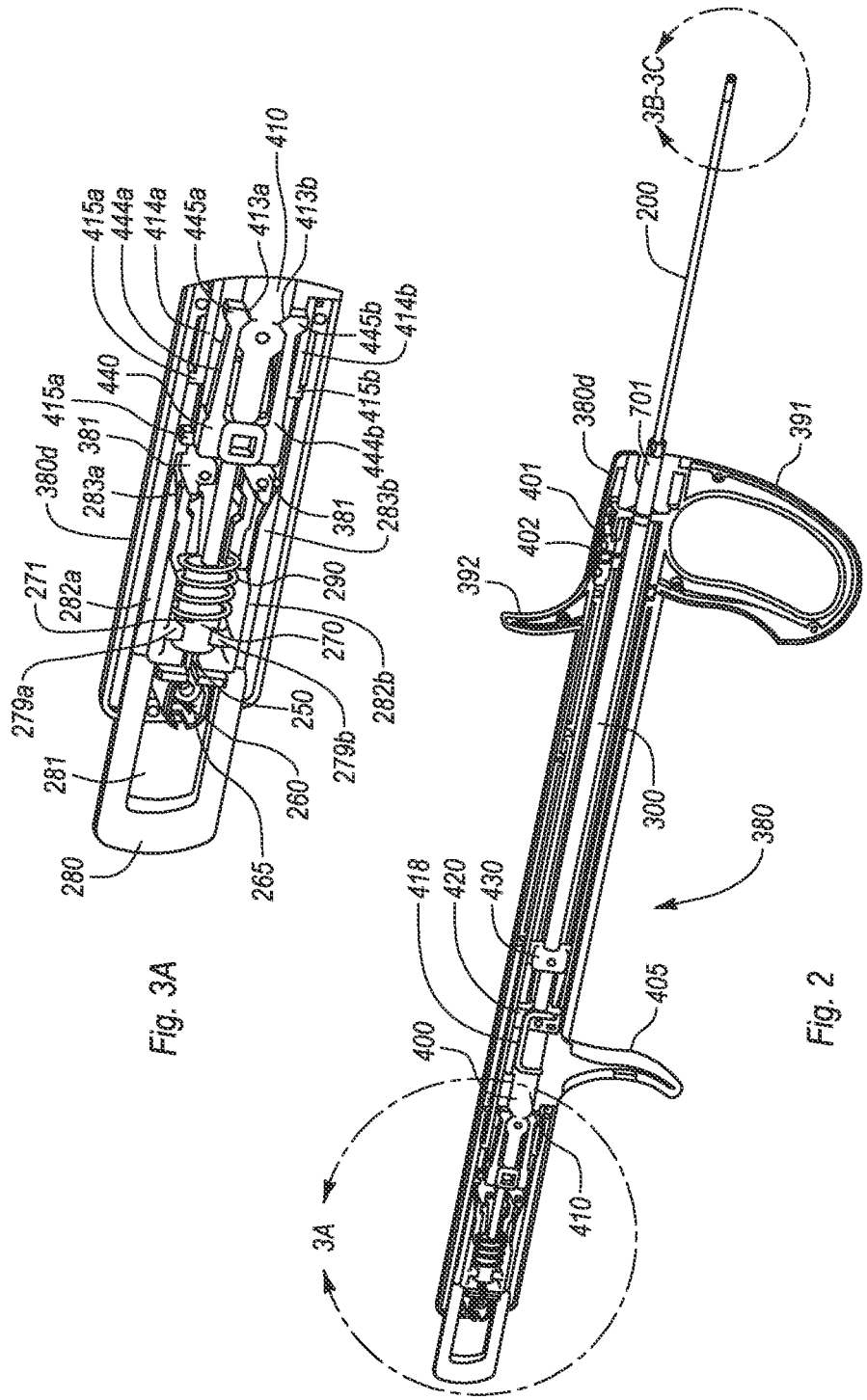

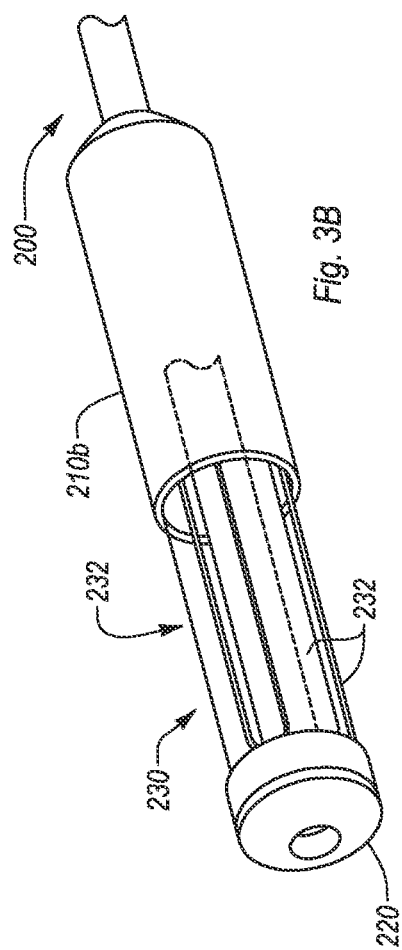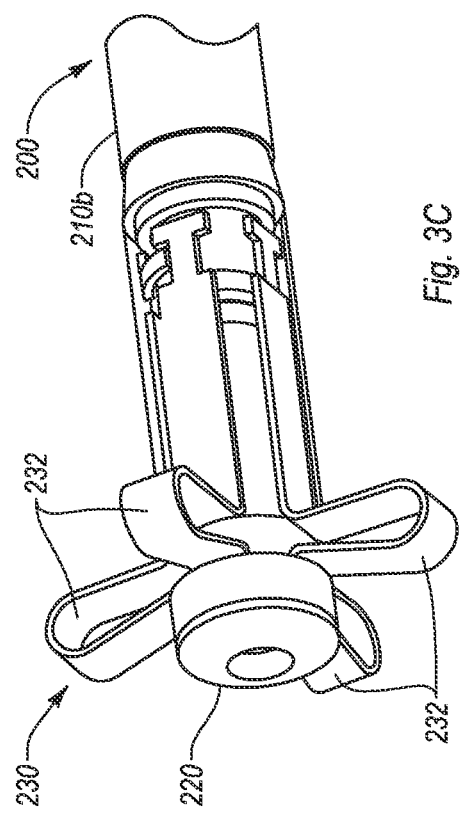

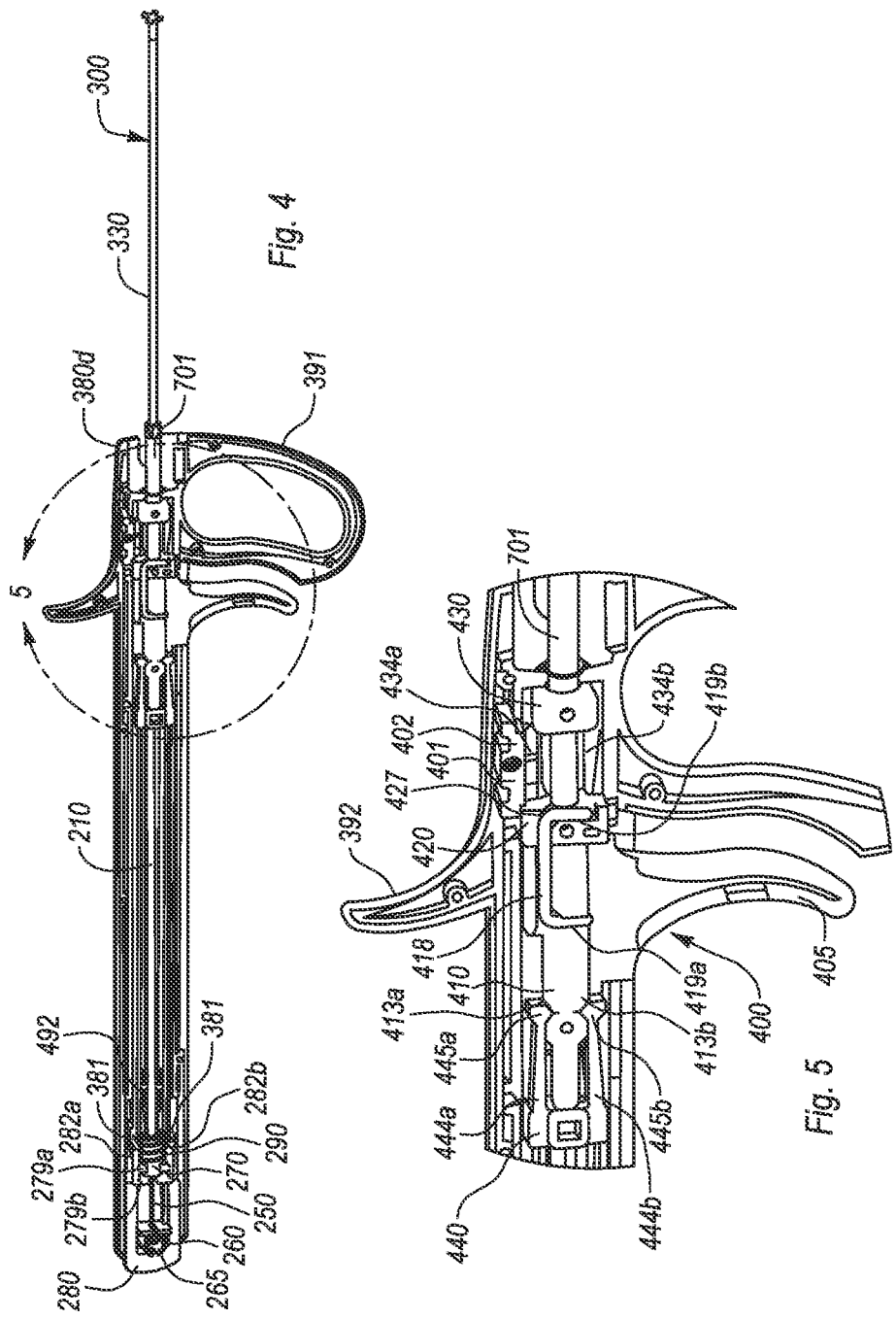

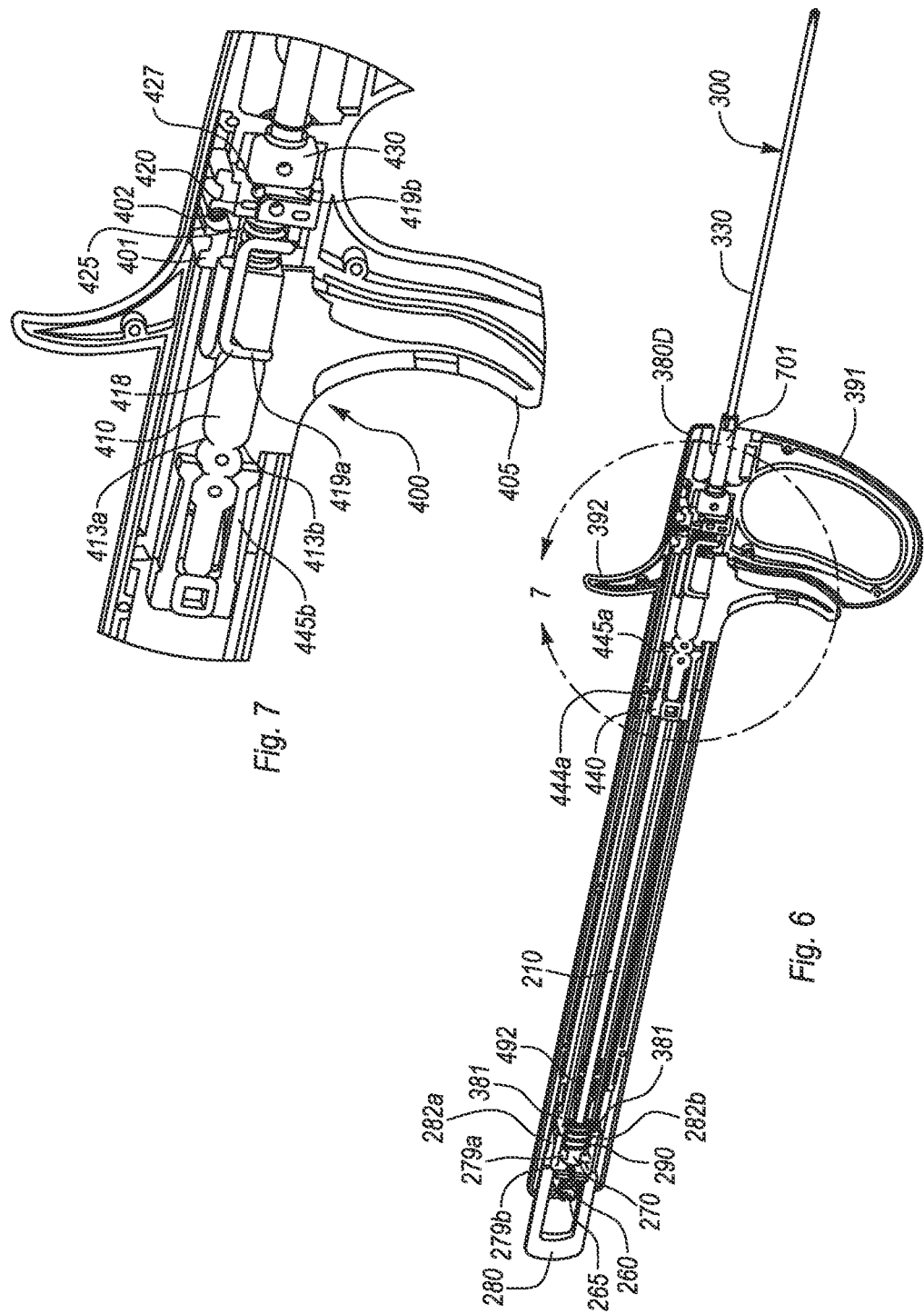

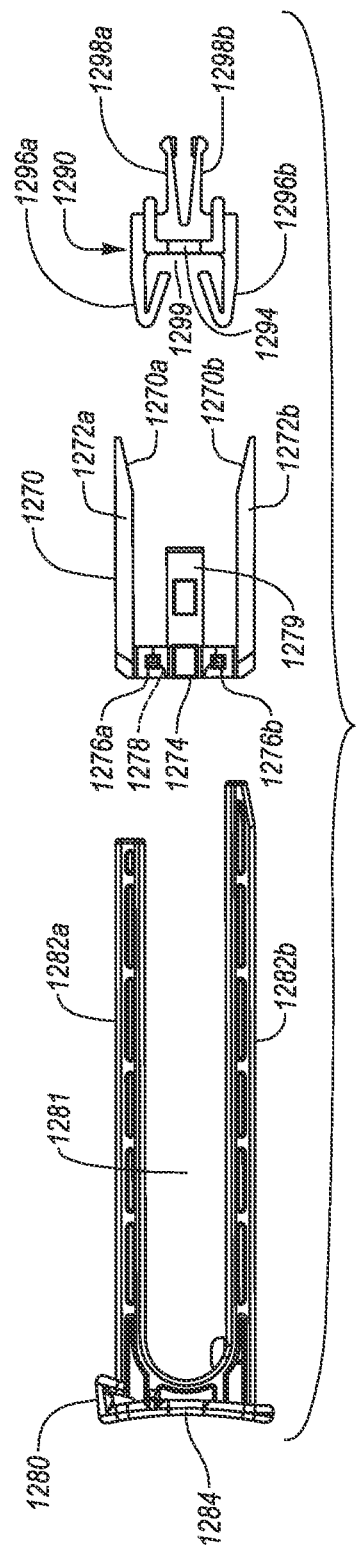
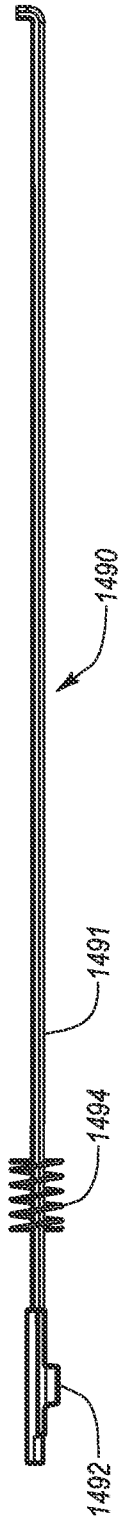
Fig. 11B
Fig. 11C

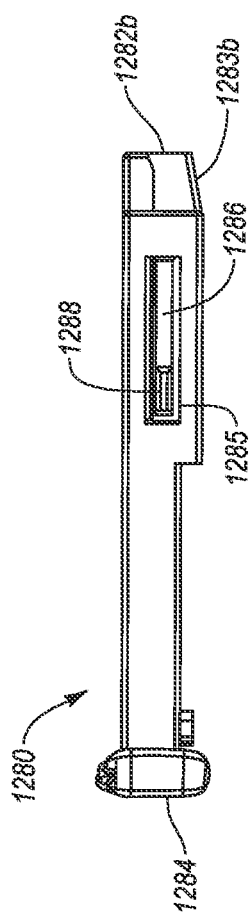
Fig. 11D
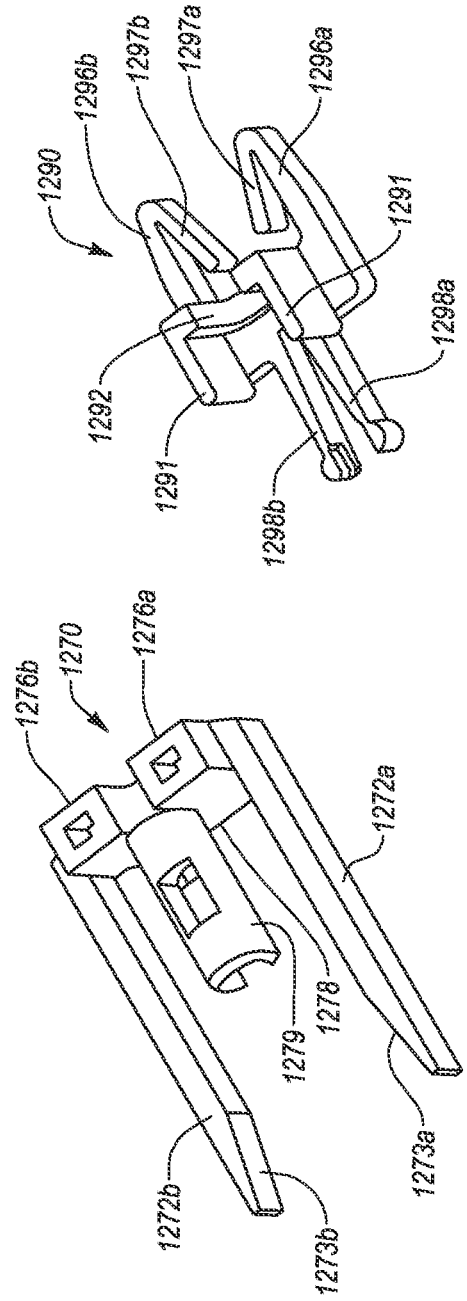
Fig. 11F
Fig. 11E

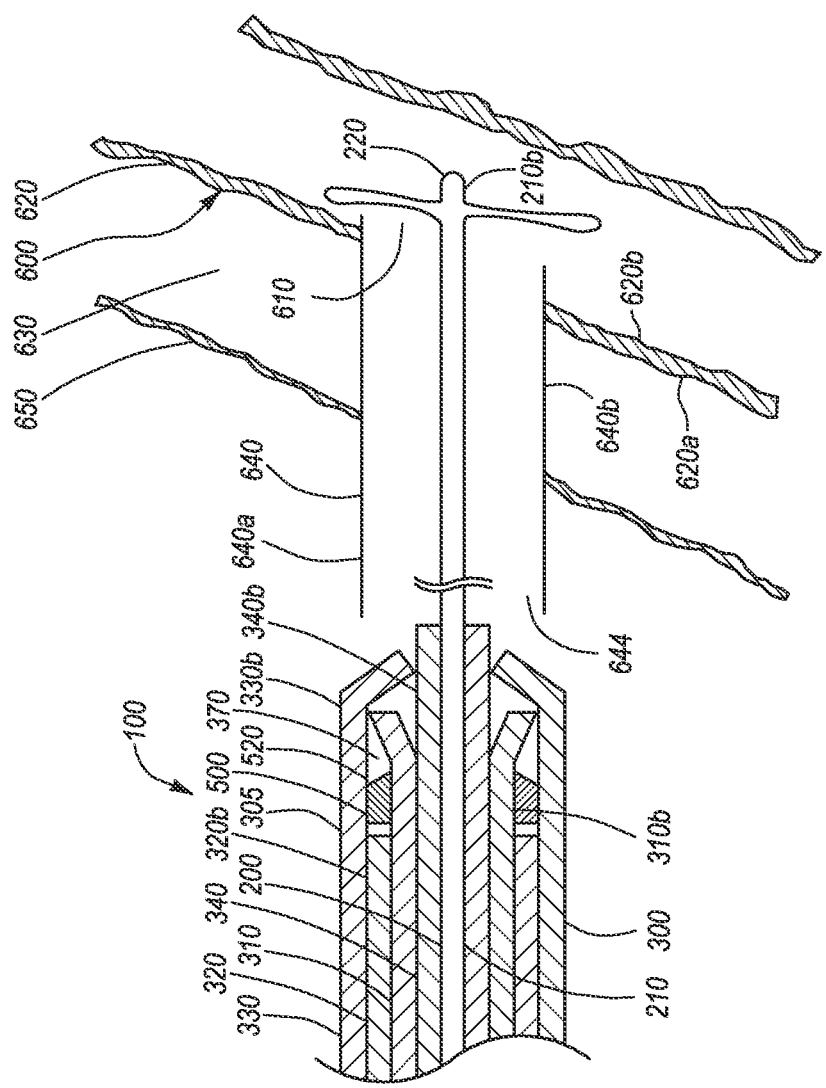

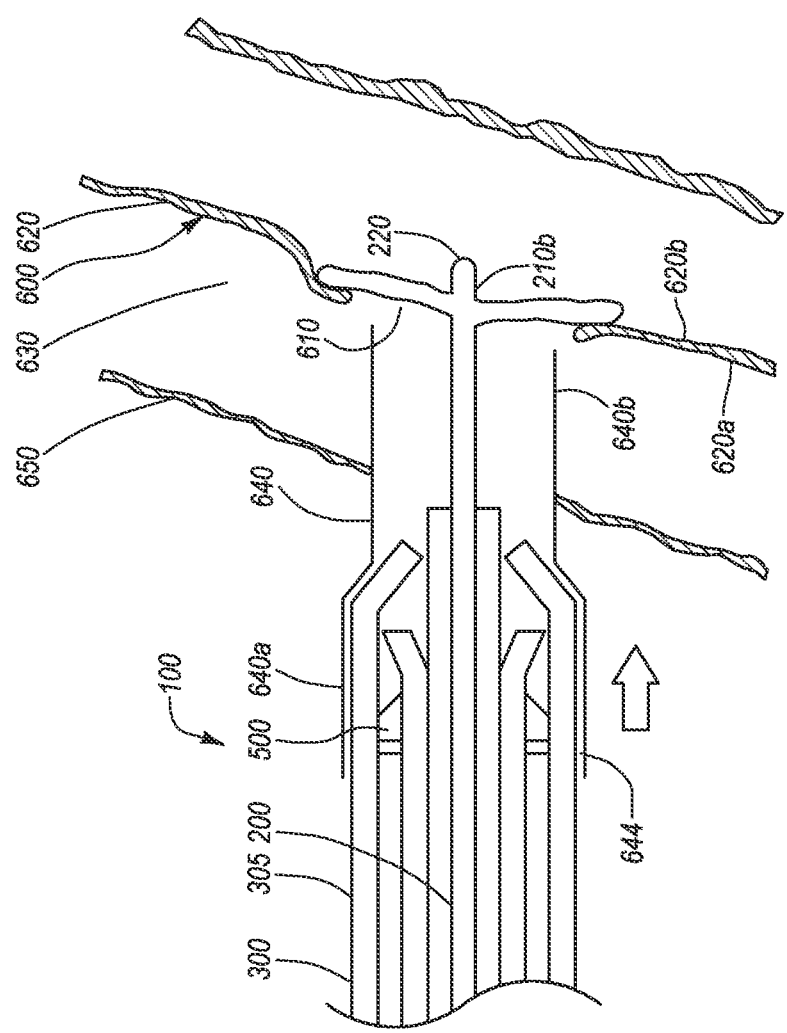

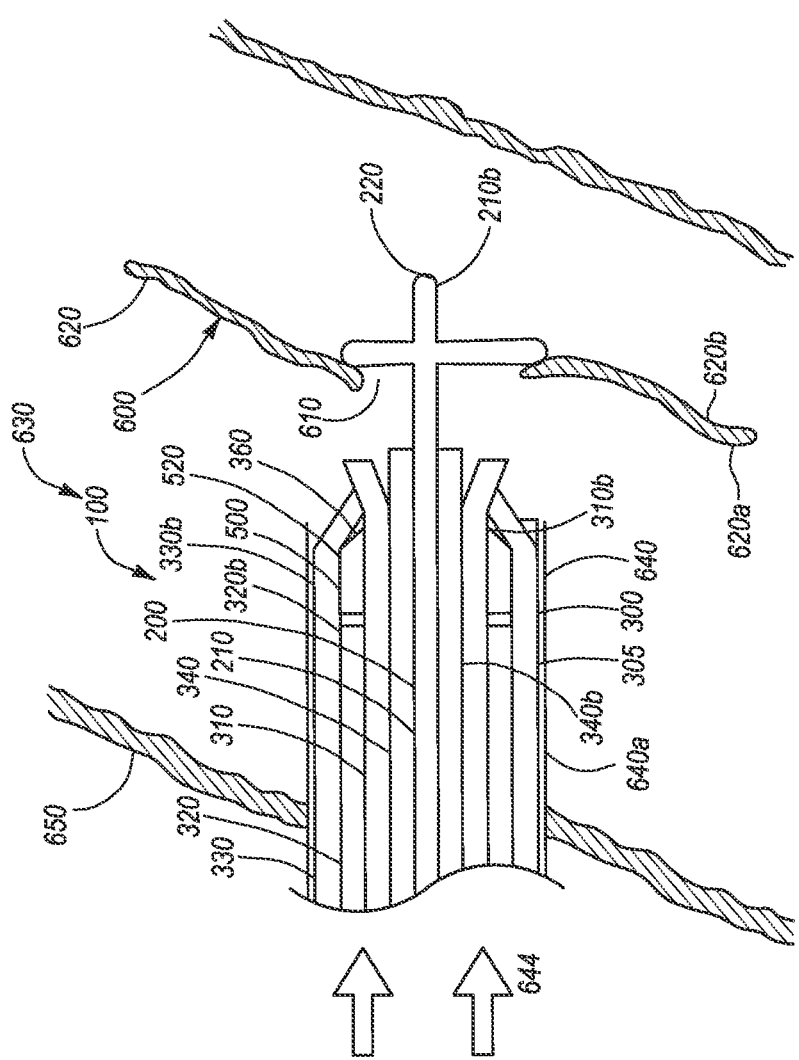

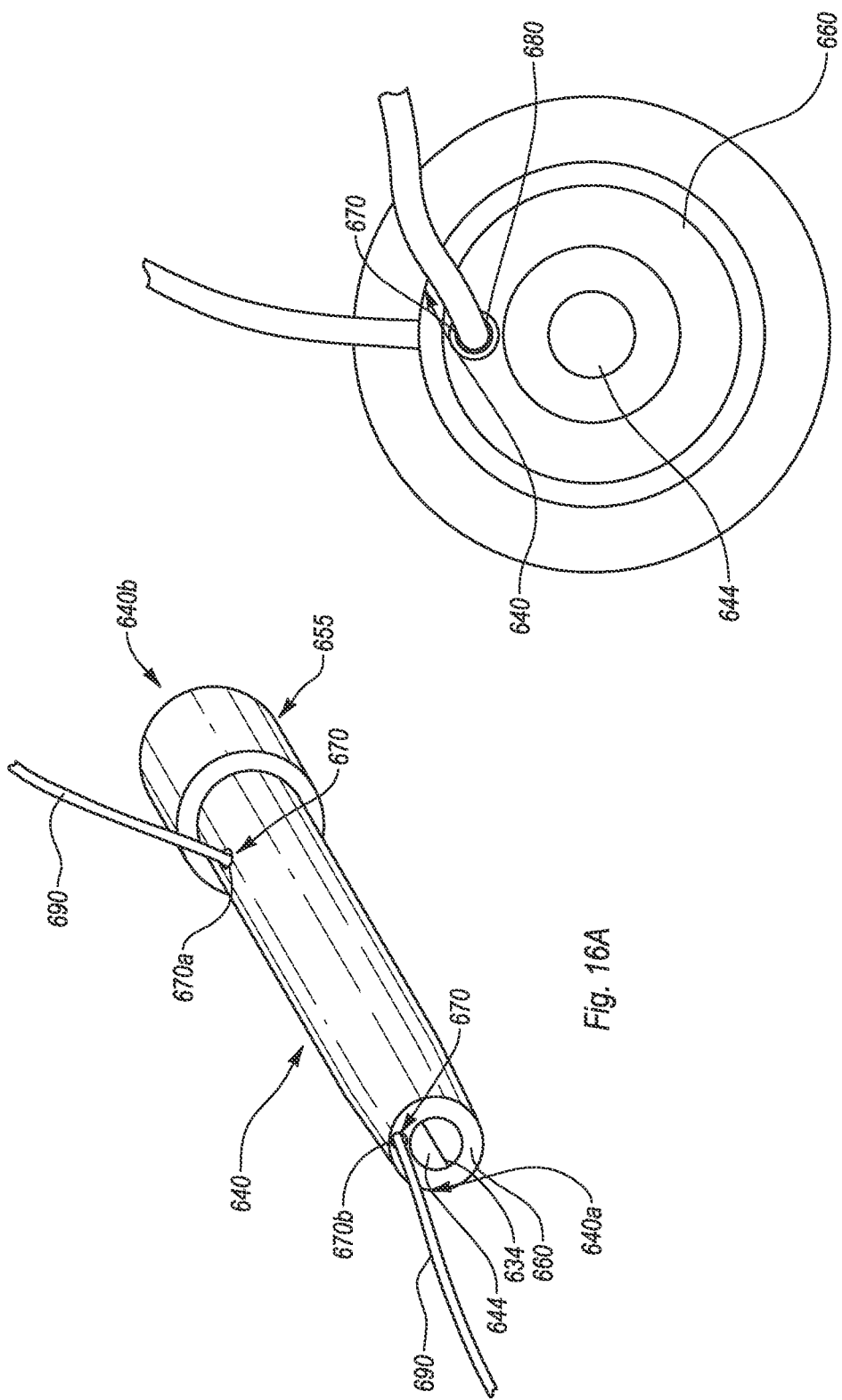

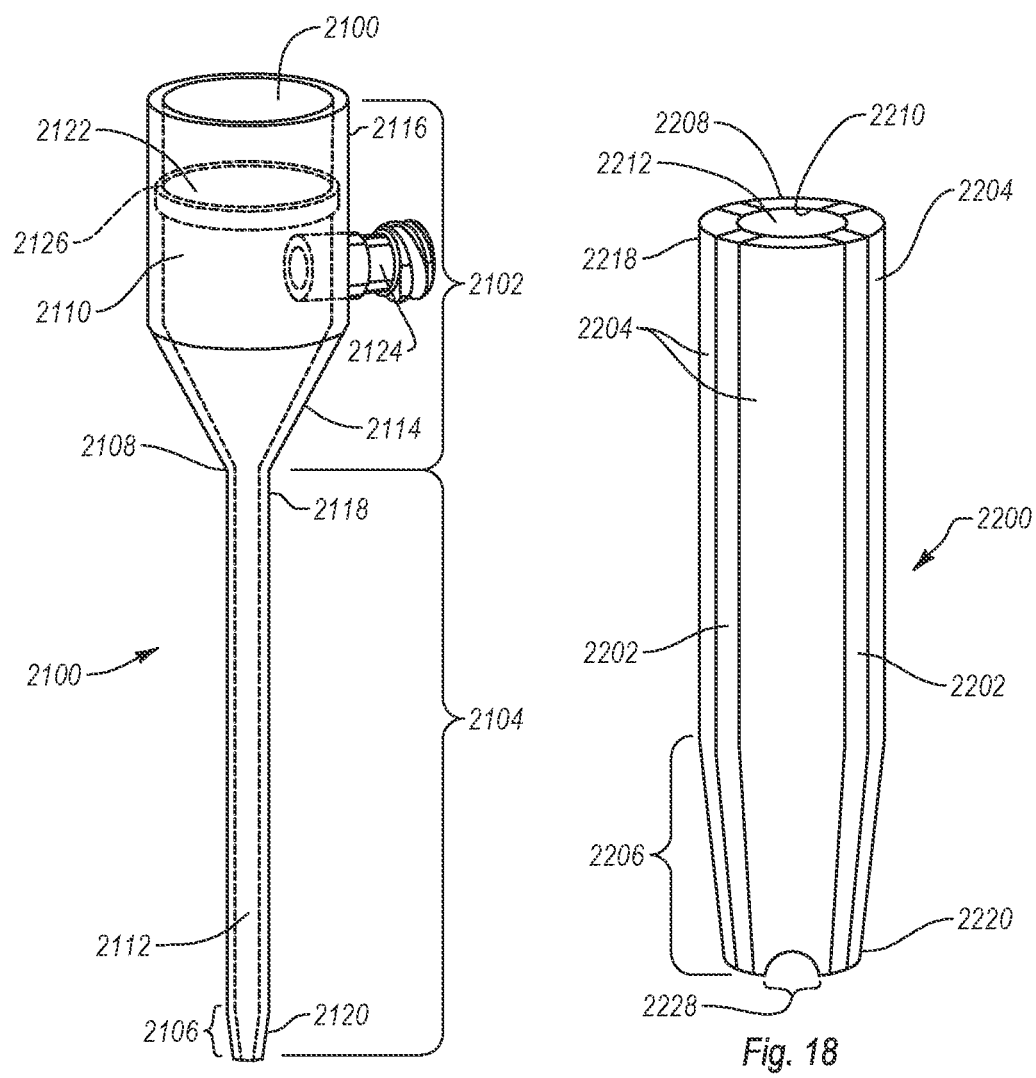

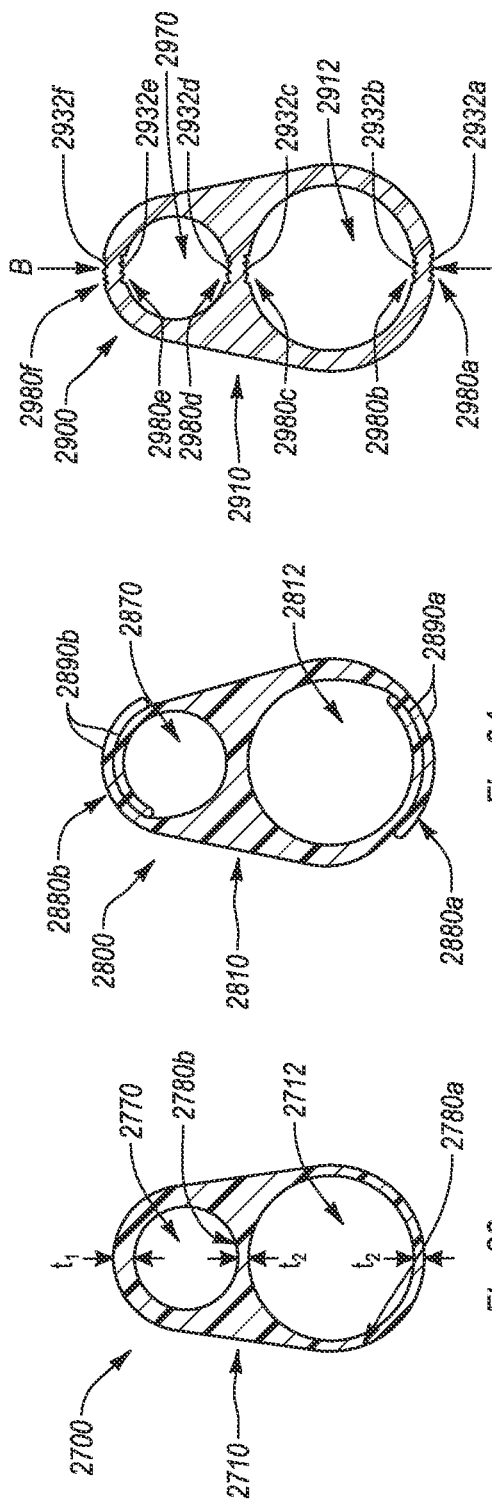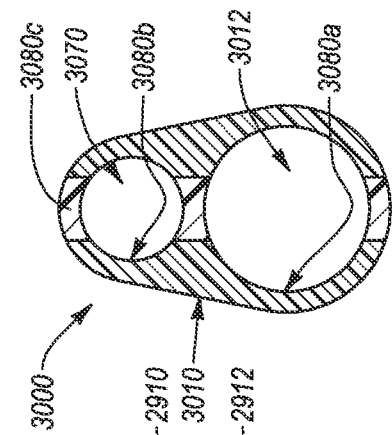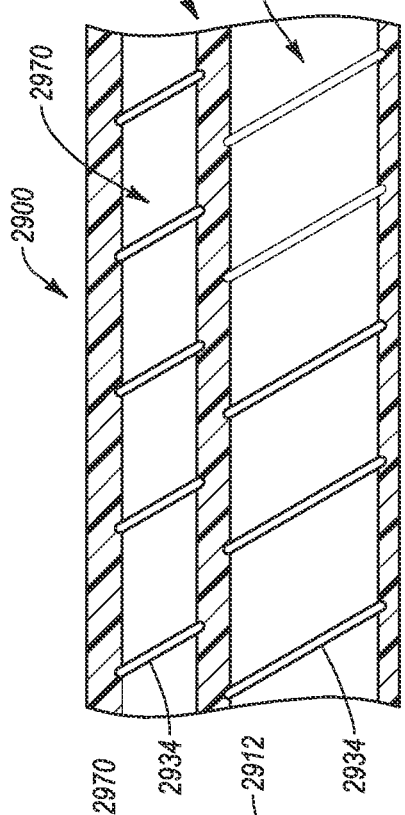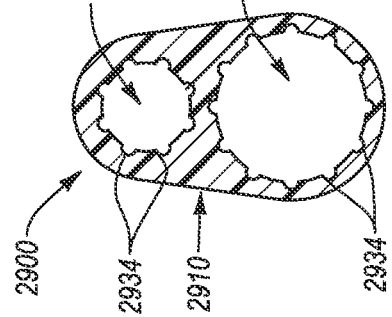

EXPANDABLE INTRODUCER SHEATH TO PRESERVE GUIDEWIRE ACCESS

CROSS-REFERENCE TO RELATED APPLICATIONS

This application is a continuation of U.S. patent application Ser. No. 15/861,970, filed Jan. 4, 2018, which is a continuation of U.S. patent application Ser. No. 13/835,570, filed Mar. 15, 2013, which is (i) a continuation-in-part of U.S. patent application Ser. No. 12/696,792, filed Jan. 29, 2010, which is a continuation-in part of U.S. patent application Ser. No. 11/767,947, filed Jun. 25, 2007, which is a continuation-in-part of U.S. patent application Ser. No. 11/427,308, filed Jun. 28, 2006, (ii) a continuation-in-part of U.S. patent application Ser. No. 11/767,947, filed Jun. 25, 2007, which is a continuation-in-part of U.S. patent application Ser. No. 11/427,308, filed Jun. 28, 2006, (iii) a continuation-in-part of U.S. patent application Ser. No. 12/696,837, filed Jan. 29, 2010, which is a continuation-in-part of U.S. patent application Ser. No. 11/427,308, filed Jun. 28, 2006, and (iv) a continuation-in-part of U.S. patent application Ser. No. 11/427,308, filed Jun. 28, 2006, the entireties of which are each hereby incorporated by reference.

This application relates to U.S. patent application Ser. No. 11/427,301, entitled "Modular Introducer and Exchange Sheath", and filed Jun. 28, 2006 and U.S. patent application Ser. No. 11/427,306, entitled "Introducer Sheath", and filed Jun. 28, 2006, each of which are incorporated herein by reference in its entirety.

This application also incorporates by reference U.S. patent application Ser. No. 10/356,214, U.S. patent application Ser. No. 10/638,115, and U.S. Provisional Patent Application Ser. No. 60/696,069 in their entireties.

BACKGROUND OF THE INVENTION

1. The Field of the Invention

The present invention relates generally to medical devices and methods. More particularly, embodiments of the invention relate to expandable medical devices, such as introducer sheaths, for use during medical procedures.

2. The Relevant Technology

A wide variety of devices have been developed for medical use. One such device is an introducer sheath that facilitates access to body lumen at an access site. Conventionally, introducer sheaths are formed of three or more components that require assembly: a sheath portion, a hub, and a hemostasis valve disposed within the hub. A suitable example of such an assembly is shown in U.S. Pat. No. 5,807,350, which depicts an introducer sheath having a construction similar to that described above, the entirety of which is hereby incorporated by reference.

In practice, introducer sheaths are often used to access a vessel or artery to allow a surgical or medical procedure to be performed. The introducer sheath is generally inserted into a patient's vasculature using the modified Seldinger technique. In the Seldinger technique, a needle is first inserted into the vessel and then followed by a guidewire through the needle. Next, the needle is removed and a sheath/dilator combination is advanced over the guidewire. The sheath/dilator expands the puncture in the vessel to a size suitable to receive the distal end of an introducer sheath. After the distal end of the sheath is disposed within the vessel, the dilator and guidewire are removed, thereby allowing access to the vessel lumen through the introducer sheath.

There are an increasing number of medical procedures that can be performed using sheaths. Medical procedures such as angioplasty, stenting, and intraaortic therapy, are examples of procedures that can include the use of introducer sheaths. In particular, the medical devices (e.g., catheters, balloon pumps) used in these procedures are introduced through the sheath.

Some of these procedures unfortunately require removal of the sheath earlier than desired. For example, intraaortic balloon pump therapy for ventricular insufficiency is often performed using a sheath. In this procedure, a sheath may be inserted into the femoral artery. Next, a balloon pump may be introduced into the patient's vasculature through the sheath and then guided to the aortic arch region. Once the balloon pump is properly positioned in the arch region, it is typically left in place until the ventricular insufficiency is improved to an acceptable level, which may take days.

In this procedure, the balloon pump may be inflated and deflated at a rate that typically matches the heart rate. Thus, the balloon pump is usually inflated during ventricular diastole and deflated during ventricular systole. Because of the use of the balloon pump for the intraaortic therapy, the balloon pump may be larger compared to when it was initially inserted through the sheath. Because of the increased size, removal of the balloon pump also requires the removal of the sheath since the enlarged balloon pump typically cannot fit inside of the sheath tubing. One of the disadvantages of removing the sheath along with the balloon pump is that the opportunity to close the vessel with any vessel closure device through the sheath may be lost.

Furthermore, the user typically removes the guidewire from the patient's body lumen in order to deploy the closure element. However, many users may wish to have guidewire access in case the need arises to re-access the site or if other complications arise upon closing. Thus, it may be desirable to deploy a guidewire into the body lumen in such a way that it does not interfere with the introduction of the closure element.

There is therefore a need for a new introducer sheath to accommodate removal and/or insertion of devices that change in size or that do not work with conventional sheaths. It may also be desirable to provide guidewire access in such a way that a closure element may also be introduced.

BRIEF SUMMARY OF THE INVENTION

These and other limitations are overcome by embodiments of the disclosure, which relates to medical devices and in particular to expandable introducer sheaths. Embodiments of the disclosure provide several designs and methods of manufacture of an expandable introducer sheath. One embodiment is an introducer sheath formed as a unitary device using, for example, and injection molding process or a co-extrusion process.

In one configuration of an expandable introducer sheath, one or more materials are used to form the sheath. At least one of the materials provides elasticity. The elasticity enables the sheath to expand, thereby accommodating the introduction and/or removal of medical devices that could not previously be accommodated.

In one configuration, the introducer sheath includes a hub portion and a tubular portion. A valve member (such as a hemostasis valve) can be disposed into the hub portion either during the molding process or after the initial molding process. The hemostasis valve can be retained either by an additional element such as a cap or through an element formed during the molding process or during a subsequent molding process.

The tubular portion can include a sheath portion and an elastic portion, which can be formed as a unitary portion through injection molding or co-extrusion processes, for example. The elastic portion of the sheath may be an elastomer that is integrated with another material in the sheath portion that provides rigidity and/or prevents a lumen of the tubular portion from collapsing. When a medical device is withdrawn, for example, the elastic portion can expand thereby permitting the medical device to be withdrawn without splitting the introducer sheath. Advantageously, this enables the use of a subsequent medical device, such as a vessel closure device, to be introduced through the intact sheath, whether or not the vessel closure device splits or cuts the introducer sheath during use. An embodiment of an introducer sheath is described. The introducer sheath includes a tubular body extending from a distal end toward a proximal end. The tubular body includes a lumen defined at least partially by a wall. The tubular body includes a channel disposed within the wall and configured to receive a guidewire. The tubular body includes an expandable divider expandable to increase a cross-sectional area of the lumen.

In some embodiments, the expandable divider is located between the lumen and the channel. The expandable divider, in further embodiments, includes a first end connected to the wall and a second end connected to the wall. In still further embodiments, a first linear length is defined from the first end of the expandable divider toward the second end of the expandable divider. A first curve length, in yet further embodiments, is defined from the first end of the expandable divider toward the second end of the expandable divider along a curve defined by the expandable divider.

In some embodiments, the first curve length is larger than the first linear length. The first curve length, in further embodiments, is about fifty percent larger than the first linear length. In still further embodiments, the expandable divider elastically deforms when the expandable divider expands beyond a predetermined diameter and/or a predetermined expansion distance. The expandable divider, in yet further embodiments, plastically deforms when the expandable divider expands beyond a predetermined diameter and/or a predetermined expansion distance.

The tubular body, in some embodiments, includes an entry portion at the distal end that facilitates entry of a medical device. In further embodiments, the tubular body is configured to expand to accommodate the medical device without splitting an outer surface of the tubular body. The expandable divider, in still further embodiments, is in a shape selected from the group consisting essentially of a sinusoidal shape, a concertina shape, an overlapping shape, a serpentine shape, or combinations thereof.

In some embodiments, the expandable divider is expandable from a pre-expanded state where the lumen has a pre-expanded dimension to an expanded state where the lumen has an expanded dimension before the wall of the lumen deforms. The pre-expanded dimension, in further embodiments, is a diameter of about eight French in a pre-expanded state. In still further embodiments, the pre-expanded dimension is a diameter of about ten French in an expanded state.

Another embodiment of an introducer sheath is described. The introducer sheath includes a hub portion extending from a distal end toward a proximal end having a hub lumen formed therein. The introducer sheath includes a tubular body extending from a distal end toward a proximal end. The tubular body includes a lumen defined at least partially by a wall. The tubular body includes a channel disposed within the wall and configured to receive a guidewire. The tubular body includes an expandable divider expandable to increase a cross-sectional area of the lumen.

In some embodiments, the expandable divider is located between the lumen and the channel. The expandable divider, in further embodiments, includes a first end connected to the wall and a second end connected to the wall. A first linear length, in still further embodiments, is defined from the first end of the expandable divider toward the second end of the expandable divider and a first curve length is defined from the first end of the expandable divider toward the second end of the expandable divider along a curve defined by the expandable divider.

The first curve length, in some embodiments, is larger than the first linear length. In further embodiments, the expandable divider elastically deforms when the expandable divider expands beyond a predetermined diameter and/or a predetermined expansion distance. In still further embodiments, the tubular body includes an entry portion at the distal end that facilitates entry of a medical device. The tubular body, in yet further embodiments, is configured to expand to accommodate the medical device without splitting an outer surface of the tubular body. The expandable divider, in even further embodiments, is in a shape selected from the group consisting essentially of a sinusoidal shape, a concertina shape, an overlapping shape, a serpentine shape, or combinations thereof.

An embodiment of a method for introducing a medical device into a body is described. The method includes positioning a sheath upon a guidewire disposed within a body lumen. The sheath includes a tubular body extending from a distal end toward a proximal end. The tubular body includes a lumen defined at least partially by a wall. The tubular body includes a channel disposed within the wall and configured to receive the guidewire. The tubular body includes an expandable divider expandable to increase a cross-sectional area of the lumen. The method includes introducing the sheath into the body lumen. A first medical device is selectively inserted into the body lumen through the sheath.

In some embodiments, the expandable divider is located between the lumen and the channel. The expandable divider, in further embodiments, includes a first end connected to the wall and a second end connected to the wall. In still further embodiments, a first linear length is defined from the first end of the expandable divider toward the second end of the expandable divider and a first curve length is defined from the first end of the expandable divider toward the second end of the expandable divider along a curve defined by the expandable divider. The first curve length being larger than the first linear length, in yet further embodiments.

The tubular body, in some embodiments, includes an entry portion at the distal end that facilitates entry of a medical device. In further embodiments, the tubular body is configured to expand to accommodate the medical device without splitting an outer surface of the tubular body. The expandable divider, in still further embodiments, is in a shape selected from the group consisting essentially of a sinusoidal shape, a concertina shape, an overlapping shape, a serpentine shape, or combinations thereof.

In some embodiments, the expandable divider is expandable from a pre-expanded state where the lumen has a pre-expanded dimension to an expanded state where the lumen has an expanded dimension before the wall of the lumen deforms. A second medical device, in further embodiments, is selectively inserted into the body lumen through the sheath.

An embodiment of an introducer sheath is described. The introducer sheath includes a tubular body. The tubular body extending from a distal end toward a proximal end. The tubular body includes a lumen defined at least partially by a wall. The lumen also includes a secondary channel disposed within the wall and configured to receive a guidewire.

Another embodiment of an introducer sheath is described. The introducer sheath includes a hub portion that extends from a distal end toward a proximal end. The hub portion includes a hub lumen formed therein. The introducer sheath includes a tubular body extending from a distal end toward a proximal end. The tubular body includes a lumen defined at least partially by a wall. The introducer sheath includes a secondary channel disposed within the wall. The secondary channel is configured to receive a guidewire. The introducer sheath includes a portion of weakened structural integrity. The portion of weakened structural integrity is located between the lumen and the secondary channel. The portion of weakened structural integrity splits when the body expands beyond a predetermined diameter and/or a predetermined expansion distance to increase a cross-sectional area of the tubular body.

In some embodiments, the tubular body includes at least one deformable expandable portion configured to increase a cross-sectional area of the tubular body. In further embodiments, the deformable expandable portion splits when the deformable expandable portion expands beyond a predetermined diameter and/or a predetermined expansion distance. A portion of the tubular body, in still further embodiments, splits when expanded beyond a predetermined diameter and/or a predetermined expansion distance. At least one deformable expandable portion, in some embodiments, is located between the lumen and the secondary channel.

The tubular body, in some embodiments, includes a geometric pattern formed on at least a portion of an inner wall of the tubular body to facilitate splitting a portion of the tubular body. In some embodiments, the geometric pattern, includes a groove that facilitates splitting of at least a portion of the tubular body, a groove that facilitates splitting of at least the deformable expandable portion, a separation line to facilitate splitting of at least a portion of the tubular body, a separation line to facilitate splitting of at least the deformable expandable portion, a plurality of grooves running parallel to a longitudinal axis of the tubular body, and/or a plurality of grooves that are not parallel to the longitudinal axis.

In some embodiments, at least one deformable expandable portion includes an elastic portion comprising a first material including an elastomer and the tubular body further includes at least one sheath portion comprising a second material. In further embodiments, the at least one elastic portions comprise a plurality of strips and the at least one sheath portions comprise a plurality of strips, each strip of the elastic portion being bonded to at least one adjacent strip of the sheath portion. In still further embodiments, each strip of the at least one elastic portion includes an interlocking feature to attach with at least one adjacent strip of the sheath portion.

The tubular body, in some embodiments, includes an entry portion at the distal end. The entry portion facilitates entry of a medical device, in further embodiments. The tubular body, in still further embodiments, is configured to expand to accommodate the medical device without splitting an outer surface of the tubular body.

At least one of the deformable expandable portions, in some embodiments, includes a plurality of lumens formed in a wall of the deformable expandable portion. In these embodiments, the plurality of lumens provide elasticity to the deformable expandable portion.

An embodiment method for introducing a medical device into a body is described. A sheath is positioned upon a guidewire disposed within a body lumen. The sheath includes a tubular body extending from a distal end toward a proximal end. The tubular body includes a lumen defined at least partially by a wall. A secondary channel is disposed within the wall and configured to receive the guidewire. At least one deformable expandable portion is configured to increase a cross-sectional area of the tubular body. The sheath is introduced into the body lumen. One or more medical devices are selectively inserted into the body lumen through the sheath. In some embodiments, one of the at least one deformable expandable portions is located near an inner wall of the lumen and/or on an inner wall of the secondary channel.

In some embodiments, the introducer sheath may include a fluid port associated with the hub portion to facilitate the introduction or removal of fluid from vasculature. The fluid port, in further embodiments, may include an alignment mechanism that aligns a medical device introduced through the sheath.

The hub portion, in some embodiments, may include a valve member that seals the hub portion. In further embodiments, the valve member may include an elastomeric body having at least one slit formed therein to allow selective insertion and removal of a medical device while maintaining a fluid tight seal around the medical device.

In some embodiments, the distal end of the hub portion may include a transition from the distal end of the hub portion to the proximal end of at least one of the tubular inner portion and the tubular outer portion. The introducer sheath, in further embodiments, may include a strain relief at the transition. In still further embodiments, the tubular portion may include a tapered end formed at the distal end of the tubular member.

An embodiment of a method for manufacturing an introducer sheath is described. The method includes forming an inner portion of a tubular portion. The tubular portion extends between a proximal end and a distal end. The inner portion defines a lumen. The method includes forming an outer portion around the inner portion. The outer portion encloses less than the entirety of the outer surface of the inner portion between the proximal end and the distal end.

In some embodiments, the first material may include expandable PTFE. The method, in further embodiments, may include forming a hub portion having a lumen formed therein extending from at least one of the tubular inner portion and the tubular outer portion. In still further embodiments, forming the inner portion, the outer portion, the hub portion, or combinations thereof may include using an injection molding process, an overmolding process, an extrusion process, a co-extrusion process, a bump extrusion process, other processes, or combinations thereof. The hub portion and at least one of the tubular inner portion and the tubular outer portion, in yet further embodiments, may be formed as a unitary member.

An embodiment of a method for performing a medical procedure is described. The method includes introducing a sheath into a lumen of a patient. The sheath has a first unexpanded dimension. The method includes inserting a first medical device having an outer dimension into the lumen through the sheath to perform a medical procedure. At least a tubular member of the sheath expands to a second expanded dimension to accommodate the outer dimension of the first medical device.

In some embodiments, the method may include inserting a second medical device through the sheath. Inserting a second medical device through the sheath, in further embodiments, may include introducing a vessel closure device through the sheath and/or closing the lumen of the patient with the vessel closure device. In still further embodiments, The sheath may include a tubular portion extending from the hub portion. The tubular portion, in yet further embodiments, may include at least one elastic portion elastically deformable to increase a cross sectional area of the tubular portion.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 2 illustrates the assembled carrier assembly and triggering assembly of the apparatus shown in FIGS. 1A and 1B.

FIG. 3A illustrates a close-up view of the proximal end of the apparatus shown in FIG. 2.

FIG. 3B illustrates a close-up view of the distal end of the apparatus shown in FIG. 2 in an unexpanded state.

FIG. 3C illustrates a close-up view of the distal end of the apparatus shown in FIG. 2 in an expanded state.

FIG. 4 illustrates the apparatus of FIG. 2 after distal advancement of the locator assembly, the triggering system and the carrier assembly.

FIG. 5 illustrates a close-up view of the triggering system and carrier assembly of the apparatus shown in FIG. 4.

FIG. 6 illustrates the apparatus of FIG. 1A-1B after the clip has been released to close the opening in the tissue.

FIG. 7 illustrates a close-up view of the triggering system and carrier assembly of the apparatus of FIG. 1A-1B after the clip has been released to close the opening in the tissue.

FIG. 11B illustrates a portion of a locator control system of the alternative embodiment of FIG. 9.

FIG. 11C illustrates a portion of a locator release system of the alternative embodiment of FIG. 9.

FIG. 11D illustrates a side view of a plunger of the locator control system of FIG. 11B of the alternative embodiment of FIG. 9.

FIG. 11E illustrates a perspective view of a tubular body block of the locator control system of FIG. 11B of the alternative embodiment of FIG. 9.

FIG. 11F illustrates a perspective view of a spring retainer of the locator control system of FIG. 11B of the alternative embodiment of FIG. 9.

FIGS. 15A-15K illustrate various steps in the deployment of embodiments of the present invention.

FIGS. 16A-16B illustrate various embodiments of a sheath containing a secondary channel for the introduction of a second guidewire.

FIG. 17 is a plan view of an exemplary embodiment of an introducer sheath in accordance with the present invention;

FIG. 18 illustrates a cross-sectional view of one embodiment of the introducer sheath in FIG. 17;

FIGS. 23-26 illustrate cross-sections of various embodiments of a tubular body of an introducer sheath.

DETAILED DESCRIPTION

Figure 1A:
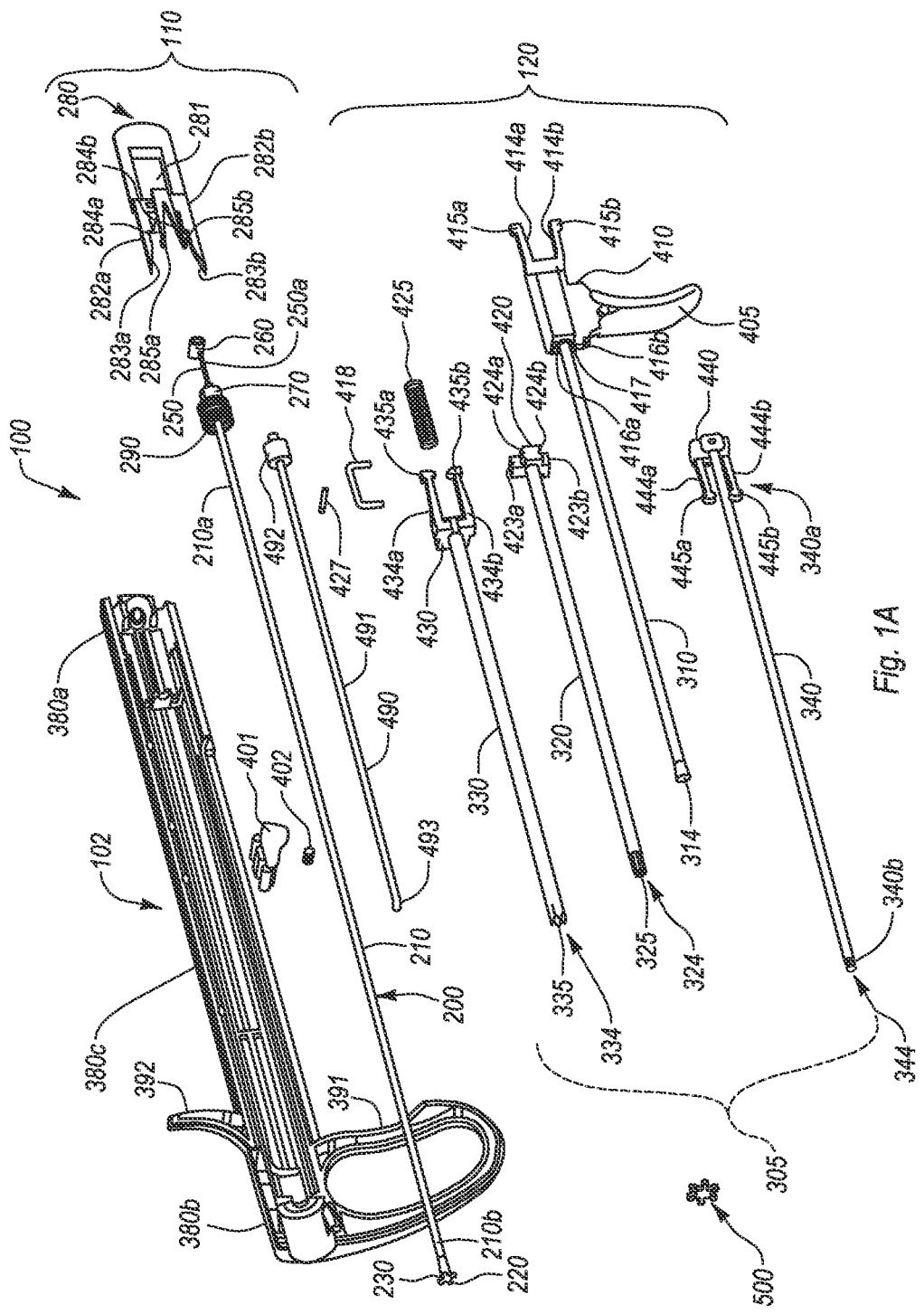
FIG. 1A illustrates an assembly view of the components of one embodiment according to the present invention for closing openings in blood vessel walls.

Embodiments of the invention relate to a device that is expandable to cooperate with medical devices. In some embodiments, the device may be expandable to cooperate with medical devices that may have a larger dimension and/or may become enlarged in dimension during use. For instance, in one configuration, the device can be an expandable introducer sheath that can accommodate removal of enlarged medical devices without removing the introducer from the delivery site. In other embodiments, the device may be expandable to cooperate with medical devices that are too large to be inserted and/or removed prior to use. For example, the medical device may have a larger measurement, i.e. diameter, width, etc., than a measurement of the device.

As such, the sheath or at least a portion of the introducer sheath can expand to accommodate the introduction and/or removal of medical devices that could not ordinarily be accommodated in conventional sheaths. At the same time, the sheath can be formed to have desirable stiffness, kink resistance, and/or flexibility for insertion and positioning in at least a portion of a body lumen. Embodiments of the sheath are depicted in the drawings, which are not necessarily to scale and are not intended to limit the scope of the invention. It will be understood that the benefits of the present invention are not limited to application with an introducer sheath. Rather, other medical devices may be modified based upon the teaching contained herein such that they to can provide the functionality of accommodating removal of enlarged medical devices.

In one configuration, an expandable portion is provided that may have a curve length that is longer than a linear length between a first and a second end. In use, the expandable portion may be deflected from a lumen toward a secondary channel to accommodate a device of larger size.

Turning to the introducer sheath in accordance with the present invention, the sheath will be described herein as having portions or members, though it shall be understood that the sheath as described herein can be formed as a unitary unit, formed, by way of example, using a co-extrusion process or an injection molding process, or a sheath fabricated from the assembly of separate parts. As such, the various members or portions are used herein for clarification only and in no way limit the applicability of description herein to other configurations of the sheath and/or medical devices.

Generally stated, an exemplary introducer sheath can include a hub member or portion having a proximal end and a distal end. The proximal end of the sheath can be configured to receive a flexible valve member therein. The sheath can further include an elongated tubular member or portion generally extending from the distal portion of the hub portion. The elongated tubular body, in one configuration, can be generally axially aligned with an axis of the hub portion, with the lumen of the tubular body being aligned with a lumen of the hub portion. Alternatively, the lumen of the tubular body can be aligned with a lumen of the hub portion, whether or not axially aligned. The aligning of the lumens can occur during manufacture, such as when the hub portion and the sheath are formed as a single integrated unit or when separate components are joined together. In one embodiment, the tubular body is configured to expand while still providing the necessary stiffness and/or kink resistance to the sheath.

An introducer sheath or portions thereof can be formed using one or more materials. Typically, the materials used in forming the introducer sheath are medical grade synthetic materials or plastics. Exemplary materials may include, but are not limited to, flexible PVC, polyurethane, silicone, liner low-density polyethylene (LLDPE), polyethylene, high density polyethylene, (DHPE), polyethylene-lined ethylvinyl acetate (PE-EVA), polypropylene, latex, thermoplastic rubber, polytetrafluorethylene (PTFE), expandable polytetrafluorethylene (ePTFE), fluroethylene-propylene (FEP), perfluoralkoxy (PFA), ethylene-tetrafluoroethylene-copolymer (ETFE), ethylene-chlorotrifluoroethylene (ECTFE), polychloro-trifluoroethylene (PCTFE), polyimide (PI), polyetherimide (PEI), polyetherketone (PEEK), polyamide-imide (PAI), other fluoropolymers, and the like.

Exemplary materials used in the sheath or a portion of the sheath can also include elastomers or thermoplastic elastomers. Examples of elastomers include, but are not limited to, natural rubber, silicone rubber, polyurethane rubber, polybutadiene, polyisoprene, chlorosulfonated polyethylene, polysulfide rubber, epichlorohydrin rubber, resilin, ethylene propylene rubber, and the like or any combination thereof. These materials provide the elasticity that enable the sheath to expand and/or contract to accommodate the removal/insertion of a medical device as required. Other materials that can be used can include, but are not limited to, dip coated type silicones.

In other embodiments, the materials suitable for use in an introducer sheath are configured to have chemical resistance, crack resistance, no toxicity, Food and Drug Administration (FDA) compliance, non-electrically conductive, dimensional stability, and/or be sterilized by ethylene oxide, gamma radiation, autoclave, UV light, ozone, and the like.

In addition, the selection of materials for a particular sheath can depend on a variety of factors that include, but are not limited to, a particular stiffness and/or flexibility of the sheath or any portion of the sheath, including the desired column stiffness and strength to enable insertion of the sheath, a particular shear or split strength for the sheath or any portion of the sheath, the ability to resist kinking, and the like. For example, the material used for the tubular body of the introducer sheath may be selected based on shear strength or how easily it can be split. Further, certain features of the sheath may be formed to enhance certain characteristics. For example, a strain relief portion may be formed to resist kinking while the elongated tubular body may be formed to facilitate splitting.

When more than one material is used to form the sheath or to form specific portions of the introducer sheath, the materials may be selected, in addition to the factors identified herein, on a bond strength between the materials or on the elasticity of a particular material. The bond strength, for example, may have an impact on the splitability of the sheath or of a portion of the sheath. The bond strength may also affect the ability of the sheath to expand without splitting.

When an elastomer is used in the sheath or a portion of the sheath, the elasticity of the elastomer enables the sheath or a portion of the sheath to at least partially deform, resiliently deform, or elastically expand as needed to accommodate a medical device and then return or substantially return to its configuration prior to deforming or expanding. Advantageously, the ability to deform and/or expand permits a device, such as an expanded or expandable balloon, to be withdrawn through the sheath without removing the sheath, for example from a patient's vasculature. This maintains access to the patient's vasculature without the difficulty of inserting another sheath or medical device through the puncture site. Further, maintaining the introducer sheath in place allows a physician or technician to insert one or more additional medical devices, such as a vessel closure device, using the introducer sheath.

Embodiments extending to methods, systems, and apparatuses for closing and/or sealing openings in a blood vessel or other body lumen formed during a diagnostic or therapeutic procedure are described. These embodiments may be used in conjunction with embodiments of the device that is expandable to cooperate with medical devices. Some of the apparatuses of the present invention are configured to deliver a closure element through tissue and into an opening formed in and/or adjacent to a wall of a blood vessel or other body lumen.

Since current apparatuses for sealing openings formed in blood vessel walls may snag tissue adjacent to the openings during positioning and may not provide an adequate seal, an apparatus that is configured to prevent inadvertent tissue contact during positioning and to engage tissue adjacent to the opening can prove much more desirable and provide a basis for a wide range of medical applications, such as diagnostic and/or therapeutic procedures involving blood vessels or other body lumens of any size. Further, since current apparatuses for sealing openings formed in blood vessel walls are typically one-size and do not provide a mechanism to accommodate for variations in the size or configuration of the physician or clinician's hands, an apparatus that varies its operational configuration to accommodate for physician or clinician hand sizes can prove much more desirable and beneficial to the medical arts. These results, whether individually or collectively, can be achieved, according to one embodiment of the present invention, by employing an apparatus as shown in the figures and described in detail below.

The apparatuses of the present invention are configured to deliver a closure element through tissue and into an opening formed in and/or adjacent to a wall of a blood vessel or other body lumen. The apparatus can be configured to receive and retain a closure element such that the closure element can be disposed substantially within the apparatus. The apparatuses in accordance with the present invention generally include a handle portion having a proximal end and a distal end, a locator and clip delivery assembly extending from the distal end of the handle portion, and a locator actuator disposed at the proximal end of the handle portion.

FIGS. 1-15K generally illustrate several embodiments of medical devices for delivering a closure element that may be used in conjunction with embodiments of an expandable sheath. Other embodiments of medical devices may also be used conjunction with embodiments of an expandable sheath.

Referring now to FIG. 1, an exploded assembly view of one closure apparatus is shown in accordance with the present invention. As shown in FIG. 1, the apparatus can include a housing that receives or retains a plurality of tubular members. The tubular members can be concentrically disposed within the housing of the device, with each tubular member having an associated block member fixedly attached to the proximal end thereof. The block members can be configured to interact with each other as well as with features of the housing, such as through movement of a triggering system. The interaction of the tubular members, the blocks, and the triggering system will be described in greater detail below. Also described below will be additional details regarding the handle portion of the housing and the manner by which the movement of the tubular members and the triggering system results in variation of the devices operational configuration to accommodate for physician or clinician hand sizes.

Figure 1B:
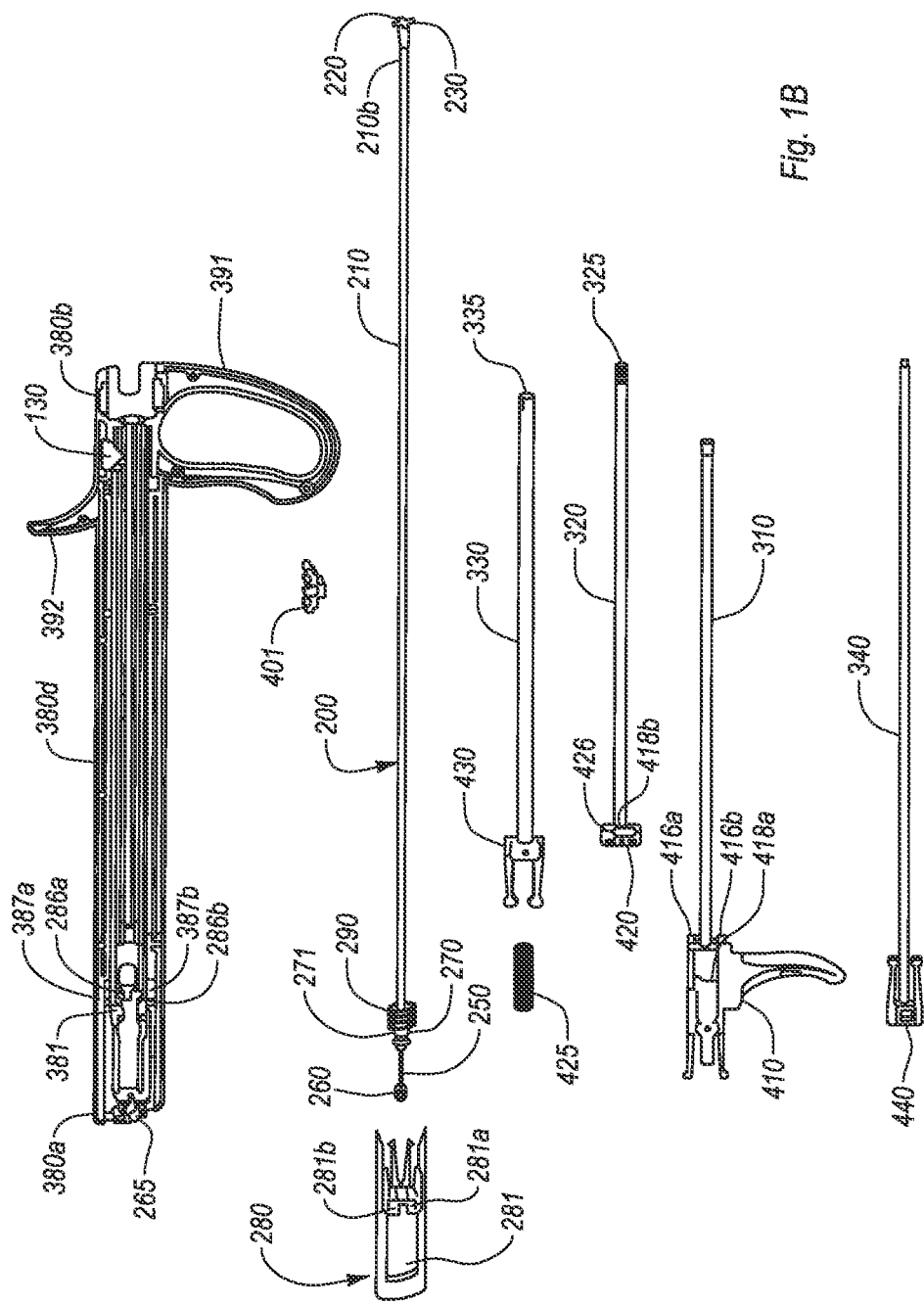
FIG. 1B illustrates another assembly view of the components of one embodiment according to the present invention for closing openings in blood vessel walls.

With continued reference to FIGS. 1A and 1B, apparatus 100 can be provided as one or more integrated components and/or discrete components that may be retained within a housing 102, having a housing top half 380*c* and a housing bottom half 380*d* (not shown). For example, apparatus 100 can include a locator assembly 110 and a carrier assembly 120. For purposes of illustration, locator assembly 110 and carrier assembly 120 are shown in FIG. 1A as including substantially separate assemblies. As desired, however, locator assembly 110 and carrier assembly 120 each can be provided, in whole or in part, as one or more integrated assemblies.

Turning to FIGS. 1A-2, 4, and 6, the assembly 110 can include a locator assembly 200. This locator assembly 200 can include flexible or semi-rigid tubular body 210 (such as an elongate rail) with a longitudinal axis. Tubular body 210 can have a proximal end region 210*a* and a distal end region 210*b* and can include a predetermined length and a predetermined outer cross-section, both of which can be of any suitable dimension. Distal end region 210*b* of locator assembly 200, as shown in more detail in FIGS. 3B and 3C, can include a substantially rounded, soft, and/or flexible distal end or tip 220 to facilitate advancement and/or retraction of distal end region 210*b* into a blood vessel or other opening in tissue. As desired, a pigtail (not shown) may be provided on tip 220 to further aid atraumatic advancement of distal end region 210*b*.

Distal end region 210*b* of locator assembly 200 is selectably controllable between an unexpanded state, as shown in FIG. 3B, and an expanded state, as shown in FIG. 3C. As shown in FIG. 3B, when an expansion end 230 is in an unexpanded state, substantially flexible members 232 are substantially axially aligned with locator assembly 200. Alternatively, when expansion end 230 is in an expanded state, substantially flexible members 232 are flexed outward.

Returning to FIG. 1B, a control member 250, such as a rod, wire, or other elongate member, may be moveably disposed within a lumen (not shown) formed by tubular body 210 and extending substantially between the proximal end region 210*a* and distal end region 210*b*. Control member 250 may have proximal end region 250*a* coupled with a control block 260, and a distal end region (not shown) of control member 250 coupled with distal end region 210*b* of locator assembly 200, expansion end 230, and/or the movable end regions of substantially flexible members 232. Control block 260 may be formed of a metal or rigid plastic in a tubular shape, and may be adapted to be retained in control block cavity 265 formed on the internal surface of housing bottom half 380*d*, to thereby maintain control block 260 in a substantially fixed position relative to the housing 380. By moving tubular body 210 axially relative to control member 250, the distal end region 210*b*, expansion end 230, and/or the substantially flexible members 232 (FIG. 3B), are selectively transitioned between the unexpanded and expanded states.

With reference to FIG. 3A, a tubular body block 270 having proximal groove 271 may be formed on proximal end 210a of tubular body 210. Tubular body block 270 may be formed of metal, rigid plastic, or other substantially rigid material and may be formed integrally with or attached securely to tubular body 210. Proximal groove 271 and the proximal end of tubular body block 270 may have a shape adapted to cooperate with a pair of tabs 279a, 279b formed on a locator assembly block 280, whereby tubular body block 270 may be maintained in a fixed axial relationship with the locator assembly block 280. In this way, tubular body block 270 and tubular body 210 (FIG. 1B) may advance distally by distal advancement of locator assembly block 280.

A locator assembly spring 290 may be located coaxially with and may substantially surround a portion of tubular body block 270. Locator assembly spring 290 may be located between and in contact with the distal side of two of tabs 279a, 279b formed on locator assembly block 280 and the proximal side of locator assembly spring stop 381 formed on the inner surface of housing bottom half 380d. The locator assembly spring 290 so located may provide a force biasing to locator assembly block 280 in the proximal direction relative to housing 380.

Locator assembly block 280 may be formed of metal, plastic, or other rigid material. A function of locator assembly block 280 may be to allow a user to apply a force causing distal movement of tubular body 210 (FIG. 1) relative to control member 250 causing locator assembly 200 (FIG. 2) to transition from the unexpanded state to the expanded state. Slot 281 may be formed in the proximal end of locator assembly block 280. Slot 281 may have a size sufficient to accommodate control block 260 and control block cavity 265, and to allow locator assembly block 280 to travel axially relative to housing 380. As shown in FIG. 1, the distal end of locator assembly block 280 may include a pair of distally extending legs 282a-b, with each of legs 282a-b having a ramp 283a-b on its inward facing surface. Finally, the locator assembly block 280 may have a pair of distally extending release tabs 284a-b, each of release tabs 284a-b having a detent 285a-b.

As shown in FIGS. 2-3A, locator assembly block 280 may be slidably received and retained within grooves formed in the proximal end of housing 380, with the proximal end of locator assembly block 280 extending from the proximal end of housing 380. Control block 260 and control block cavity 265 may be located in slot 281 formed in the proximal end of locator assembly block 280.

To release locator assembly 200, and enable it to slidably move within the grooves formed in the proximal end of the housing 380 and allow locator assembly 200 to transition from its expanded state to its unexpanded state, the apparatus 100 can include a locator release system 490 (FIG. 1A). Turning to FIG. 1A, locator release system 490 of the apparatus 100 may include locator release rod 491 having release tab spacer block 492 formed on its proximal end. Locator release rod 491 and release tab spacer block 492 may be received and retained in a groove formed on the interior surface of housing bottom half 380d. Release tab spacer block 492 may be integrally formed with or attached to the proximal end of locator release rod 491 and may be formed of metal, plastic, or other rigid material. Release tab spacer block 492 may have a shape and size adapted to fit between release tabs 284a-b formed on locator assembly block 280, thereby biasing release tabs 284a-b outward and causing outward facing detents 285a-b to engage retaining grooves 286a-b (FIG. 1B) formed on the interior of housing 380. As long as detents 285a-b are thus engaged with retaining grooves 286a-b in housing 380, locator assembly block 280 is held in an axial position against the spring force imparted in the proximal direction by locator assembly spring 290.

With continued reference to FIG. 1A, the distal end of locator release rod 491 may have an engagement member 493 that has an inward bend on the distal end of locator release rod 491. As described more fully below, engagement member 493 on locator release rod 491 may be positioned within the apparatus 100 such that when closure element 500 is delivered, engagement member 493 is engaged and caused to move axially in the distal direction, thereby disengaging release tab spacer block 492 from locator assembly block 280 and causing locator assembly 200 simultaneously to transition from an expanded state to an unexpanded state.

Returning to FIG. 1A, the carrier assembly 120 may be coupled with, and slidable relative to, locator assembly 200. Carrier assembly 120 may be configured to receive and retain closure element 500, which may be disposed substantially within carrier assembly 120. Carrier assembly 120 may be further configured to position closure element 500 substantially adjacent to an opening to be closed, and to deploy closure element 500. Upon being deployed, closure element 500 can maintain a reduced cross-section but may also temporarily and substantially uniformly expand beyond the natural cross-section of closure element 500. In either case, closure element 500, when deployed, can engage an amount of the blood vessel wall and/or tissue adjacent to the opening. Thereafter, closure element 500 may be configured to return to the natural cross-section, optionally substantially uniformly, such that the blood vessel wall and/or tissue are drawn substantially closed and/or sealed.

As shown in FIG. 1A, carrier assembly 120 may include a tube set 305 of at least one tubular member. For instance, the illustrated tube set can include carrier member 310, pusher member 320, cover member 330, and support member 340, also shown in FIG. 8. Carrier member 310, pusher member 320, cover member 330, and support member 340 may be provided as a plurality of nested, telescoping members with a common longitudinal axis. Carrier member 310 may be configured to receive and support closure element 500. While being disposed on carrier member 310, closure element 500 may be deformed from the natural, planar configuration to form a substantially tubular closure element 500", as shown in FIGS. 14A-14G, and as described herein.

Returning to FIG. 1A, carrier member 310 may include a proximal end region (not shown) and distal end region (not shown). Carrier member 310 may also define lumen 314, which may extend substantially between the proximal end region and distal end region of the carrier member 310 and configured to slidably receive at least a portion of tubular body 210 of locator assembly 200 and/or support member 340. Although the exterior cross-section of the carrier member 310 may be substantially uniform, the distal end region of carrier member 310 may have a cross-section that increases distally, as illustrated in FIG. 1A, for substantially uniformly expanding substantially tubular closure element 500 (FIG. 14G) beyond natural cross-section 530 (FIG. 14A) of closure element 500" when substantially tubular closure element 500" is deployed. Alternatively, distal end region of carrier member 310 may be formed with a uniform cross-section to deploy closure element 500 without cross-sectional expansion.

Pusher member 320 may have proximal end region (not shown) and distal end region (not shown). Pusher member 320 may be coupled with, and slidable relative to, carrier member 310. Pusher member 320 may include a predetermined length and a predetermined cross-section, both of which can be of any suitable dimension and can be configured to slidably receive carrier member 310 such that distal end region of pusher member 320 may be offset proximally from distal end region of carrier member 310. As desired, the predetermined length of pusher member 320 may be substantially equal to a predetermined length of carrier member 310. A predetermined length of pusher member 320 may be less than a predetermined length of carrier member 310 such that carrier member 310 and pusher member 320 may at least partially define a space 360 (FIG. 8) distal to distal end region of pusher member 320 and along the periphery of carrier member 310.

Pusher member 320 may be substantially tubular and can define a lumen 324 that may extend substantially between proximal end region of pusher member 320 and distal end region of pusher member 320 and configured to slidably receive at least a portion of the carrier member 310. The cross-section of pusher member 320 may be substantially uniform and distal end region of pusher member 320 can include one or more longitudinal extensions 325, which may extend distally from pusher member 320 and along the periphery of carrier member 310. Longitudinal extensions 325 may be biased such that longitudinal extensions 325 extend generally in parallel with the common longitudinal axis of carrier assembly 120. Longitudinal extensions 325 may be sufficiently flexible to expand radially, and yet sufficiently rigid to inhibit buckling as distal end region of pusher member 320 is directed distally along carrier member 310 and engages the distally-increasing cross-section of distal end region of carrier member 310 to deploy closure element 500.

Cover member 330 may be configured to retain closure element 500, in its generally tubular configuration, substantially within the carrier assembly 120 prior to deployment. Being coupled with, and slidable relative to, pusher member 320, cover member 330 has proximal end region (not shown) and distal end region (not shown), a predetermined length and a predetermined cross-section, both of which can be of any suitable dimension. Cover member 330 may be formed as a substantially rigid, semi-rigid, or flexible tubular member with an inner periphery and an outer periphery, and may define a lumen 334. Lumen 334 may extend substantially between proximal and distal end regions of cover member 330 and may be configured to slidably receive at least a portion of pusher member 320. When cover member 330 is properly positioned within carrier assembly 120, as schematically illustrated in FIG. 15A, distal end region may be configured to extend over the space 360, thereby defining annular cavity 370 for receiving and retaining substantially tubular closure element 500".

Figure 8:
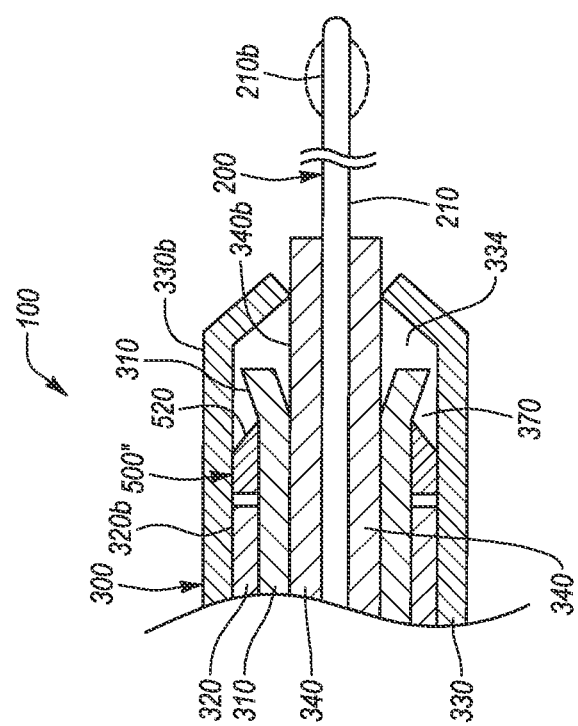
FIG. 8 illustrates a cross-sectional schematic view of the distal end of the apparatus shown in FIG. 4 as assembled for deployment.

The cross-section of cover member 330 may be substantially uniform, and distal end region of cover member 330 may include one or more longitudinal extensions 335, which extend distally from cover member 330 and along an outer periphery of pusher member 320, as shown in FIG. 8. Although longitudinal extensions 335 can extend generally in parallel with the longitudinal axis of the tube set 305, longitudinal extensions 335 may be biased such that the plurality of longitudinal extensions 335 extend substantially radially inward. Thereby, longitudinal extensions 335 may at least partially close lumen 334 substantially adjacent to distal end region of cover member 330.

Figure 15A:
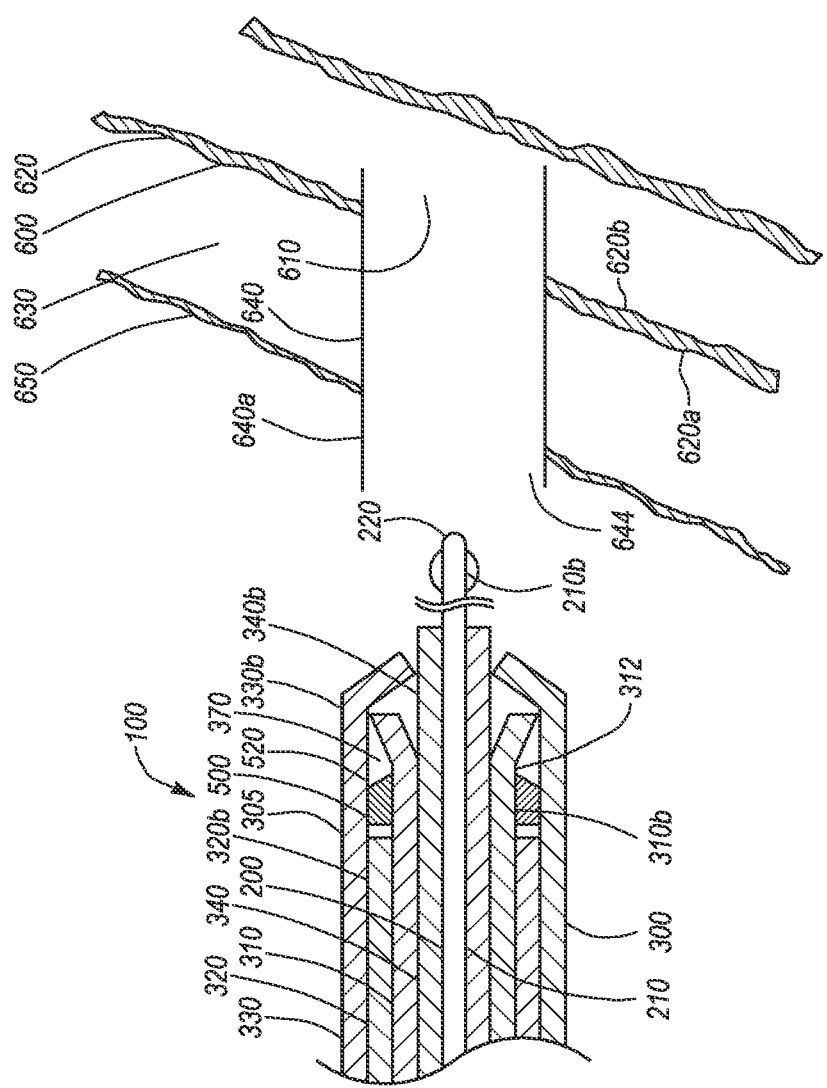

With reference to FIGS. 1B and 15A, to permit closure element 500 to be deployed from annular cavity 370, longitudinal extensions 335 may be sufficiently flexible to expand radially to permit distal end region 310b of carrier member 310 to move distally past cover member 330 to open annular cavity 370 such that distal end region of cover member 330 no longer extends over the space 360.

When carrier assembly 120 is assembled as a plurality of nested, telescoping members, as shown in FIGS. 2 and 8, carrier member 310 is at least partially disposed within, and slidable relative to, a lumen of pusher member 320, and support member 340 is slidably relative to pusher member 310. Pusher member 320, in turn, is at least partially disposed within, and slidable relative to, lumen 334 of cover member 330. To couple carrier assembly 120 with locator assembly 200, tubular body 210 of locator assembly 200 may be at least partially disposed within, and slidable relative to, lumen 314. The longitudinal axis of locator assembly 200 may be substantially in axial alignment with the common longitudinal axis of carrier member 310, pusher member 320, and cover member 330.

The apparatus 100 may also include support member 340 as shown in FIG. 1A. Support member 340 may be configured to slidably receive tubular body 210 of locator assembly 200 and provide radial support for distal end region 210b of tubular body 210 when locator assembly 200 is coupled with the carrier assembly 120. Carrier assembly 120 can advantageously include support member 340, for example, if tubular body 210 is not sufficiently rigid or under other circumstances in which support for tubular body 210 might be desirable. It also will be appreciated that support member 340 may also be configured to inhibit longitudinal extensions 335, which extend from distal end region of cover member 330, from expanding prematurely when closure element 500 is deployed. If longitudinal extensions 335 were to expand prematurely, they may become hung up on an introducer sheath or other delivery member (if an introducer sheath or delivery member is used), the tissue, or the wall of the blood vessel. This may interfere with the proper advancement or other movement of cover member 330 and carrier assembly 120.

Support member 340 may be formed as a substantially rigid, semi-rigid, or flexible tubular member, and may include proximal end region 340a and distal end region 340b. Having an outer periphery, support member 340 may define lumen 344, extending substantially between proximal end region 340a and distal end region 340b and configured to slidably receive and support at least a portion of tubular body 210 of locator assembly 200. Support member 340, in turn, can be at least partially slidably disposed within lumen 314 of carrier member 310 such that tubular body 210 of locator assembly 200 is coupled with, and slidable relative to, carrier member 310 in the manner described in more detail above.

Support member 340 may have a predetermined length and a predetermined cross-section, both of which can be of any suitable dimension, and may have a substantially uniform cross-section. Although shown and described as being substantially separate for purposes of illustration, it will be appreciated that carrier member 310, pusher member 320, cover member 330, and/or support member 340 may be provided, in whole or in part, as one or more integrated assemblies.

With reference to FIG. 8, support member 340 may also include a distal end that is blunt, rounded and/or includes a radius or curved portion that may prevent and/or eliminate damage to tubular body 200 as tubular body is moved with respect to support member 340. In some cases during deployment, as discussed in more detail below, tubular body 200 may be inserted into a lumen of an introducer at such an angle as to require tubular body 200 to flex with respect to tube set 305 as much as between about 0 degrees and 90 degrees, preferably between about 10 degrees and 90 degrees and more preferably between 30 degrees and 60 degrees, for example when used in conjunction with a femoral artery. The above-described distal end of the distal end region 340b prevents and/or eliminates damage to tubular body 200 that may result from a sharp edge pressed along tubular body 200 during advancement of tube set 305, and more particularly, support member 340 and the distal end of the distal end region 340b.

Illustratively, the radii of the distal end of the support member 340 can have various sizes and configurations. In one configuration, the distal end radii can be about 0.002 inches. In still another configuration, the distal end radii can be about 0.004 inches. In still another configuration, the distal end radii can be about 0.002 inches or greater. Increasing the radii of the distal end of support member 340 to about 0.004 inches, for instance, can decrease the amount of force required to overcome a bend in locator assembly 200 over those devices having a distal end radii of about 0.002 inches. This is because the larger radius on the distal end of the support member 340 may decrease the chance of the support member cutting into the tubular body 210 of the locator assembly 200.

In addition to the above, with the distal end having a radii greater than 0.002 inches, such as but not limited to 0.004 inches, there is a decrease in the possibility that the support member 340 may cut or otherwise damage the locator assembly 200 during positioning of the distal end of the apparatus 100 and subsequent deployment of the closure element 500. Further, a radii greater than 0.002 inches, such as but not limited to 0.004 inches, may not increase the forces used to split an introducer sheath and may not elongate the introducer sheath during positioning and deploying of the closure element 500.

With reference to FIGS. 1A and 1B, carrier assembly 120 may also include a portion of housing 380. For instance, the carrier assembly 120 can optionally include the top half 380c of housing 380, illustrated in FIG. 1A, and the bottom half 380d is shown in FIG. 1B. It will be understood, however, that housing 380 may be separate from the carrier assembly 120, while retaining and/or receiving all or a portion of the carrier assembly 120.

Housing 380 may be formed as an elongate member with a longitudinal axis, a periphery and may include proximal end region 380a and distal end region 380b. Thereby, when apparatus 100 is assembled, tubular body 210 of locator assembly 200 may be at least partially disposed within, and slidable relative to, tube set 305 such that distal end region 210b of tubular body 210 extends beyond distal end regions of the tube set 305. Tubular body 210, carrier member 310, pusher member 320, cover member 330, and, if provided, support member 340 may be at least partially disposed within, and slidable relative to, housing 380. The proximal end region 210a of tubular body 210 and the proximal end regions of tube set 305 can be at least partially disposed within, and slidable relative to, housing 380. The distal end regions of the tubular body 210 and the tube set 305 may extend from distal end region 380b of housing 380 such that common longitudinal axis (not shown) of tube set 305 may be substantially axially aligned with longitudinal axis (not shown) of housing 380. When configured to slidably retain respective proximal end regions of the tubular body 210 and the tube set 305, housing 380 supports tube set 305 and can have one or more handles 391, 392 to facilitate use of apparatus 100. Handles 391, 392 may extend, optionally substantially radially, from the outer periphery of housing 380 and can be provided as illustrated or in any manner known in the art.

To facilitate deployment of the closure element 500, the apparatus 100 can include a triggering system 400, shown in FIG. 2, which cooperates with a portion the locator assembly 200. For instance, a portion of locator assembly 200 and a portion of triggering system 400 may cooperate and be accessible externally to housing 380, as shown in FIGS. 1A and 1B. As shown in FIGS. 1A, 1B, 4-7, triggering system 400 of apparatus 100 may be disposed substantially within housing 380. Triggering system 400 may be configured to control the relative axial movement and/or positioning of distal end regions of the tube set 305 and/or locator assembly distal end region 210b. Axial motion of one or more of carrier member 310, pusher member 320, cover member 330, and support member 340 and/or tubular body 210 may be attained, for example, by applying an axial force to triggering extension 405.

Triggering system 400 may include a set of block members including carrier block 410, pusher block 420, cover block 430, and support block 440, each of which may be formed integrally with or securely attached to its respective member of carrier assembly 120. The block members may be adapted to selectably couple and decouple carrier member 310, pusher member 320, cover member 330, and support member 340 relative to one another in order to provide axial movement of those components in a predetermined manner intended to deliver closure element 500 in the manner described herein. For example, when carrier assembly 120 reaches a first predetermined distal position, support member 340 may be decoupled from carrier member 310, pusher member 320, and cover member 330, and may be thereafter substantially inhibited from further axial movement. Thereby, carrier member 310, pusher member 320, and cover member 330 may be directed distally as support member 340 remains substantially stationary. Subsequently, carrier member 310 and cover member 330 can be decoupled from pusher member 320 and thereby inhibited from further axial movement. Pusher member 320 may be directed distally as support member 340, carrier member 310, and cover member 330 remain substantially stationary, as described more fully herein.

Carrier block 410 may be disposed on proximal end region of carrier member 310 and may include trigger extension 405, which extends through a slot in housing 380 to the exterior of housing 380, accessible by a user. This carrier block 410, as shown in FIG. 3A, may include a pair of grooves 413a-b, which may be formed on a peripheral surface of carrier block 410. These grooves 413a-b may be adapted to receive and retain a pair of tabs 445a-b formed on a pair of legs 444a-b extending distally from support block 440, thereby selectably coupling support block 440 to carrier block 410. Carrier block 410, as illustrated in FIG. 1A, may also include a pair of distal tabs 416a-b extending from the distal end of carrier block 410, and adapted to engage a pair of slots 423a-b formed on the proximal end of pusher block 420.

As shown in FIGS. 1A and 3A, carrier block 410 may also include a pair of arms 414a-b extending in the proximal direction from the proximal end of carrier block 410, each of arm 414a-b having an outward directed tab 415a-b at its proximal end. The tabs 415a-b may be adapted to selectably engage a pair of slots 387a-b (FIG. 1B) formed on the interior surface of housing 380 near its proximal end and, when so engaged, to fix the axial position of carrier block 410 and, with it, carrier assembly 120 relative to housing 380. The tabs 415*a-b* may be disengaged from slots 387*a-b* FIG. 1B) in housing 380 when locator assembly block 280 is moved axially in the distal direction in the following manner. As locator assembly block 280 is advanced distally, the interior surfaces of the ramps 283*a-b* on locator assembly block legs 282*a-b* engage the exterior surfaces of tabs 415*a-b* and cause carrier block arms 414*a-b* to flex inward, releasing tabs 415*a-b* from the slots 387*a-b* in the housing, thereby freeing carrier block 410 and carrier assembly 120 to move axially. Thus, axial movement of carrier block 410 within apparatus 100 may be inhibited until locator assembly block 280 is advanced to transition locator assembly 200 to the expanded condition, simultaneously releasing tabs 415*a-b* on carrier block 410.

Pusher block 420 may be disposed on proximal end region of pusher member 320. As described above, pusher block 420 may include a pair of slots 423*a-b* formed on its proximal end, and adapted to selectably engage distal tabs 416*a-b* extending from the distal end of carrier block 410. Pusher block 420 may also include a pair of grooves 424*a-b* formed on its peripheral surface, the grooves 424*a-b* being adapted to engage a pair of tabs 435*a-b* formed on a pair of forks 434*a-b* extending from the proximal side of cover block 430 to selectably couple cover block 430 to pusher block 420.

Cover block 430 may be disposed on proximal end region of cover member 330. As described above, cover block 430 may include a pair of forks 434*a-b* extending from the proximal end of the cover block 430, each of forks 434*a-b* having an inward directed tab 435*a-b* adapted to engage grooves 424*a-b* on the peripheral surface of pusher block 420 to selectably couple cover block 430 to pusher block 420.

Support block 440 may be disposed on proximal end region 340*a* of support member 340. As described above, support block 440 may include a pair of legs 444*a-b* extending from the distal end of the support block 440, each of legs 444*a-b* having an inward directed tab 445*a-b* adapted to engage grooves 413*a-b* formed on the surface of carrier block 410 to selectably couple support block 440 to carrier block 410.

Carrier block 410, pusher block 420, cover block 430, and support block 440 are shown in FIGS. 2, 3A, 4-5 in their fully coupled state, with support block 440 coupled to carrier block 410, pusher block 420 coupled to carrier block 410, and cover block 430 coupled to pusher block 420. In this arrangement, carrier assembly 120 may include a coaxial set of tubes as shown in FIG. 8, with support member 340 slidably retained substantially within carrier member 310, which is in turn slidably retained substantially within pusher member 320, which is in turn slidably retained substantially within cover member 330.

Triggering system 400 of apparatus 100 may include an energy storing element that is used in the final stage of closure element 500 delivery processes. The energy storing element, such as, but not limited to, a spring, such as pusher spring 425 shown in FIGS. 1A, 1B, 6 and 7, may be substantially retained in a spring cavity 417 formed in carrier block 410 and coaxially surrounds a proximal end region of carrier member 310. Pusher spring 425 is capable of expanding and contracting, storing potential energy as it is contracted and releasing energy as it expands. In its fully expanded state, the pusher spring 425 has a length that is greater than the length of spring cavity 417. The cross-sectional dimension of pusher spring 425 may be such that it backs up against and contacts the proximal end of pusher block 420. Thus, when pusher spring 425 is in place between carrier block 410 and pusher block 420, pusher spring 425 is capable of imparting a force biasing carrier block 410 away from pusher block 420.

Prior to delivery of closure element 500, the distal end of carrier block 410 may be in physical contact with the proximal end of pusher block 420. In this pre-delivery condition, pusher spring 425 is in a contracted state and may be maintained within spring cavity 417. A catch member 418 serves the function of maintaining the carrier block 410 and pusher block 420 in the pre-delivery condition against the spring force of pusher spring 425, the force of which would otherwise force apart carrier block 410 from pusher block 420. Catch member 418 may be a U-shaped piece of metal, plastic, or other rigid material that engages first groove 419*a* formed on the surface of carrier block 410 and second groove 419*b* formed on the surface of pusher block 420. With reference to FIGS. 1A and 1B, pusher block 420 includes hole 426 extending through a portion thereof, with one end of hole 426 opening into groove 419*b*. Hole 426 is adapted to receive trip pin 427. During the closure element deployment process, trip pin 427 is advanced through hole 426, where it encounters catch member 418 retained in the groove 419*b*. Further advancement of trip pin 427 causes catch member 418 to become disengaged from groove 419*b*, thereby releasing the force of pusher spring 425.

The operation of the triggering system 400 of the apparatus 100 is illustrated in FIGS. 2-8 with the closure element 500 disposed substantially within the apparatus 100. As shown in FIGS. 2-3B, apparatus 100 has an initial position in which locator assembly block 280 is extended proximally and triggering system 400 is in its most proximal position. Accordingly, the locator assembly 200 is in its unexpanded state, as shown in FIG. 3B. At a point in time that the distal end region 210*b* of the locator assembly 200 has been positioned as desired (for example, within the blood vessel), locator assembly block 280 may be depressed distally, as shown in FIG. 4, thereby transitioning locator assembly 200 to the expanded state, as shown in FIG. 3C, and, simultaneously, releasing triggering system 400 from the initial position (in the manner described above) such that triggering system 400 can be advanced distally within the housing 380.

Triggering system 400 can then be advanced distally within housing 380, thereby advancing tube set 305 into position adjacent the blood vessel. At a first predetermined position, shown in FIGS. 4 and 5, support block 440 may encounter a support stop (not shown) on the interior surface of housing bottom half 380*d* that inhibits support block 440 from advancing further distally. As a result, an application of additional distal force to triggering system 400 may cause support block 440 to decouple from carrier block 410. More specifically, the tabs 445*a-b* on the legs 444*a-b* of support block 440 may disengage from grooves 413*a-b* on carrier block 410. Thus, support block 440 may remain in the position shown in FIGS. 4 and 5, while carrier block 410 may advance further distally upon application of force to triggering system 400.

Turning to FIGS. 6-8, as the triggering system 400 is advanced further distally; cover block 430 may engage a cover stop on the interior surface near the distal end region 380*b* of housing 380, thereby inhibiting additional distal advancement of cover block 430. In addition, trigger extension 405 may engage handle 391 of the apparatus 100, thereby inhibiting additional distal advancement of carrier block 410.

Closure element 500 next may be deployed by releasing pusher spring 425, which may cause pusher block 420 (and, thus, pusher member 320 (FIG. 1A)) to advance distally, deploying closure element 500 in the manner described above. As previously described, pusher spring 425 may be released by disengaging catch member 418 from groove 419b on pusher block 420, thereby releasing pusher spring 425 to force the pusher block 420 and, thus, pusher member 320 distally relative to the carrier block 410. This action may cause pusher member 320 to deploy closure element 500 from within tube set 305. The catch member 418 may be disengaged from groove 419b by applying a force to a trigger 401, which, in the deployment position, may be aligned with trip pin 427 retained in pusher block 420. A trigger spring 402 may bias trigger 401 outward relative to housing 380, with a portion of the trigger 401 extending through a hole 130 (FIG. 1B) in housing 380. A user may apply an inward directed force to trigger 401 to counteract the biasing force of trigger spring 402 and force trigger 401 against the trip pin 427.

With reference to FIGS. 1A and 6, in addition to deploying closure element 500, the distal advancement of pusher block 420 may also cause locator release system 490 to activate, thereby transitioning locator assembly 200 from the expanded state to the unexpanded state. As pusher block 420 advances distally to deploy closure element 500 in the manner described above, pusher block 420 may also engage engagement member 493 of locator release system 490 and may advance locator release rod 491 distally. This action may cause release tab spacer block 492 to disengage from release tabs 284a-b on locator assembly block 280 (see FIG. 1), thereby releasing locator assembly block 280, which may return to its proximal position, causing locator assembly 200 to return to the unexpanded state. An indicator window (not shown) may be formed in housing 380 to give a visual indication that tab spacer block 492 has disengaged and that locator assembly 200 has returned to the unexpanded state. In the present embodiment, the deployment of closure element 500 and locator release actions may occur nearly simultaneously.

Referring now to FIGS. 9-13, an alternative embodiment of the apparatus is shown in accordance with the present invention. The apparatus of the alternative embodiment may be functionally similar to that of the device previously described above and shown in FIGS. 1-8 in most respects, wherein certain features will not be described in relation to the alternative embodiment wherein those components may function in the manner as described above and are hereby incorporated into the alternative embodiment described below.

Generally, the apparatus 1000 illustrated in FIGS. 9-13 can accommodate for variations in the size of the physician's hand and grip by selectively reducing the distance between the device's handle portion and a portion of the triggering system usable to deploy the closure element and/or move a carrier assembly. Advancement of a locator assembly for locating the blood vessel wall prior to deploying the closure element may at least partially advance a portion of the triggering system of the apparatus including a trigger extension graspable by a physician or clinician. This partial movement may reduce the gap or throw between the trigger extension and the handle portion. In this manner, a physician or clinician may not need to stretch uncomfortably to position a thumb or finger on the trigger extension, grasping the handle portion, and maintaining the device in the desired orientation relative to the tissue and/or the puncture site. Furthermore, reducing the gap or throw between the trigger extension and the handle portion may enable the physician or clinician to more effectively apply a deploying force.

Figure 9:
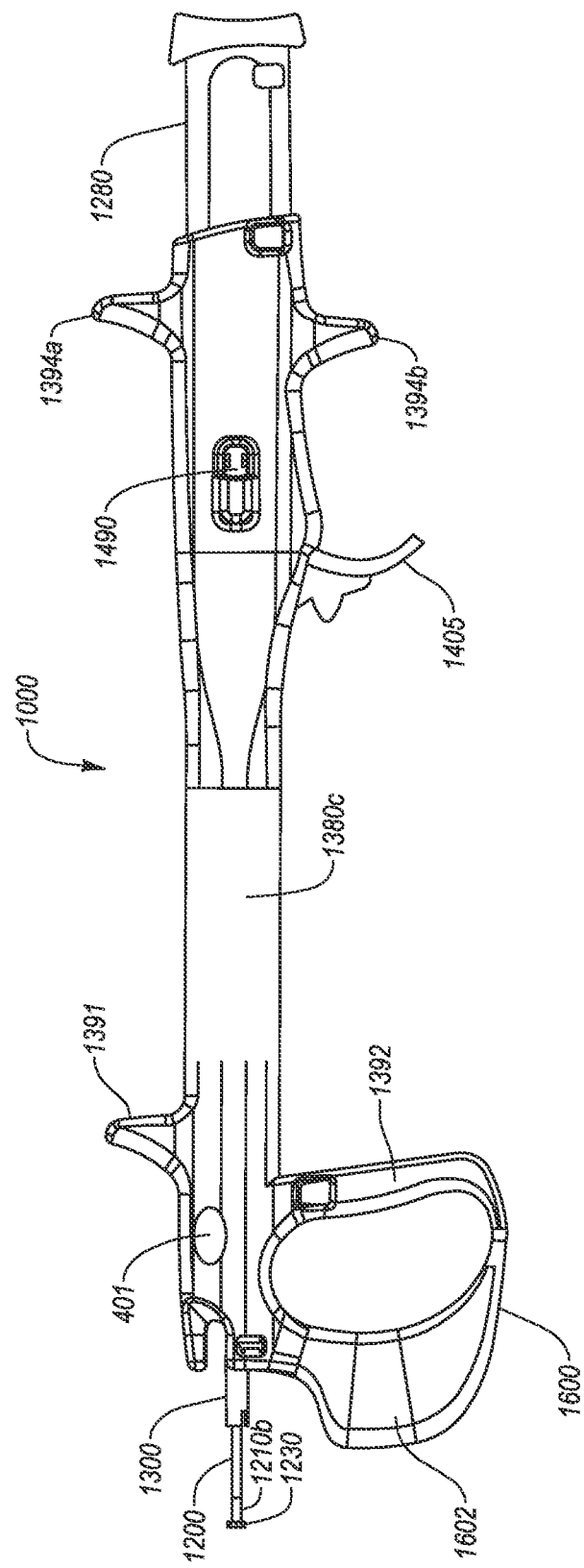
FIG. 9 illustrates a plan view of an alternative embodiment of an apparatus for closing openings in tissue in accordance with the present invention.
Figure 10:
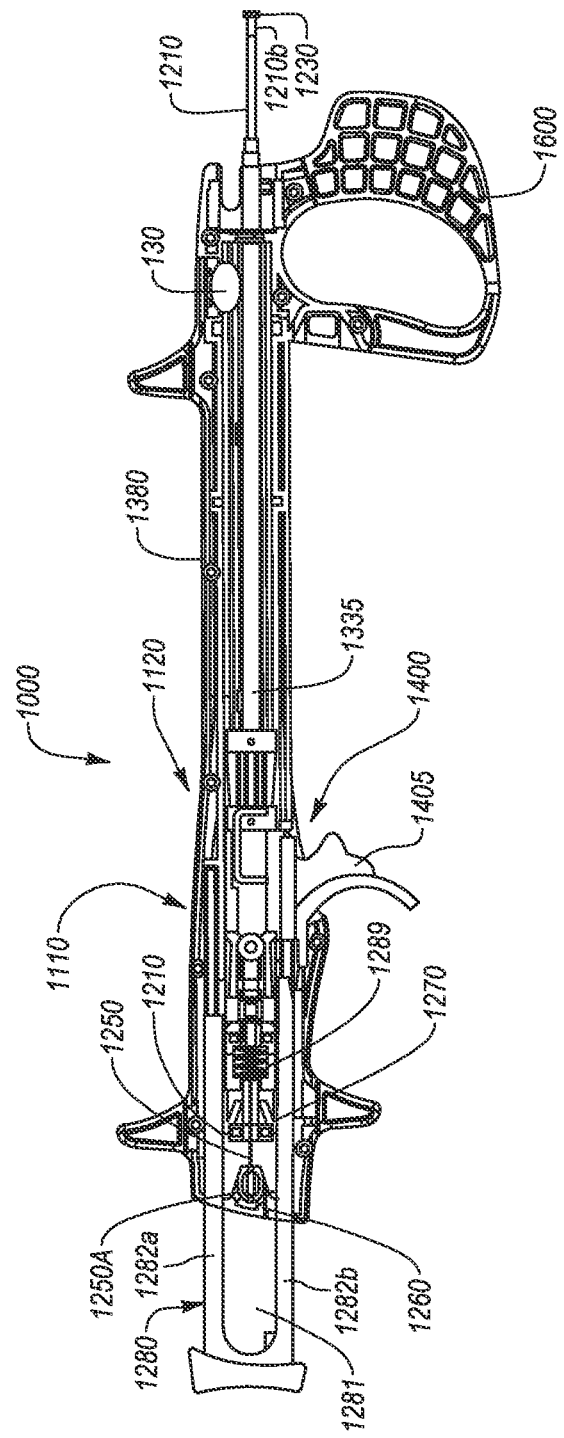
FIG. 10 illustrates a portion of a housing half of the alternative embodiment of FIG. 9, illustrating the functional components thereof.

As shown in FIG. 9, the apparatus 1000 can include a housing 1380 that may include housing halves 1380c and 1380d (FIG. 10). These housing halves 1380c and 1380d (FIG. 10), either individually or collectively, can form one or more handle, hand grip, or finger portions which a physician or clinician can grip or hold to manipulate the apparatus 1000. As illustrated, the apparatus 1000 may include finger grip 1391 and/or finger grip 1392 at a distal end and finger grips 1394a and/or 1394b on the proximal end of housing 1380 to facilitate use of locator assembly 1110, and specifically plunger 1280.

In addition, the apparatus 1000 may include handle, hand grip, and/or finger portion disposed on the distal end of housing 1380 configured to be engaged by a user when advancing housing 1380 to deploy closure element 500 (FIG. 1A). This handle, handle portion, and/or hand grip portion may include a shaped grasping portion 1600 and an elongate grasping portion 1392 spaced apart from the shaped grasping portion 1600. Each of the portions 1392 and 1600 may be contoured to be received by a user's hand. For instance, the grasping portion 1600 may provide a stable base upon which the physician or clinician can move the device or apparatus as the closure element 500 is positioned and deployed. This grasping portion 1600 may have a shaped portion 1602 with a curved configuration that can receive at least a thumb or finger of the physician or clinician as the physician or clinician holds the apparatus 1000. The curved configuration or profile may allow the physician to grasp the handle or handle grip portion while resting their hand, wrist, or forearm upon a patient during the procedure, such as deployment of the closure element 500, thereby providing stability during use of the apparatus 1000.

It will be understood that although reference is made to one particular configuration of the handle, hand grip, and/or finger portions, various other handle portion configurations may perform the function of providing a stable base for manipulation of the apparatus 1000. For instance, and not by way of limitation, the handle portion may be planar rather than curved. Further, the handle portion may include one or more finger receiving holes. In addition, the handle portion may include a material to provide cushioning or comfort to the physician and/or clinician. For example, flexible, yielding, and/or elastic materials may be formed or applied to all or a portion of the handle portion.

Referring now to FIGS. 9 and 10, apparatus 1000 may be provided as one or more integrated components and/or discrete components. For instance, and not by way of limitation, apparatus 1000 may include locator assembly 1110 and/or carrier assembly 1120. For purposes of illustration, locator assembly 1110 and carrier assembly 1120 are shown in FIG. 10 as having substantially separate assemblies. As desired, however, locator assembly 1110 and carrier assembly 1120 may each be provided, in whole or in part, as one or more integrated assemblies. Portions of locator assembly 110 and/or carrier assembly 120 may also be used as part of apparatus 1000. Alternatively, modified versions of locator assembly 110 and/or carrier assembly 120 may be used.

Locator assembly 1110 may be constructed in the manner previously described above, including a flexible or semi-rigid tubular body (such as an elongate rail) with a longitudinal axis. The tubular body may have a proximal end region and a distal end region and/or may include a predetermined length and a predetermined outer cross-section, both of which may be of any suitable dimension. The distal end region of the locator assembly may include a substantially rounded, soft, and/or flexible distal end or tip to facilitate atraumatic advancement and/or retraction of the distal end region into a blood vessel or other opening in tissue. As desired, a pigtail (not shown) may be provided on the distal end to further aid atraumatic advancement of the distal end region. The distal end region of locator assembly 1110 may be selectably controllable between an unexpanded state and an expanded state.

As shown in FIG. 10, apparatus 1000 may include carrier assembly 1120 which may be functionally equivalent to carrier assembly 120 (FIG. 1A) described above and will not be described in detail with regard to the present embodiment. As with carrier assembly 120, carrier assembly 1120 may be coupled with and/or be slidable relative to locator assembly 1110. Carrier assembly 1120 may be configured to receive and retain the closure element 500 (shown in FIGS. 14A-14G), which may be disposed substantially within carrier assembly 1120. Carrier assembly 1120 may function to position closure element 500 substantially adjacent to an opening to be closed, and to deploy closure element 500.

Figure 11A:
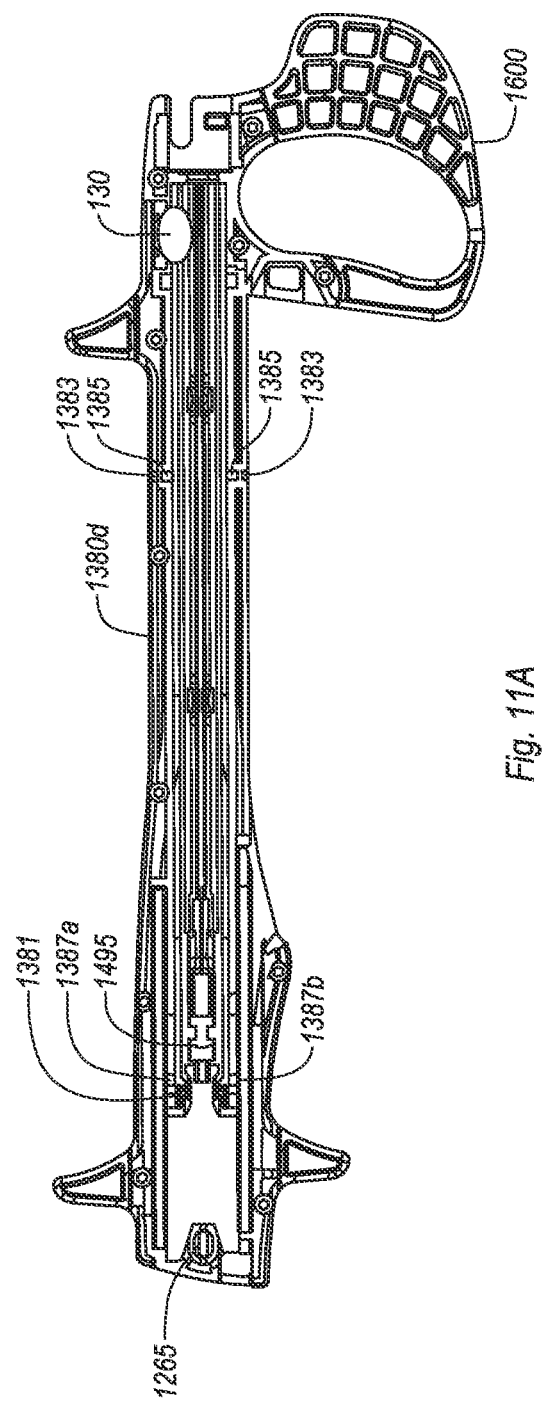
FIG. 11A illustrates a portion of a housing half of the alternative embodiment of FIG. 9, without certain functional components.

Referring now to FIGS. 10 and 11, locator assembly 1110 of the present embodiment will be described in greater detail. As with the previous locator assembly 110, a control member 1250, such as a rod, wire, or other elongate member, may be moveably disposed within a lumen (not shown) formed by tubular body 1210 and may extend substantially between the proximal end region and the distal end region of the lumen. Control member 1250 may have a proximal end region 1250a that may be coupled with a control block 1260, and a distal end region that may be coupled with the distal end region of locator assembly 1110, expansion members 1230, and/or movable end regions of substantially flexible members, such as flexible members 232 (FIG. 3B). Control block 1260 may be constructed in a tubular shape and formed of a metal or rigid plastic, and may be adapted to be retained in control block cavity 1265 (FIG. 11A) formed on the internal surface of the housing bottom half 1380d, to thereby maintain control block 1260 in a substantially fixed position relative to housing half 1380d and so housing 1380. The locator assembly 1110 may selectively transition distal end region 1210b, expansion members 1230, and/or the substantially flexible members between the unexpanded and expanded states by moving tubular body 1210 axially relative to control member 1250. Additionally, as shown in FIG. 11A, apertures 1383 may be placed adjacent to and/or in communication with detents 1385, wherein in use as described below, tabs 415a and 415b (FIG. 1A) may engage the detents 1385 during use. Apertures 1383 may be configured to receive the tip of a medical device, such as a tip of a dilator from a sheath assembly, wherein the tip of the dilator may be used to disengage the tabs 415a and 415b (FIG. 1A) from the detents 1385 thereby releasing the locked position of the device. This may enable a user to move the trigger assembly 1400 (FIG. 10) proximally (toward the user) after the clip has been deployed in the event that the device becomes stuck within the patient, thereby providing a safety release mechanism. It shall be appreciated that the apertures 1383 may be replaced by other features, such recessed buttons, that become exposed with the engagement of the tabs with the detents and/or a specific tool may be provided with the device.

With reference to FIGS. 10 and 11B, to facilitate movement of carrier assembly 1120 to reduce the distance between a trigger extension 1405 and the distal end of housing 1380, the functionality of locator assembly block 280 (FIG. 1A) may be provided through the combination of a plunger 1280, a tubular body block 1270, and a spring retainer 1290. In addition to providing the functionality of locator assembly block 280, including controlling movement of expansion members 1230, plunger 1280, tubular body block 1270, and spring retainer 1290 and/or aiding with moving trigger extension 1405 toward the distal end of housing 1380.

With reference to FIG. 11B, plunger 1280 may include two spaced apart legs 1282a-b, which may be separated by a plunger member 1284 to form a slot 1281 therebetween. The legs 1282a-b may be spaced apart sufficiently to accommodate and/or receive a portion of tubular body block 1270 and/or spring retainer 1290 therebetween. Each of the legs 1282a-b may have a stepped configuration, such as the configuration shown in FIG. 11D. Plunger 1280 may be slidably received and/or retained within grooves formed in the proximal end of housing 1380, with the proximal end of plunger 1280 extending from the proximal end of housing 1380.

Plunger 1280 may be constructed of metal, plastic, and/or other rigid materials. The proximal end of plunger 1280 may have a slot 1281 formed therein. Slot 1281 may have a size sufficient to accommodate control block 1260 and control block cavity 1265 and to allow plunger 1280 to travel axially relative to housing 1380. As mentioned, the distal end of plunger 1280 may include a pair of distally extending legs 1282a-b with optional ramps 1283a-b on respective inward facing surfaces. In addition, a recess 1285 may be formed in each leg 1282a-b within which a protrusion 1286 may move. The protrusion 1286 may have a detent 1288 that can interlock with the tubular body block 1270 and/or spring retainer 1290 as plunger 1280 is moved distally.

Figure 12:
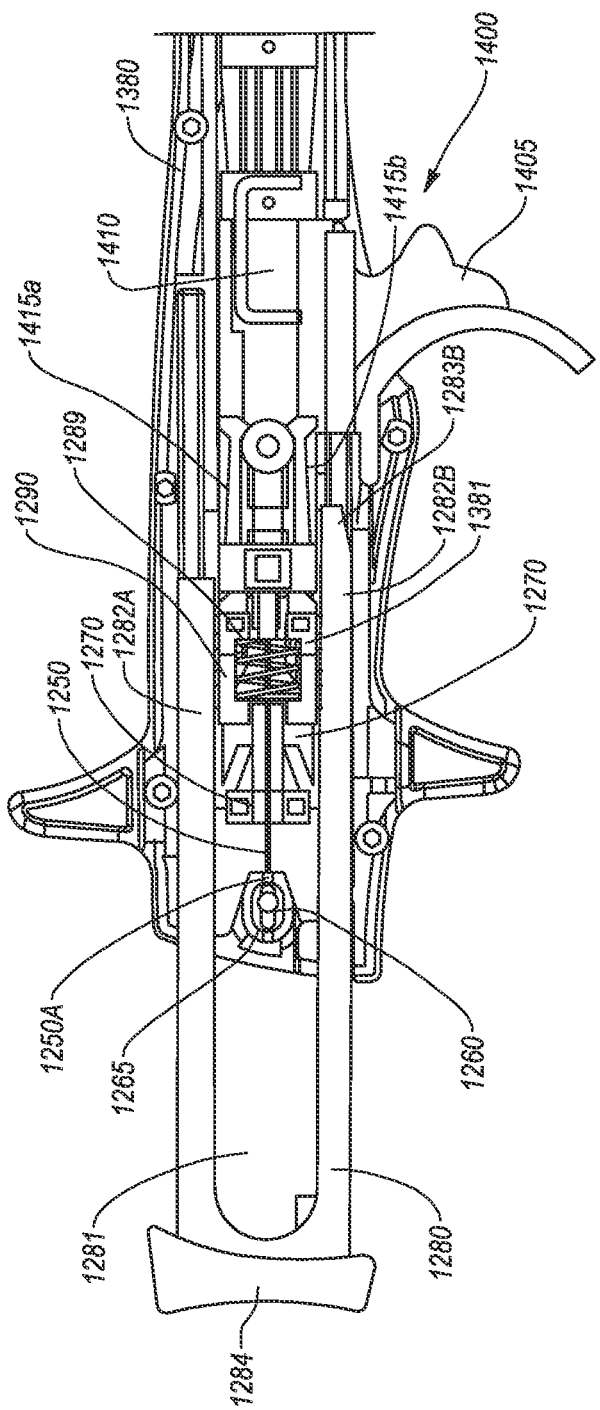
FIG. 12 illustrates a close-up cross-sectional view of the proximal end of the apparatus shown in FIG. 9, illustrating the initial position of the locator control system.

With reference to FIGS. 11B and 11E, tubular body block 1270 may be formed integrally with or attached securely to tubular body 1210. The tubular body block 1270 may include a pair of extending legs 1272a-b. Each of legs 1272a-b may have a ramp portion 1273a-b on its inward facing surface. Ramp portions 1273a-b may cooperatively engage tabs, not shown but similar to tabs 415a-b (FIG. 1A), of carrier block 1410 (FIG. 12). In an initial state, the tabs 415a-b (FIG. 1A) may be engaged in slots 1387a-1387b (FIG. 11A) formed in housing half 1380d to hold triggering system 1400 (FIG. 10) in a fixed axial relationship with housing 1380.

An intermediate member 1274 may extend between legs 1272a-b. The intermediate member 1274 may include a pair of upwardly extending extensions 1276a-b and/or a tab 1278, shown in dotted lines in FIG. 11B. Extensions 1276a-b may be received within the space between legs 1282a-b of plunger 1280. Stated another way, tubular body block 1270 may be held in a fixed axial relationship with respect to plunger 1280 through the engagement of legs 1282a-b and legs 1272a-b. The tab 1278 may be adapted to cooperate with spring retainer 1290 and/or lock with a portion of spring retainer 1290 as plunger 1280 moves distally, as will be described in more detail hereinafter.

A tubular portion 1279 may extend from intermediate member 1274 in the same direction as legs 1272a-b. The tubular portion 1279 may slidably cooperate with spring retainer 1290 and may receive tubular body 1210 within a lumen. Further, tubular portion 1279 may cooperate with a locator assembly spring 1289 (FIG. 10) which may bias tubular body block 1270 and/or spring retainer 1290 relative to housing 1380.

As shown in FIGS. 11B and 11F, spring retainer 1290 may include a wall portion 1291 with a recess 1292 that may receive tubular portion 1279 of tubular body block 1270. The wall portion 1291 may define a channel 1294 within which the locator assembly spring 1289 (FIG. 10) may be received. For instance, locator assembly spring 1289 (FIG. 10) may extend from wall portion 1291 to locator assembly spring stop 1381 (FIG. 11A) to bias movement of spring retainer 1290, tubular body block 1270, and/or locator assembly 1110.

Spring retainer 1290 may further include arms 1296*a-b*. Arms 1296*a-b* may include a movable portion 1297*a-b* that may flex or move to receive tab 1278 of tubular body block 1270. For instance, tab 1278 may include curved surfaces that may cooperate and/or receive a portion of movable portion 1297*a-b* as tubular body block 1270 moves relative to spring retainer 1290. Alternatively, tab 1278 may be positioned within a space 1299 between wall portion 1291 and movable portion 1297*a-b* before manipulation or operation of apparatus 1000. It will be understood that other portions of arms 1296*a-b* can flex or move, whether or not movable portions 1297*a-b* move.

In addition to arms 1296*a-b*, spring retainer 1290 may include release tabs 1298*a-b*. These release tabs 1298*a-b* may function in a similar manner to tabs 284*a-b* (FIG. 1A). For instance, tabs 1298*a-b* may cooperate with a locator release system 1490 in a manner substantially similar to the embodiments described above. For example, release tabs 1298*a-b* may engage release cavity 1495 on housing 1380, and may be held from releasing by release tab spacer block 1492.

Generally, plunger 1280, tubular body block 1270, and/or spring retainer 1290 may be formed of metal, plastic, and/or other material, whether or not rigid, substantially rigid, or flexible. As such, plunger 1280, tubular body block 1270, and/or spring retainer 1290 may be formed from medical grade synthetic materials and/or materials that can be sterilized or otherwise cleaned.

Figure 13:
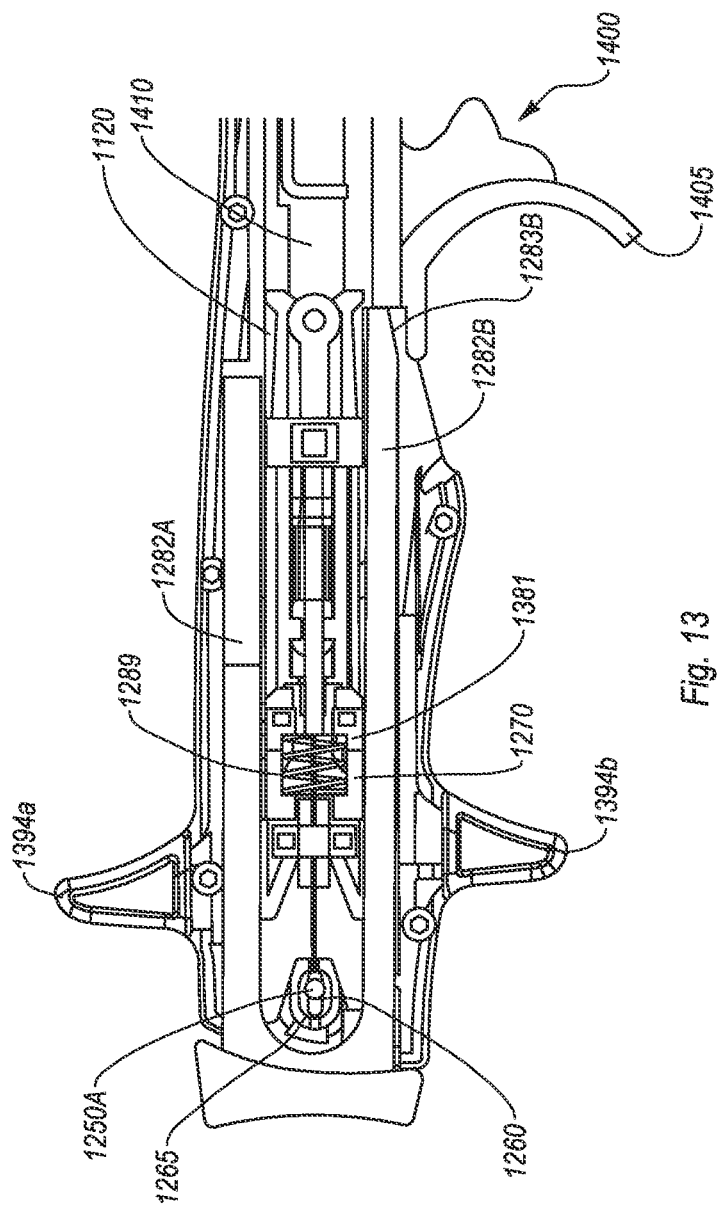
FIG. 13 illustrates a close-up cross-sectional view of the proximal end of the apparatus shown in FIG. 9, illustrating the final position before clip release of the locator control system.
Figure 14A:
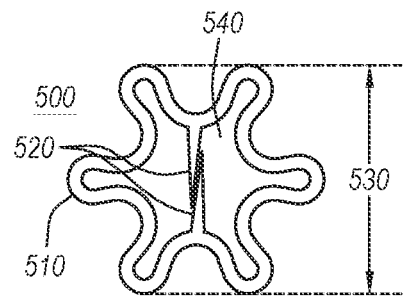
FIGS. 14A-14G illustrate various embodiments of closure elements that can be utilized with the apparatus of the present invention.
Figure 14B:
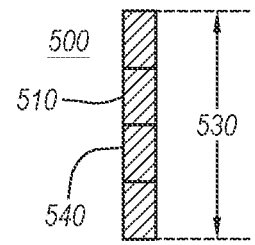
Figure 14C:
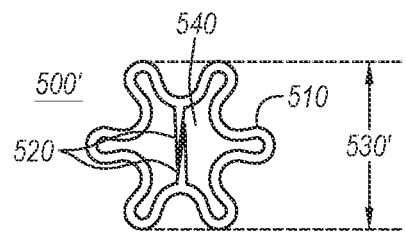
Figure 14D:
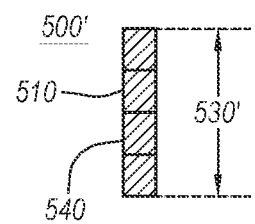
Figure 14E:
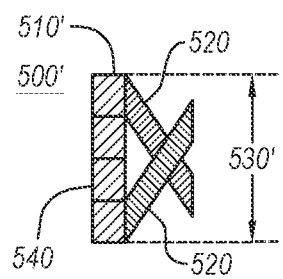
Figure 14F:
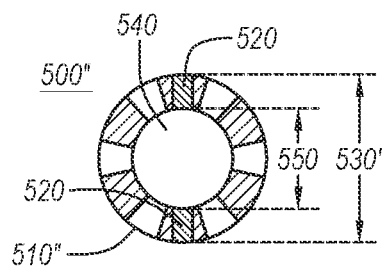
Figure 14G:
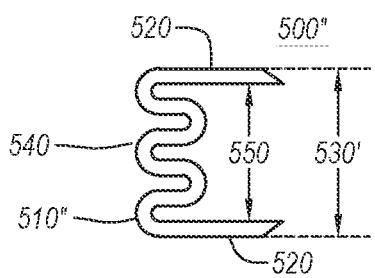

Turning now to FIGS. 12 and 13, illustrated are the operational positions of the apparatus 1000 in (i) an initial state with the expansion members 1230 (FIG. 9) in an unexpanded condition and (ii) a state with the expansion members 1230 (FIG. 9) in an expanded condition.

With reference to FIG. 12, in the initial state, plunger 1280 may extend from the distal end of housing 1380, expansion members 1230 may be in an unexpanded condition, and locator assembly spring 1289, which can be located coaxially with tubular body block 1270, may be located between spring retainer 1290 and the proximal side of locator assembly spring stop 1381 formed on the inner surface of housing bottom half 1380*d*. In this initial state, locator assembly spring 1289 may be held in a biased state. Optionally, a portion of carrier assembly 1120 (FIG. 10) may be associated with legs 1282*a-b* of plunger 1280 and contact carrier a portion of carrier assembly 1120 (FIG. 10).

Once a user presses on plunger 1280 to expand expansion members 1230, i.e. moving plunger 1280 toward expansion members 1230, tubular body block 1270 and/or tubular body 1210 may advance distally by distal advancement of plunger 1280. Upon advancement, and with reference to FIGS. 1A and 10-12, ramp members 1273*a-b* may press tabs 415*a-b*, which are hidden by plunger 1280 in FIG. 12, releasing carrier block 1410 to slide axially in housing 1380. Advancing ramp members 1273*a-b* may release tabs 1298*a-b* engaged in retaining grooves 1387*a-b* in cooperation with locator release system 1490. Locator release system 1490 may be functionally equivalent to locator release system 490 described above. Thus, advancing ramp members 1273*a-b* may thereby fix spring retainer 1290 and tubular body block 1270 axially with respect to housing 1380 and expansion members 1230 of locator assembly 1110 in an expanded state. Also during advancement, tab 1278 of tubular body block 1270 may advance between arms 1296*a-b* of spring retainer 1290. This advancement may extend the arms outwardly until tab 1278 advances past the ends of arms 1296*a-b*, which may cause arms 1296*a-b* to extend behind tab 1278, thereby coupling spring retainer 1290 and tubular body block 1270, and fixing tubular body block axially prior to activation of locator release system 1490. Once advanced, the plunger 1280, in the present embodiment, may be locked into a distal position by legs 1272*a* and 1272*b*.

Further axial movement of plunger 1280 may allow the engagement of distal end 1283*b* of leg 1282*b* and carrier block 1410, thereby moving carrier block 1410 distally along with carrier assembly 1120, as illustrated in FIG. 13. This additional movement of carrier assembly 1120 may also move trigger extension 1405, generally shortening the distance required to fully engage the carrier assembly 1120. Combining the deployment of locator assembly 1110 and the partial advancement of carrier assembly 1120 in a single step, may allow for a reduction in travel of the trigger block and trigger extension 1405. This reduction of travel may allow for a greater variation in user strength as well as the physical size of a user's hand to fit better with device 1000 as illustrated.

Once locator assembly 1110 is deployed, carrier assembly 1120 may be advanced distally by exerting force on trigger extension 1405, and may be fixed in the distal position in the manner described above with reference to other embodiments above. After the locator has been deployed and the carrier assembly initially advanced, as shown in FIG. 13, device 1000 may function in the manner described above with regard to other embodiments of the present invention and thus will not be described in detail with regard to this embodiment.

In some embodiments, the tubular body block and the release block may be integrally formed. When the tubular body block and the release block are integrally formed, axial movement of the locator assembly block may force outward movement of tabs holding the tubular body block to the locator assembly block, which may allow the integrally formed tubular body block and release block to slide distally with respect to the locator assembly block and may cause the release tabs to load the locator release system to release as discussed above.

Referring now to FIGS. 14A-14G illustrating embodiments of a closure element that can be used as part of or with the apparatus 100. The closure element, generally identified with reference numeral 500, may have a generally annular-shaped body defining a channel and one or more barbs and/or tines for receiving and engaging the blood vessel or other body lumen wall and/or the tissue around the opening. Although the closure element has a natural shape and size, the closure element can be deformed into other shapes and sizes, as desired, and can be configured to return to the natural shape and size when released. For example, closure element 500 can have a natural, planar configuration with opposing tines and a natural cross-section. The closure element can be formed from any suitable material, including any biodegradable material, any shape memory material, such as alloys of nickel-titanium, or any combination thereof. Additionally, it is contemplated that the closure element may be coated with a beneficial agent or be constructed as a composite, wherein one component of the composite would be a beneficial agent. As desired, the closure element may further include radiopaque markers (not shown) or may be wholly or partially formed from a radiopaque material to facilitate observation of the closure element using fluoroscopy or other imaging systems. Exemplary embodiments of a closure element are disclosed in U.S. Pat. Nos. 6,197,042, 6,623,510, 6,461,364, 6,391,048, and 6,719,777 and U.S. Patent Publication Nos. 2004-153122 and 2004-039414. The disclosures of these references and any others cited therein are expressly incorporated herein by reference.

It will be appreciated that the closure element may be constructed of other materials, that it may include alternative shapes, and that it may adopt alternative methods of operation such that the closure element achieves closure of openings in blood vessel walls or other body tissue. In an additional non-limiting example, the closure element is constructed of materials that use a magnetic force to couple a pair of securing elements in order to close an opening in the lumen wall or tissue. In this alternative embodiment, the closure element may be of a unitary or multi-component construction having a first securing element positionable at a first position adjacent the opening, and a second securing element positionable at a second position adjacent the opening. The first and second securing elements are provided having a magnetic force biasing the first and second securing elements together, thereby closing the opening, or they are provided having a magnetic force biasing both the first and second securing elements toward a third securing element positioned in a manner to cause closure of the opening. The magnetic closure element may be provided without tines, provided the magnetic force coupling the closure elements is sufficient to close the opening. Alternatively, the closure element may be provided with a combination of the magnetic securing elements and tines to provide a combination of coupling forces. Those skilled in the art will recognize that other and further materials, methods, and combinations may be utilized to construct the closure element to achieve the objectives described and implied herein.

As described previously, and with reference to FIG. 15A, closure element 500 may be disposed within the carrier assembly and adjacent to the distal end of pusher tube 320. As shown in FIG. 15A, for example, the reduced closure element 500 may be slidably received over distally-increasing cross-section of distal end region of carrier member 310 and may be disposed about periphery 312 of carrier member 310 adjacent to space 360. Since reduced cross-section 530 of reduced closure element 500 is less than cross-section of distally-increasing cross-section, reduced closure element 500 may be temporarily radially deformed to be received over distal end region of the carrier member 310. Also, as reduced closure element 500' (FIG. 14C) is received over distal end region of carrier member 310, opposing tines 520 of reduced closure element 500' (FIG. 14C) engage distal end region of carrier member 310. Reduced closure element 500' (FIG. 14C) may thereby form substantially tubular closure element 500", illustrated in FIG. 14G, with the ends of the barbs and/or tines extending towards the distal end of the apparatus 100.

The apparatuses of the present invention may be configured to be utilized with a sheath. The sheath may be inserted or otherwise positioned into an opening in a body having a lumen. The sheath may generally have a substantially flexible or semi-rigid tubular member having a proximal end region and a distal end region and may include a predetermined length and/or a predetermined cross-section, both of which can be of any suitable dimension. The sheath may form a lumen that may extend along a longitudinal axis of the sheath and/or substantially between the proximal and/or distal end regions. The lumen may have any suitable internal cross-section and may be suitable for receiving one or more devices (not shown), such as a catheter, a guide wire, and/or other device. The lumen may be configured to slidably receive the tubular body of the locator assembly and/or the tube set of the carrier assembly of the devices in accordance with the present invention.

Since the internal cross-section of the sheath may be less than or substantially equal to the predetermined cross-section of the cover member, the sheath may be configured to radially expand, such as by stretching, to receive the tube set. Alternatively, or in addition, the sheath may be advantageously configured to split as the tube set is received by and advances within the lumen of the sheath. This may permit the apparatuses to access the body lumen wall. To facilitate the splitting, the sheath may include one or more splits, such as longitudinal splits. Each split may be configured to split the sheath in accordance with a predetermined pattern, such as in a spiral pattern. It will be appreciated that when the internal cross-section of the sheath is greater than the predetermined cross-section of the cover member, it may not be necessary for the sheath to be configured to radially expand and/or split. In some embodiments, the apparatus may include a cutting means that initiates a tear line or split in the sheath when the sheath is engaged with the distal end of the apparatus.

The sheath may be advanced over a guide wire or other rail (not shown), which has been positioned through the opening and into the blood vessel using conventional procedures such as those described above. In some embodiments, the blood vessel may be a peripheral blood vessel, such as a femoral or carotid artery. In other embodiments, other body lumens may be accessed using the sheath. The opening, and consequently the sheath, may be oriented with respect to the blood vessel to facilitate the introduction of devices through the lumen of the sheath and into the blood vessel with minimal risk of damage to the blood vessel. One or more devices (not shown), such as a catheter, a guide wire, and/or other devices, may be inserted through the sheath and/or advanced to a preselected location within the patient's body. For example, the devices may be used to perform a therapeutic and/or diagnostic procedure, such as angioplasty, atherectomy, stent implantation, and/or other procedures, within the patient's vasculature.

FIGS. 15A-K illustrate one exemplary manner to deploy closure element 500 by apparatuses according to the present invention. For purposes of continuity, reference numbers to the first discussed embodiment are used, but it will be evident that other embodiments discussed above may be used in a similar fashion.

A sheath 640 may be inserted or otherwise positioned through a patient's skin 650 and tissue 630 and within the blood vessel 600 or other body lumen via the opening 610. This provides access to the blood vessel 600 through the blood vessel wall 620 for performance of a therapeutic or diagnostic procedure. The sheath 640 will be described in more detail below.

Figure 15B:
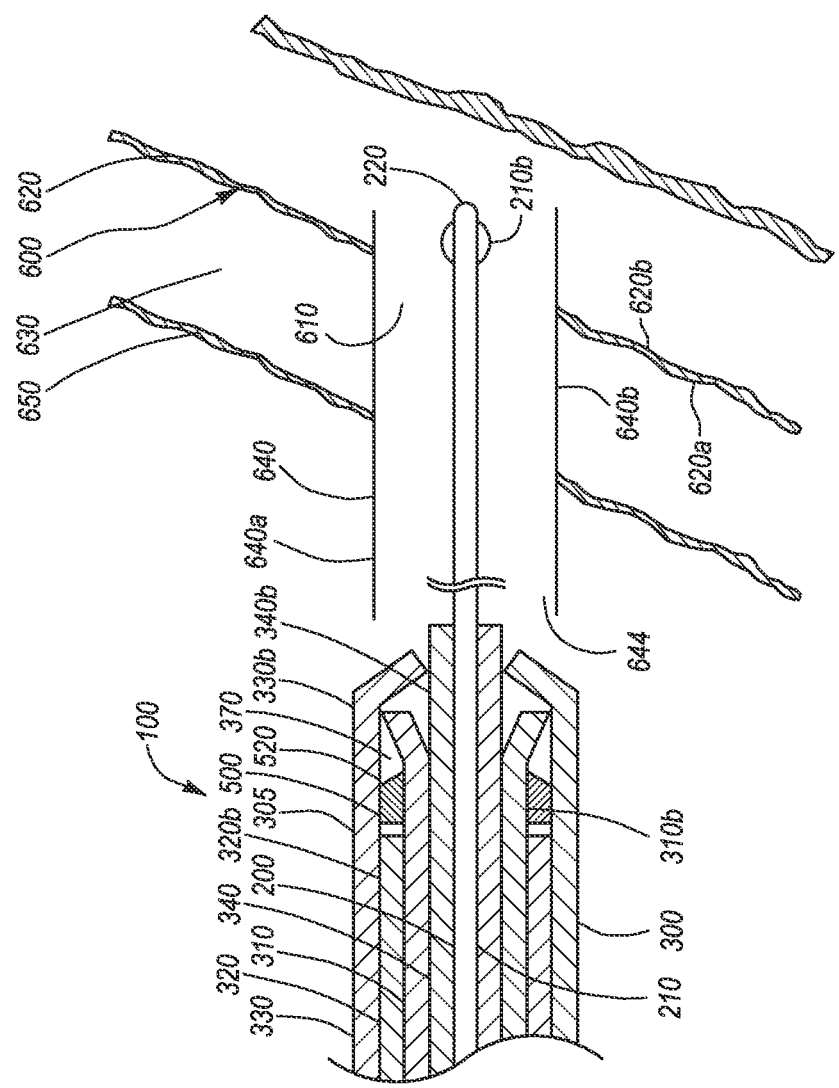

After the procedure is completed, the devices associated with the therapeutic or diagnostic procedure are removed from sheath 640, and apparatus 100 can be prepared to be received by lumen 644 of the sheath. Being in the unexpanded state, the distal end region 210b of tubular body 210 of the locator assembly 200 can be slidably received by the lumen and atraumatically advanced distally into the blood vessel 600, as illustrated in FIG. 15B. Once the distal end region 210b extends into blood vessel 600, distal end region 210b can transition from the unexpanded state to the expanded state by activating the switching system of locator assembly 200, and as illustrated in FIG. 15C. As discussed with reference to the embodiments described in reference to FIGS. 9-13, the carrier assembly may be partially advanced when the locator assembly is transitioned from the unexpanded to the expanded state by pressing the locator assembly block distally with respect to the housing.

Figure 15D:
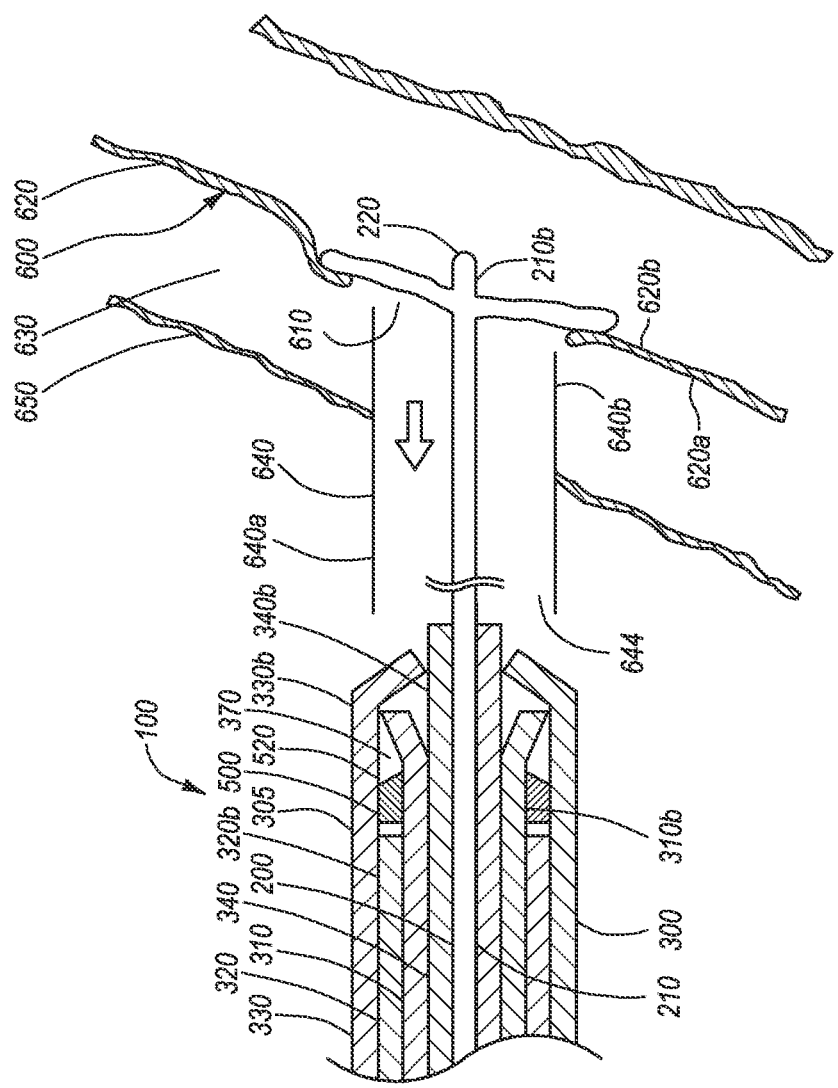

Turning to FIG. 15D, apparatus 100 and/or sheath 640 can then be retracted proximally until distal end region 210*b* is substantially adjacent to an outer surface 620*a* of blood vessel wall 620. Distal end region 210*b* thereby draws blood vessel wall 620 taut and maintains the proper position of apparatus 100 as blood vessel 600 pulsates. Since the expanded cross-section of distal end region 210*b* is greater than or substantially equal to the cross-section of opening 610 and/or the cross-section of lumen 644, distal end region 210*b* remains in blood vessel 600 and engages inner surface 620*b* of blood vessel wall 620. Distal end region 210*b* can frictionally engage inner surface 620*b* of blood vessel wall 620, thereby securing apparatus 100 to blood vessel 600. Sheath 640 can be retracted proximally such that distal end region 640*b* of sheath 640 is substantially withdrawn from blood vessel 600, permitting apparatus 100 to access blood vessel wall 620.

Figure 15F:
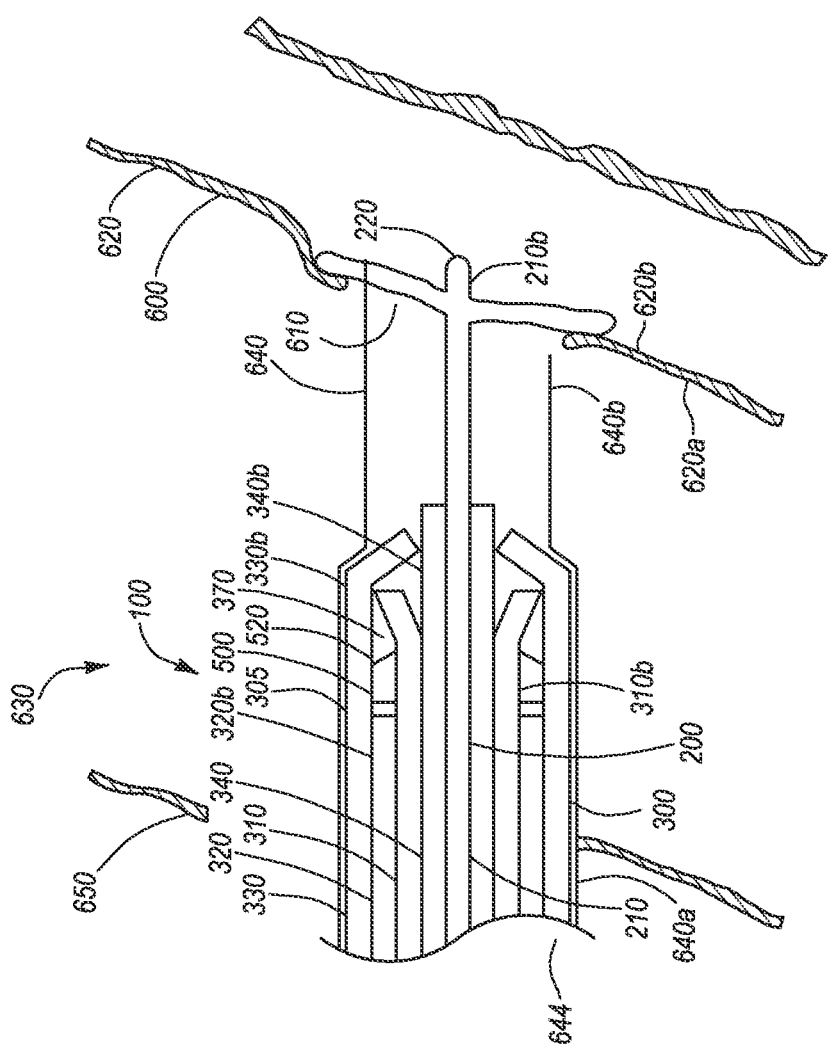

Once distal end region 210*b* of locator assembly 200 contacts inner surface 620*b* of blood vessel wall 620, tube set 305 can then be advanced distally and received within lumen 644 of sheath 640. In the manner described above, sheath 640 can radially expand and/or split in accordance with the predetermined pattern as tube set 305 advances because the internal cross-section of sheath 640 is less than or substantially equal to pre-determined cross-section 338*b* of cover member 330. Being coupled, carrier member 310, pusher member 320, cover member 330, and support member 340 each advance distally and approach the first predetermined position, as illustrated in FIG. 15F. As discussed with reference to the embodiments described in reference to FIGS. 9-13, a stable base can be provided by handle portion 1600 having an enlarged, curved configuration that can receive at least a thumb or finger of the physician. The enlarged, curved handle portion 1600 can gripped by the physician while the physician's hand is rested upon a patient during the procedure and provide stability during use of the device. Additionally, the combined deployment of locator assembly 1110 and the partial advancement of carrier assembly 1120 in a single step allows for a reduction in travel of trigger extension 1405. Thus, a user does not need to reach uncomfortably far from handle portion 1602 to trigger extension 1405 to fully advance carrier assembly 1120 and the tube set coupled to the carrier assembly.

Upon reaching the first predetermined position, tube set 305 is disposed substantially adjacent to outer surface 620*a* of blood vessel wall 620 adjacent to opening 610 such that the blood vessel wall adjacent to opening 610 is disposed substantially between expanded distal region 210*b* of locator assembly 200 and tube set 305. Support member 340 decouples from carrier member 310 and pusher member 320 in the manner described above when tube set 305 is in the first predetermined position. The cover member 330 and pusher member 320 are advanced. After advancement, the cover member 330 is decoupled from the carrier member 310 and pusher member 320. Thereby, cover member 330 and support member 340 may be inhibited from further axial movement and remain substantially stationary as carrier member 310 and pusher member 320 each remain coupled and axially slidable.

As shown in FIG. 15G, cover member 330 and support member 340 remain substantially stationary while carrier member 310 and pusher member 320 continue distally and approach the second predetermined position. As carrier member 310 and pusher member 320 distally advance toward the second predetermined position, annular cavity 370 moves distally relative to substantially-stationary cover member 330 such that distal end region 330*b* of cover member 330 no longer encloses annular cavity 370. Thereby, closure element 500 is not completely enclosed by annular cavity 370 formed by distal end regions 310*b*, 320*b*, and 330*b* of carrier member 310, pusher member 320, and cover member 330.

Although not completely enclosed by annular cavity 370, substantially tubular closure element 500 is advantageously retained on outer periphery 312*b* of carrier member 310 by distal end region 330*b* of cover member 330 as illustrated in FIG. 15G. For example, by retaining substantially tubular closure element 500 between distal end region 330*b* of cover member 330 and distal end region 310*b* carrier member 310, apparatus 100 may be configured to provide better tissue penetration. The timing between the deployment of substantially tubular closure element 500 by tube set 305 and the retraction and transition to the unexpanded state by locator assembly 200 likewise is facilitated because substantially tubular closure element 500 is retained between distal end region 330*b* and distal end region 310*b*. Further, carrier member 310 and cover member 330 operate to maintain substantially tubular closure element 500 in the tubular configuration.

Figure 15H:
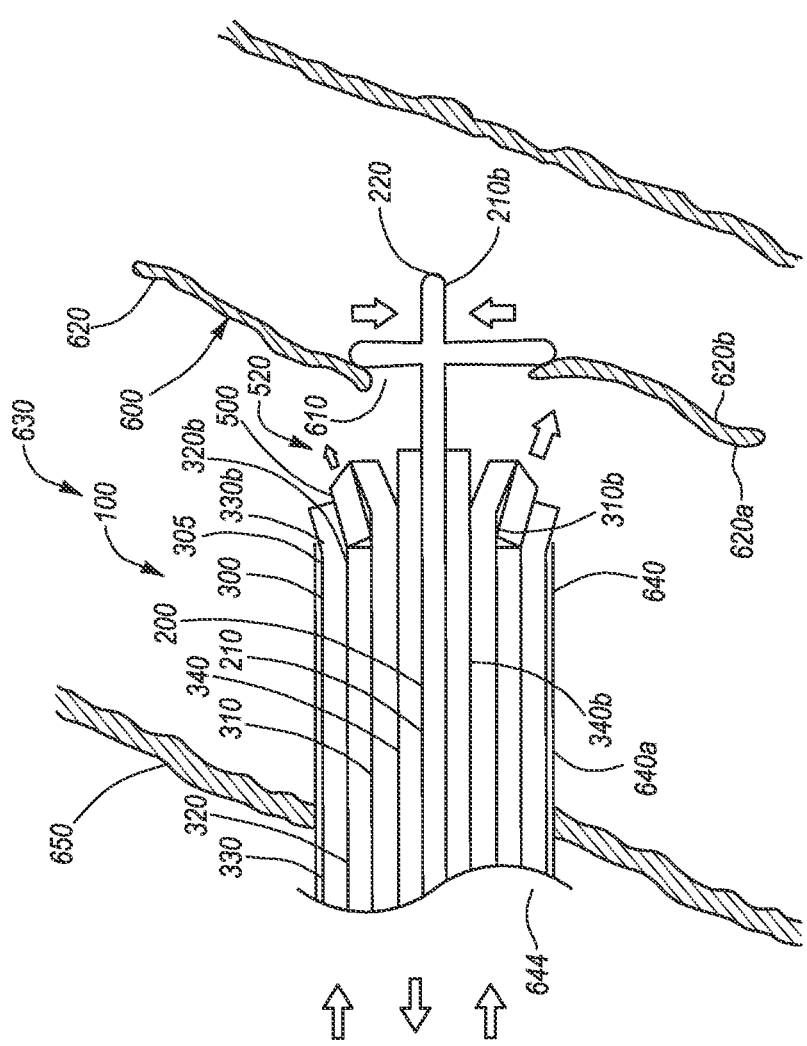

When tube set 305 is in the second predetermined position, carrier member 310 decouples from pusher member 320 in the manner described in detail above. Therefore, carrier member 310, cover member 330, and support member 340 may be inhibited from further axial movement and remain substantially stationary, whereas, pusher member 320 remains axially slidable. As pusher member 320 continues distally, distal end region 320*b* of pusher member 320 contacts substantially tubular closure element 500 and displaces substantially tubular closure element 500 from space 360 as shown in FIG. 15H. Since space 360 is substantially radially exposed, pusher member 320 directs substantially tubular closure element 500 over the distally-increasing cross-section of distal end region 310*b* of substantially-stationary carrier member 310 such that the cross-section of substantially tubular closure element 500 begins to radially expand, preferably in a substantially uniform manner. As substantially tubular closure element 500 traverses the distally increasing cross-section of distal end region 310*b*, the cross-section of substantially tubular closure element 500 radially expands beyond natural cross-section of closure element 500, as shown in FIGS. 14A-G.

Figure 15I:
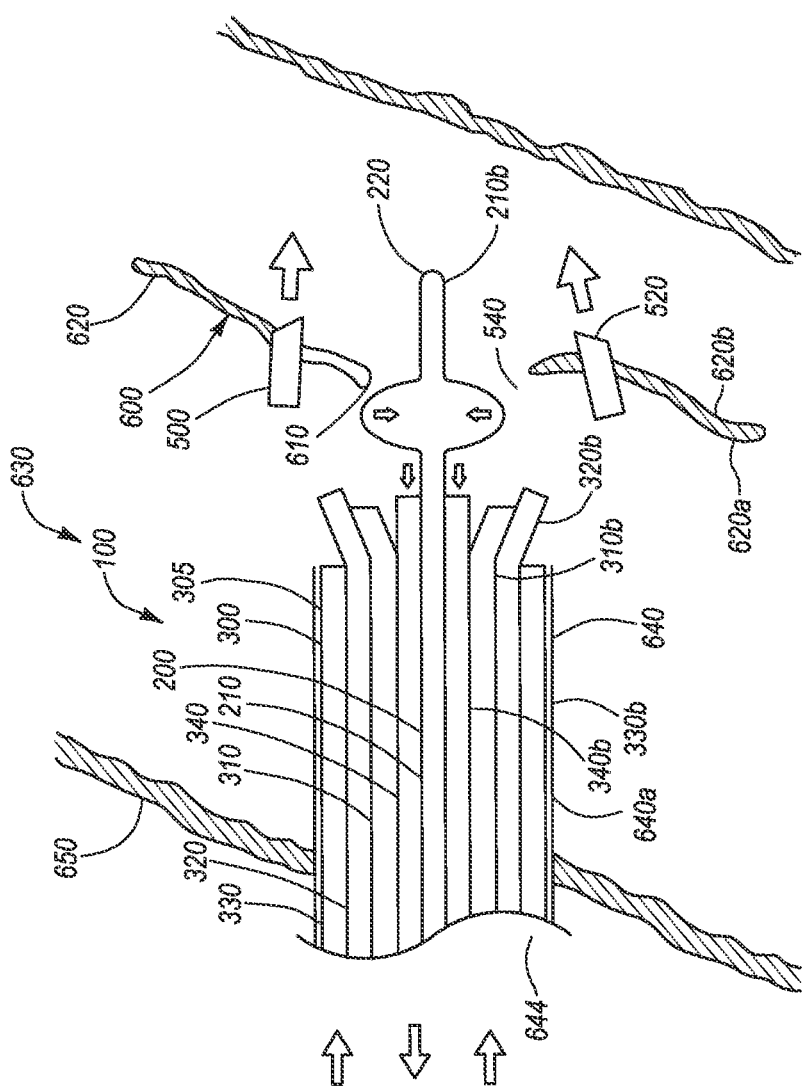

Upon being directed over the distally increasing cross-section of distal end region 320*b* by pusher member 320, substantially tubular closure element 500 is distally deployed as illustrated in FIG. 15I. When substantially tubular closure element 500 is deployed, tines 520 can pierce and otherwise engage significant amount of blood vessel wall 620 and/or tissue 630 adjacent to opening 610. For example, tines 520 can engage significant amount of blood vessel wall 620 and/or tissue 630 because cross-section 530 of substantially tubular closure element 500 is expanded beyond natural cross-section 530 of closure element 500 during deployment.

As closure element 500 is being deployed from the space, locator assembly 200 may begin to retract proximally and locator release system 490 can be activated to transition from the expanded state to the unexpanded state as substantially tubular closure element 500 is deployed. Distal end region 210b of locator assembly 200 may retract proximally and transition from the expanded state to the unexpanded state substantially simultaneously with the deployment of substantially tubular closure element 500. As desired, distal end region 210b may be configured to draw blood vessel wall 620 and/or tissue 630 adjacent to opening 610 proximally and into the channel defined by substantially tubular closure element 500. Tines 520 of substantially tubular closure element 500 thereby can pierce and otherwise engage blood vessel wall 620 and/or tissue 630.

Figure 15J:
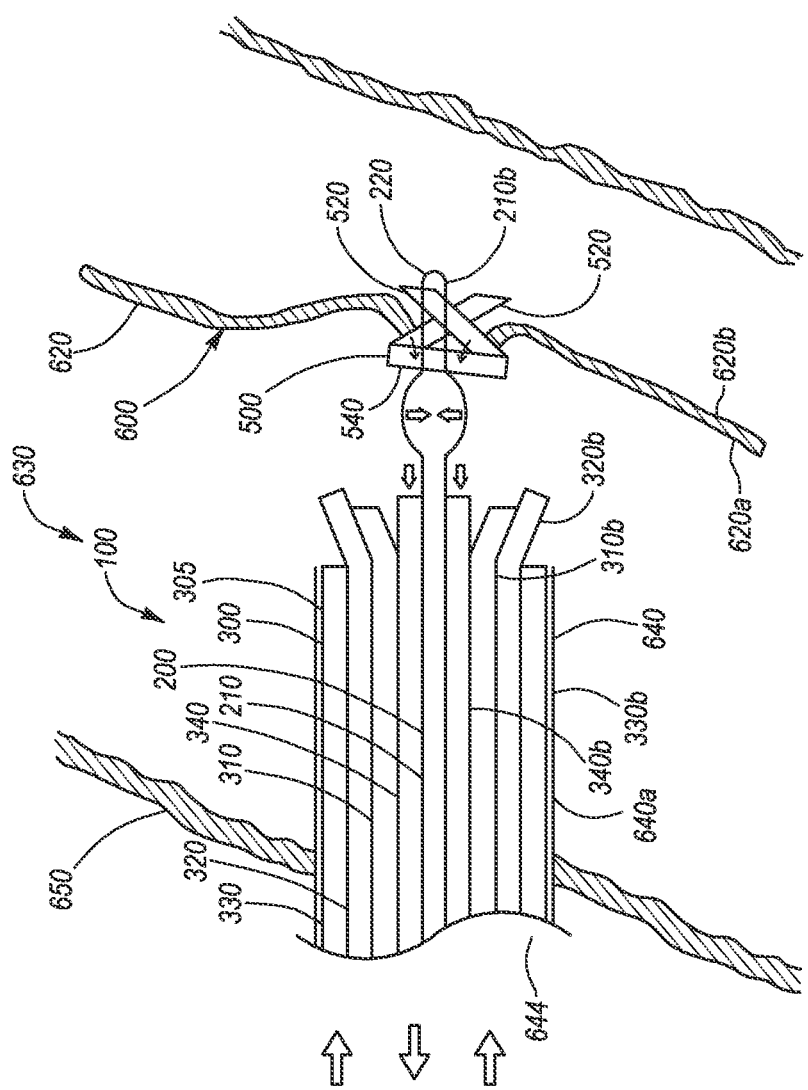
Figure 15K:
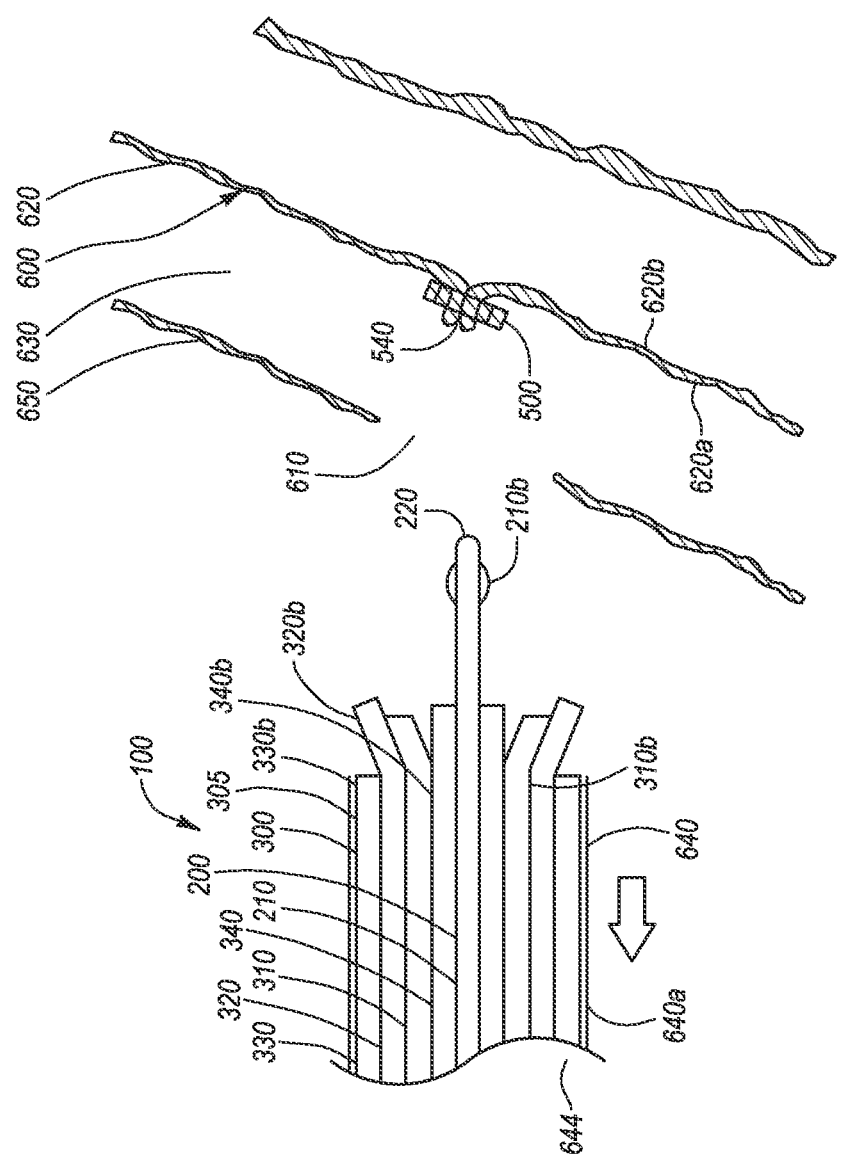

Turning to FIGS. 15J and 15K, substantially tubular closure element 500, once deployed, begins to transition from the tubular configuration, returning to the natural, planar configuration with opposing tines 520 and a natural cross-section of closure element 500. Preferably, substantially tubular closure element 500 substantially uniformly transitions from the tubular configuration to the natural, planar configuration. Rotating axially inwardly to form opposing tines 520 of the closure element 500, tines 520 draw the tissue into the channel as substantially tubular closure 500 element forms closure element 500. Also, the tissue is drawn substantially closed and/or sealed as the cross-section of substantially tubular closure element 500 contracts to return to the natural cross-section.

Turning to FIGS. 16A and 16B, embodiments of the apparatus 100, 1000 of the present invention may be configured to be utilized with sheath 640. Sheath 640 may be inserted or otherwise positioned into an opening in a body having a lumen. Sheath 640 generally has a substantially flexible or semi-rigid tubular member having a proximal end region 640a and a distal end region 640b and includes a predetermined length and a predetermined cross-section, both of which can be of any suitable dimension. Sheath 640 forms lumen 644 that extends along a longitudinal axis of sheath 640 and substantially between the proximal end region 640a and the distal end region 640b. Lumen 644 can have any suitable internal cross-section and is suitable for receiving one or more devices (not shown), such as a catheter, closure device, apparatus 100, 1000, or the like. Lumen 644 can be configured to slidably receive the tubular body 210 of locator assembly 200 and/or tube set 305 of the devices in accordance with the present invention. Sheath 640 may be formed from different materials as discussed herein.

Since the internal cross-section of sheath 640 may be less than or substantially equal to the predetermined cross-section of cover member 330 (FIG. 1A) of apparatus 100, sheath 640 may be configured to radially expand, such as by stretching, to receive tube set 305 (FIG. 1A). Alternatively, or in addition, sheath 640 may be advantageously configured to split as tube set 305 is received by, and advances within lumen 644 of sheath 640, thereby permitting the apparatus to access blood vessel wall 620. To facilitate the splitting, sheath 640 can include one or more splits, such as longitudinal splits 634. Each split may be configured to split sheath 640 in accordance with a predetermined pattern, such as in a spiral pattern, one exemplary embodiment of which is shown in FIG. 25B. It will be appreciated that, when the internal cross-section of sheath 640 is greater than the predetermined cross-section of cover member 330, it may not be desirable for sheath 640 to be configured to radially expand and/or split. In addition to, or alternatively, the apparatus 100 may include a cutting member, such as sheath cutter 701 shown in FIG. 2, that initiates a tear line or split in sheath 640 when sheath 640 is engaged with the distal end of the apparatus.

Sheath 640 may be advanced over a first guidewire or other rail (not shown), which has been positioned through the opening and into blood vessel 600 using conventional procedures such as those described above. In one configuration, blood vessel 600 is a peripheral blood vessel, such as a femoral or carotid artery, although other body lumens may be accessed using sheath 640. After the first guidewire or other rail is removed from lumen 644 and vessel 600, the opening, and consequently sheath 640, may be oriented with respect to blood vessel 600 such as to facilitate the introduction of devices through lumen 644 of sheath 640 and into blood vessel 600 with minimal risk of damage to blood vessel 600. One or more devices (not shown), such as a catheter, or the like, may be inserted through sheath 640 and advanced to a preselected location within the patient's body. For example, the devices may be used to perform a therapeutic or diagnostic procedure, such as angioplasty, atherectomy, stent implantation, and the like, within the patent's vasculature.

Sheath 640 may contain a secondary channel 670 formed in the perimeter wall 660 of sheath 640 through which a second guidewire 690 can be inserted. Secondary channel 670 may include a proximal entrance 670a near a hub portion 655 of sheath 640 as well as a distal exit 670b near the distal end of sheath 640. With sheath 640 already inserted into a body lumen, such as a blood vessel 600, second guidewire 690 can then be inserted into proximal entrance 670a and exit through distal exit 670b of secondary channel 670, into the body lumen. The secondary channel 670 may further include a valve or membrane to form a fluid tight seal to restrict fluid flow through the second channel 670 if a second guidewire 690 is not disposed therein. Lumen 644 of sheath 640 would, therefore, remain open for closure element 500 to be advanced through tube set 305. Upon deployment of closure element 500, second guidewire 690 may be positioned adjacent to the substantially planar closure element 500 and therefore remain within the body lumen and allow re-access to the site, if necessary.

Therefore, the second guidewire 690 may be used to re-access the site of the body lumen puncture in the patient if other complications arise upon closing of closure element 500. When second guidewire 690 is no longer needed, it may be removed from the lumen without disturbing the closure element.

The sheath 640 may be used in varying guidewire configurations. For example, a first guidewire may be inserted through the lumen 644, the sheath 640 may be inserted into a body lumen, i.e. the blood vessel 600, and the tube set 305 of the apparatus 100 may be advanced through the lumen 644, as described above. However, if the tube set 305 is larger than the lumen 644, the guidewire may be pushed through a wall (not shown) of the sheath 640 and into the secondary channel 670 making room for the tube set 305.

Referring now to FIG. 17, there is shown an exemplary embodiment of an introducer sheath 2100. The introducer sheath 2100, like the introducer sheath 640 described above, can include a hub portion 2102, which can include a proximal end 2116 and a distal end 2114, and a tubular portion 2104. Extending from the proximal end 2116 toward the distal end 2114 is a lumen 2110. This lumen 2110 can cooperate with a medical device (not shown), such as a vessel closure device, insertable therethrough. In the illustrated configuration, the lumen 2110 tapers or transitions from one cross-sectional configuration to another cross-sectional configuration near the distal end 2114 to meet or intersect with a lumen 2112 of the tubular portion 2104. It will be understood that the lumen 2110 can have a generally uniform cross-section along its length rather than tapering at its distal end. More generally, the lumen 2110 can include one or more transitional portions based upon the desired configuration and/or use with other medical devices.

The elongated tubular portion 2104 of the introducer sheath 2100 can extend from the distal end 2114 of the hub portion 2102. The tubular portion 2104 can include a distal end 2120 and a proximal end 2118. The proximal end 2118 can be integrally formed with the distal end 2114 of the hub portion 2102 or can be mounted or coupled to the distal end 2114 through a friction fit, mechanical bonding, adhesives, thermal or chemical bonding, combinations thereof or other manufacturing technique usable to mount, couple or attach two medical components. The distal end 2120 of the tubular portion 2104 can optionally include a tapered portion 2106 to facilitate insertion into a body lumen. This tapered portion 2106 may be formed during or after the initial forming process of the introducer sheath 2100. For instance, when the introducer sheath 2100 is formed through a molding or extrusion process, the tapered portion 2106 can be formed as part of this process. Alternatively, the tapered portion 2106 may be formed by heat forming, grinding or other known methods that result in a thinner wall thickness following the above-described molding or extrusion process or as part of a milling, machining, or similar process.

Optionally disposed at the transition between the hub portion 2102 and the tubular portion 2104 is a strain relief portion 2108. The strain relief portion 2108 would be disposed adjacent the distal end 2114 of the hub portion 2102 and adjacent the proximal end 2118 of the elongate tubular portion 2104. The strain relief 2108 would be configured to provide additional support to the proximal end 2118 of the elongated shaft 2104 to prevent kinking at the transition between the proximal end 2118 of the elongated member 2104 and the distal end 2114 of the hub portion 2102. In one embodiment, the strain relief portion 2108 can be formed by gradually increasing a thickness of tubular portion 2104 at the transition between the tubular portion 2104 and the hub portion 2102. In other configurations, the strain relief portion 2108 can include webs, extensions, or other internal or external structures to increase the strength and/or stiffness of the introducer sheath 2100 at the hub portion/tubular portion transition.

The tubular portion 2104 of the introducer sheath can be expandable. More specifically, in the illustrated configuration of FIG. 17, the tubular portion 2104 is of an elastomeric material that allows the diameter of the tubular portion 2104 to change as a medical device is inserted or removed from within the lumen 2112. The elastomeric material enables the tubular portion 2104 to expand/contract or deform/reform, while maintaining sufficient column stiffness or strength so that the introducer sheath 2100 can be inserted into the body lumen. In one configuration, the elastomeric material can be any of those described herein and such others as would be identified by one skilled in the art in light of the teaching contained herein.

Optionally, the tubular portion 2104 may also be configured to expand to a certain diameter at which point the tubular portion 2104 is further configured to split or separate into one or more portions to accommodate other medical devices, such as, but not limited to vessel closure devices, as will be described in more detail hereinafter.

Generally, each of the hub portion 2102 and the tubular portion 2104 can have at least a portion of which that is generally cylindrical in nature. Although portions 2102 and 2104 can have generally cylindrical portions, other cross-sectional configurations are possible, such as but not limited to, oval, polygonal, elliptical, or other cross-sectional configurations usable for a medical device that is insertable into a body lumen.

As previously described herein, the introducer sheath 2100 may be formed through an injection molding process. In an injection molding process, the hub portion 2102 and the elongated tubular portion 2104 are generally formed as a unitary member. Benefits of forming the introducer sheath 2100 as a unitary member include reduced costs, increased accuracy of part dimensions (i.e. dimension control) due to lack of assembly, alignment between the lumen 2112 of the tubular portion 2104 and the lumen 2110 of the hub portion 2102, and the balancing of mechanical properties across the entire sheath 2100 or of any particular portion or member of the sheath 2100. The thickness of the walls of the hub portion 2102 and/or of the tubular portion 2104 can also be controlled and varied as desired during the injection molding process.

Although reference is made herein to fabrication of the introducer sheath 2100 through use of injection molding techniques, one skilled in the art will appreciate that various other techniques can be used. For instance, the introducer sheath can be fabricated using milling, grinding, laser treatment, etching, or other techniques to form the introducer from a piece of material. Further, other techniques or methods can include those techniques used by those skilled in the art to fabricate medical devices.

With continued reference to FIG. 17, disposed within the hub portion 2102 is a flexible valve member 2122 disposed in the hub portion 2102. The valve member 2122 may be integrally formed into the hub portion 2102 during the molding process of the sheath 2100, or may be inserted after the sheath 2100 is integrally formed. For instance, the hub portion 2102 can included a receiving feature 2126, such as a groove or channel, to receive the valve member 2122. The cooperation between the receiving feature 2126 and the valve member 2122 result in a sealed hub portion 2102. Stated another way, the valve member 2122 is self-sealing once it is inserted into the hub portion 2102 to prevent fluid escaping from the body lumen.

The valve member 2122 can be a seal and can have a variety of different configurations to seal the sheath 2100. The valve member 2122, for example, may have an elastomeric body, such as silicone rubber, with at least one slit and/or other collapsible openings formed therein to allow selective insertion and removal of medical devices or instruments, such as guidewires, catheters, balloon pumps, and other such devices. At the same time, the material and/or structure of the valve member 2122 maintains a fluid tight seal around the medical devices or instruments. Thus, blood or other bodily fluids are prevented from leaking out, and unwanted air is prevented from entering into the body.

It will be understood that the valve member 2122 can be mounted or coupled to the hub portion 2102 in a number of other manners to achieve the sealed configuration for the hub portion 2102. For instance, the valve member 2122 can be retained with a retaining cap (not shown) disposed adjacent the proximal end of the hub portion 2102. In still another configuration, one or more flexible valves or valve members can be mounted within or to the proximal end 2116 of the hub portion 2102 by one or more retaining caps, rings, or members know to those skilled in the art. Although illustrated as a single member, the valve member 2122 can be formed of multiple parts to provide the desired fluid sealing capabilities. Exemplary flexible membranes or valve members, which can be utilized with the present invention, are shown in U.S. Pat. Nos. 4,798,594, 5,176,652, and 5,453,095 the entireties of which are herein incorporated by reference.

More generally, the introducer sheath can have a configuration similar to the introducer sheath disclosed in U.S. Provisional Patent Application Ser. No. 60/659,602 entitled "Introducer Sheath"; and 60/695,464 entitled "Modular Introducer Sheath; and co-pending U.S. patent application Ser. No. 11/427,301, filed Jun. 28, 2006, and entitled "Modular Introducer and Exchange Sheath" and Ser. No. 11/427,306, filed Jun. 28, 2006, and entitled "Expandable Introducer Sheath"), the disclosures of which are herein incorporated by reference. As such, the valve member 2122 can be mounted in the hub portion 2102 and the tubular portion 2104 can have a similar configuration to the tubular member to the introducer sheath described in the above-identified applications.

FIG. 17 also illustrates an optional port member 2124, such as a luer port/fitting, which may be formed on the hub portion 2102. The port member 2124 may function as a fluid port for the sheath 2100. Fluid (e.g., blood, antibiotics, plasma, saline, etc.) can thus be introduced and/or extracted through the fluid port 2124. The port member 2124 may also be optionally configured to align and/or selectively lock any device (e.g., a vessel closure device, a catheter) used in conjunction with the sheath 2100.

Figure 19:
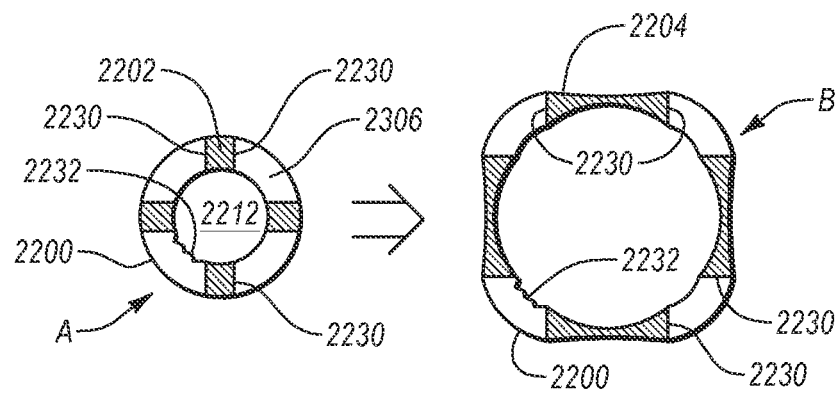
FIG. 19 illustrates a cross-sectional view of another embodiment of the introducer sheath in FIG. 17.
Figure 20:
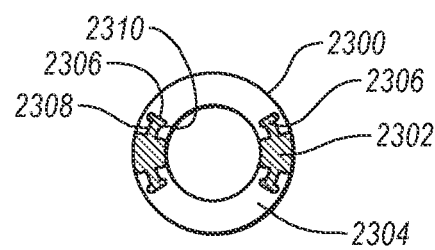
FIG. 20 illustrates a cross-sectional view of yet another embodiment of the introducer sheath in FIG. 17.
Figure 21:
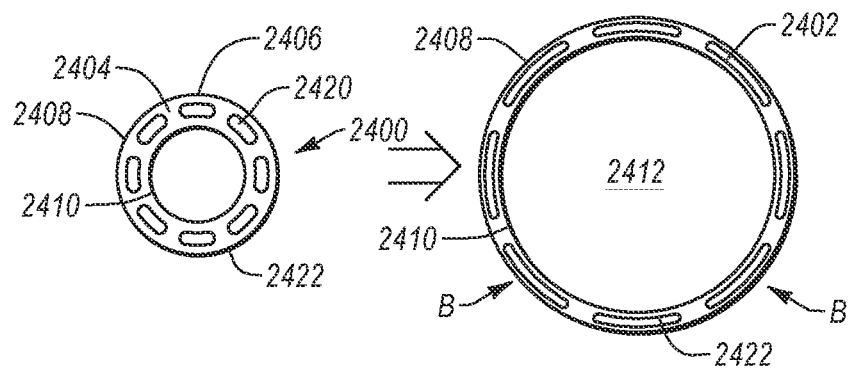
FIG. 21 illustrates a cross-sectional view of another embodiment of the introducer sheath in FIG. 17.

FIGS. 18-21 and 23-26 generally illustrate various configurations of the tubular body of the introducer sheath of the present invention. During the insertion/extraction of a medical device or instrument, the tubular body can deform/form or expand/contract as needed. Thus, the cross-sectional area of the tubular body may change during a medical procedure. In one example, the tubular body can expand in diameter from a first position to a second position having a diameter greater than the first position as a medical device is either withdrawn or inserted therethrough. The tubular body can also return to or substantially to the first position following withdrawal or insertion. The illustrated configurations of the tubular body each have a sheath portion and an elastic portion to provide the desired elasticity, stiffness, or strength. The sheath portion and the elastic portion can be formed from different materials as illustrated in FIGS. 18-20 discussed below. Alternatively, and as illustrated in FIG. 21, the tubular body can be fabricated from a single material, with the elastic portions being defined through the formation of lumens in the tubular body. The inclusion of lumens or of elastomeric materials in the formation of an introducer sheath enable the sheath to deform/form or expand/contract as described herein.

Although various features are illustrated in each Figure, any of the features in a particular Figure can be combined with features illustrated in another Figure. Further, the sheath portion and/or elastic portion are examples of one structure capable of performing the function of means for expanding a tubular body to accommodate the insertion or removal of a medical device.

Turning now to FIG. 18, illustrated is a tubular body, identified by reference numeral 2200, which can be used with the introducer sheath of the present invention, i.e., can function as the tubular body 2104 of FIG. 17, i.e., function to expand/contract or deform/reform to enable withdrawal of a medical device that may have enlarged in diameter during use. The tubular body 2200 can include at least one sheath portion 2204 and at least one elastic portion 2202. The sheath portion 2204 is typically formed of a first material and the elastic portion 2202 is often formed of a second material. In FIG. 18, the sheath portion 2204 can be formed in strips that run along the length of the tubular body 2200 from the distal end 2220 to the proximal end 2218, although the strips may have a shorter length. In some embodiments, the strips extend into the distal end 2114 (FIG. 17) of the hub portion 2102 (FIG. 17). The elastic portion 2202 can be formed in strips in this embodiment such that each strip of the elastic portion 2202 is adjacent to strips of the sheath portion 2204.

The elastic portion 2202 can be an elastomer that is bonded to the sheath portion 2204. In FIG. 18, each strip of the elastic portion 2202 is bonded on each side to adjacent strips of the sheath portion 2204. The elastic portion 2202 enables the tubular body 2200 to expand or deform such that the interior diameter or cross-sectional area of the lumen can change or increase. The diameter or cross-sectional area of the lumen 2212 can expand in certain locations and is not required to expand along the entire length of the tubular body 2200. Further, different portions of the tubular body 2200 may expand at different rates and/or at different times. The actual expansion of the tubular body 2200 can depend on a particular medical device that is inserted or withdrawn and/or the material used to form the tubular body 2200. The sheath portion 2204 can be selected to ensure that the lumen does not collapse when the tubular body 2200 is in a first, normal, or unstressed position and to provide stiffness or rigidity to the tubular body 2200. Thus, the sheath portion 2204 provides rigidity, flexibility, and the like or any combination thereof. In some embodiments, the sheath portion 2204 may also provide some elasticity to the tubular body 2200. Typically, however, the elastic portion 2202 has more elasticity than the sheath portion 2204.

FIG. 18 also illustrates an optional entry portion 2228 to the lumen 2212 of the tubular body 2200. The entry portion 2228 can be shaped to facilitate entry of any device that is entering the tubular body 2200 through the entry portion 2228. The entry portion 2228 can be formed when the tapered portion 2206 is formed and the slope of the tapered portion 2206 may be optionally altered to accommodate the entry portion 2228. By shaping the entry portion 2228, any device being withdrawn can more easily enter the lumen 2212 of the tubular body 2200. In one embodiment, the entry portion 2228 is concave and the edges at the distal end of the tubular body 2200 are smoothed. In other configurations, the entry portion 2228 can be generally curved, smooth, or other configuration to aid with withdrawal of a medical device into the lumen 2212.

The elongated tubular body 2200 can include an outer wall 2208 and an inner wall 2210 thereby defining a wall and a thickness of the wall. As with the lumen 2112 (FIG. 17), the lumen 2212 extends along the length of the tubular body 2200. The width, diameter, or cross-sectional area of the lumen 2212 can vary and may depend on intended use of the sheath 2100. More particularly in this embodiment, the width or diameter or cross-sectional area of the lumen 2212 can vary or expand and contract during use as the elastic portion 2202 changes shape, such as stretching and contracting. Because the hub portion 2102 (FIG. 17) and the tubular body 2200 are integrally formed in one configuration, the lumen 2212 of the tubular body 2200 remains aligned with the lumen 2110 (FIG. 17) of the hub portion 2102 (FIG. 17) even though the lumen 2212 expands, contracts, deforms, or reforms. It is contemplated that the wall thickness along the length of the elongated tubular body 2200 can be varied to vary mechanical properties of the sheath (stiffness, kink resistance, column strength, etc.).

FIG. 19 illustrates a cross section of the tubular body 2200 of the introducer sheath as it moves from first, normal, or unstressed position to a second, expanded, or stressed position of the tubular body 2200. In the first position, identified by reference letter A, the elastic portion 2202 of the tubular body 2200 is in a contracted or relaxed state and is bonded to the material of the sheath portion 2204 at the bond points 2230. The sheath portion 2204 can be typically formed from a material such that the lumen 2212 of the tubular body 2200 does not seal, close, or collapse in the first position, and/or to provide stiffness or flexibility to the tubular body 2200.

In the second position, identified by reference letter B, the elastic portion 2202 is expanded while the sheath portion 2204 has not expanded (or has expanded less than the elastic portion 2202) but is still bonded to the material at the bonds 2230. In one embodiment, the sheath portion 2204 may have some elasticity, but is generally configured to have less elasticity than the elastic portion 2202. The bond strength at the bond 2230 may be selected to permit the expansion of the tubular body 2200 to a predetermined diameter or by a predetermined amount. When that diameter or amount is exceeded, the tubular body 2200 may split at the bonds 2230 or at another location.

In some embodiments, a geometric pattern 2232 is formed on the inner wall 2210 or inner surface of the tubular body 2200, such as over all or at least one portion of the inner wall 2210 or inner surface. Further, the geometric pattern 2232 can be formed in or on the elastic portion 2202 and/or the sheath portion 2204. This geometric pattern 2232 can be used to impart certain desirable mechanical properties to the tubular body 2200, such as, but not limited to, stiffness, strength, kink resistance, or flexibility to the tubular body 2200.

Various structures and configurations of the geometric pattern 2232 can be used to provide the desired mechanical properties. For instance, in the illustrated configuration, the geometric pattern 2232 is formed on one portion or surface of the inner wall 2210 of the sheath portion 2204 though use of one or more grooves or recesses. The illustrated geometric pattern 2232 can represent a plurality of longitudinal grooves extending along an axis parallel to the longitudinal axis of the introducer sheath in a generally uniformly distributed pattern. In other configurations, however, the geometric pattern 2232 can be unevenly distributed or a combination of uniformly and unevenly distributed over all or a portion of the inner wall 2210 of the tubular body 2200. Further, the location of the grooves need not be parallel to the longitudinal axis of the introducer sheath, but can be transverse to such an axis and/or at any other angular orientation relative to the longitudinal axis.

It shall be understood that the pattern 2232 as shown in FIG. 19 should be considered exemplary and not limiting in any manner. It is contemplated that additional styles and types of patterns may be utilized in accordance with the present invention. For example, the pattern 2232 may be a sinusoidal pattern disposed about the inner radius of the tubular body 2200. Alternatively, the pattern 2232 may be configured to run along a different axis than one parallel to the longitudinal axis of the introducer sheath. For example, the pattern 2232 may be formed as a spiral. The pattern 2232 may also only extend partially along the length of the tubular body 2200.

Further, the pattern 2232 can extend along the length of the tubular body 2200 from the proximal end 2218 to the distal end 2220 or along a portion of the length of the tubular body 2200. The pattern 2232, or any portion thereof, may terminate prior to the proximal end 2220 of the tubular body 2200 or extend partially into the hub portion 2102 (FIG. 17). The pattern 2232 may also be a separation line, such as a pre-scored line. The pattern 2232 may be designed to facilitate splitting of at least a portion of the introducer sheath. For example, the introducer sheath may split along all or a portion of the geometric pattern 2232 after expanding past a predetermined limit.

FIG. 20 illustrated is a cross section view of another tubular body of an introducer sheath. This tubular body 2300 can be used with the introducer sheath 2100 (FIG. 17) and function to expand/contract or deform/reform to enable withdrawal of a medical device that may have enlarged in diameter during use. The tubular body 2300 has a similar configuration to that of tubular body 2200, and, as such, the description related to tubular body 2200 also applies to tubular body 2300. As with tubular body 2200, the tubular body 2300 includes at least one elastic portion 2302 and at least one sheath portion 2304. The elastic portion 2302 and the sheath portion 2304 are mechanically coupled and/or bonded together to provide additional strength to the connection or coupling between the elastic portion 2302 and the sheath portion 2304. For instance, in addition to or instead of a thermal or chemical bond between the elastic portion 2302 and the sheath portion 2304, a mechanical connection is made between the portions 2302 and 2304 to maintain the coupling or attachment of the elastic portion 2302 and the sheath portion 2304.

In the illustrated configuration of FIG. 20, the mechanical coupling or connection is facilitated by way of at least one interlocking feature 2306 that cooperates and mechanically engages with a corresponding recess or receiving portion of the sheath portion 2304. Each interlocking feature 2306 can include at least one extension 2308, which extends from the main body of the elastic portion 2302, and at least on protrusion 2310 extending from an end of the extension 2308. With the at least one protrusion 2310 extending from and being generally transverse to the extension 2310, the at least one protrusion 2310 aids with preventing detachment of the elastic portion 2302 from the sheath portion 2304 as the tubular body 2300 extends/contract or deforms/reforms. Although reference is made to the at least one protrusion 2310 extending transverse to the at least one extension 2308, one skilled in the art will appreciate that the at least one protrusion 2310 can extend from the at least one extension 2308 are other angular orientations while still being capable of preventing detachment.

The at least one interlocking feature 2306 illustrated in FIG. 20 can extend from a proximal end to a distal end of the tubular body 2300 and/or the introducer sheath. It will be understood, however, that the at least one interlocking feature 2306 can extend only part way from the distal end toward the proximal end, from the proximal end to the distal end, or at any location along the length of the tubular body 2300. Similarly, although the interlocking feature 2306 is illustrated as extending from the elastic portion 2302 toward the sheath portion 2304, it will be understood that the corresponding recess or receiving portion of the sheath portion 2304 can also be considered an interlocking feature. Further, the elastic portion 2302 can be configured with the corresponding recess or receiving portion, while the sheath portion 2304 includes the at least one extension 2308 and/or the at least one protrusion 2310.

The interlocking feature 2306 of the tubular body 2300 of FIG. 20 can be formed during the manufacturing process of the introducer sheath. For instance, the interlocking feature 2306, with the corresponding recess or receiving portion, can be formed during injection molding or during a coextrusion process of the tubular body 2300 and/or the introducer sheath. Alternatively, the interlocking feature 2306 can be formed during manufacture of the elastic portion, such as by injection molding or a co-extrusion process, with the elastic portion being subsequently bonded or coupled to the sheath portion, or vice versa, through thermal bonding, chemical bonding, or other known technique to bond similar or dissimilar medical grade materials.

Turning now to FIG. 21, illustrated is a cross section view of another tubular body of an introducer sheath. This tubular body 2400 can be used with the introducer sheath 2100 (FIG. 17) and function to expand/contract or deform/reform to enable withdrawal of a medical device that may have enlarged in diameter during use.

FIG. 21 illustrates a cross section of the tubular body 2400 of the introducer sheath as it moves from a first, normal, or unstressed position to a second, expanded, or stressed position of the tubular body 2400. In the first position, again identified by reference letter A, the tubular body 2400 is in a contracted or relaxed state. The tubular body 2400 is similar to the tubular body 2104 (FIG. 17), but further includes a plurality of lumens 2420 disposed at least partially in a wall 2422 defined by an outer wall 2408 and an inner wall 2410 of the tubular body 2400. The region of the tubular body 2400 containing the plurality of lumens 2422 has a smaller wall thickness than the remainder of the tubular body 2400. These regions of smaller wall thickness function as elastic portions 2402 of the tubular body 2400, while those regions of the wall 2422 having no lumens 2422 function as the sheath portion 2404. Stated another way, the inclusion of the plurality of lumens 2422 provides elasticity, expandability, or deformability to the tubular member 2400 at the elastic portions 2402. The number of lumens 2422 in the tubular body 2400 can vary based upon the degree of flexibility desired for the tubular body 2400. Further the particular size, cross-sectional shape, and/or ratio of lumen cross-sectional area to area of the wall can be varied to obtain different column strength, stiffness, kink resistance, elasticity, deformability, or other desirable mechanical properties or characteristics of the tubular member 2400.

In the expanded position, identified by reference letter B, the at least one lumen 2422 enables the relatively thinner wall portions of the tubular member 2400 to stretch, thereby increasing the cross-sectional area or shape of the tubular body 2400. After expansion, the tubular body 2400 can return to the first position.

Generally, by forming the tubular body as a composite member using materials having the desired elastic properties, whether or not the tubular body includes at least one lumen to increase the elasticity, expandability, or deformability of the tubular body, mechanical properties of the tubular body may be adjusted as desired. For example, if it is desirable to produce a sheath that is expandable during use, an elastomeric material can be selected along with another material having lower elastic properties. Forming a sheath using these materials, particularly in the tubular body, provides the sheath with the ability to expand when subject to an applied force. As discussed herein, the configuration of the two or more materials in the sheath can vary and may depend on use. For example, one of the materials may be selected to stiffen the overall tubular body, prevent kinking in the tubular body, and the like while the other material is selected based on an elastic property. The bond between the first and second materials can be adjusted to facilitate expansion of the sheath at an appropriate time or for other reasons.

In addition, the use of a geometric pattern can also be combined with the expandability of the sheath. The geometric pattern formed on the inner wall may be used to assist in splitting the sheath during use at an appropriate time, such as when the diameter exceeds a predetermined limit during expansion of the tubular member.

As described above, two or more materials may be utilized to form the sheath in accordance with the present invention. For example, a different material may be utilized to form the hub portion and one or more materials may be utilized to form the tubular body of the sheath. Again, the selection of materials may depend on the end use of the sheath, properties of medical devices used with the sheath, and the like or any combination thereof. Although the present invention has been shown and described in accordance with specific embodiments these should not be considered limiting in any manner. For example, multiple materials may be utilized to form a unitary sheath in accordance with the present invention, wherein multiple injection molding processes are performed simultaneously or in stages to form the unitary sheath in accordance with the present invention.

Embodiments of the introducer sheath described herein can be used in various medical procedures. In one example, a medical procedure often begins by introducing a sheath into body lumen, such as a patient's vasculature. After the sheath is properly introduced, a first medical device can be introduced through the sheath. During introduction of the first medical device, the sheath or at least the tubular body of the sheath may expand to accommodate a size of the first medical device.

After the first medical device has been introduced, the medical procedure may be performed. During this procedure, in one example, the size of the first medical device may change. During withdrawal of the first medical device, at least the tubular body of the sheath can expand or deform to accommodate the increased size of the first medical device. The expansion or change in cross-sectional area can occur at different locations of the sheath or the tubular body as the first medical device is withdrawn.

After the first medical device is withdrawn, a second medical device, such as a vessel closure device, stent delivery device, and/or other medical device, can be introduced through the sheath. This newly inserted medical device can be used without prior insertion of another introducer sheath. In the case of the vessel closure device, the vessel closure device can be placed in the desired location relative to the vessel wall and the introducer sheath removed before, during, or part of the vessel sealing process.

The above-described process is illustrated in more detail with reference to FIGS. 22A-22D. FIGS. 22A-22D illustrate an example of one configuration of an expandable introducer sheath during use in a medical procedure. A sheath 2600, which can be any of the introducer sheaths previously described with respect to FIGS. 17-21, can be inserted into a vessel or vasculature 600 or other body lumen of a patient. In this example, the tubular body 2604 of the sheath 2600 is formed of a first elastomeric material 2606 and a second material 2608. With the introducer sheath 2600 in place, one or more medical devices or instruments can be passed therethrough, such as through the lumens of the hub portion 2602 and the tubular body 2604, to gain access to the vasculature 600 and more particular to a treatment site.

Figure 22A:
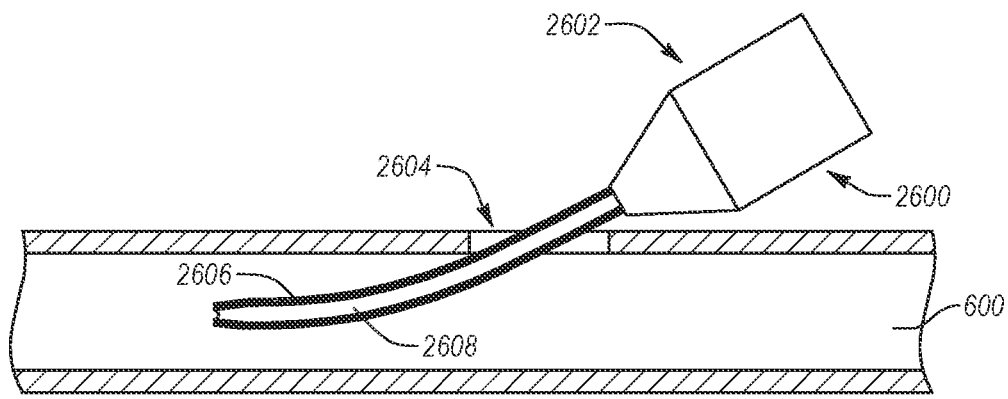
FIG. 22A illustrates an introducer sheath prior to insertion of a medical device.
Figure 22B:
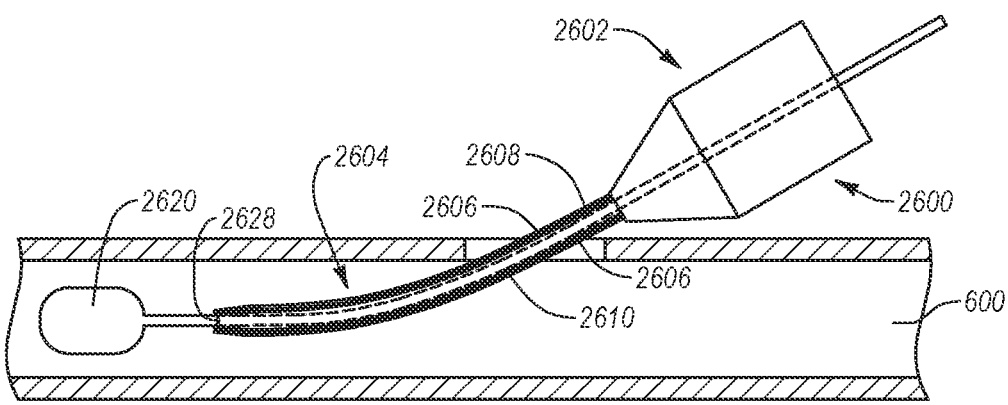
FIG. 22B illustrates an introducer sheath prior to removal of a medical device that has changed size during use.

In one configuration, and with reference to FIG. 22B, a medical device, such as, but not limited to, a dilation balloon or an intra-aortic balloon pump, identified by reference numeral 2620, can be passed through the hub portion 2602.

During use of the medical device 2620, the outside diameter of the medical device 2620 increases in size from when it was originally introduced into the vasculature 600 by way of the sheath 2600. The structure and function of the tubular body 2604 and/or the introducer sheath 2600 can, however, accommodate such a change and eliminates the need to remove the introducer sheath 2600 with the medical device 2620.

Figure 22C:
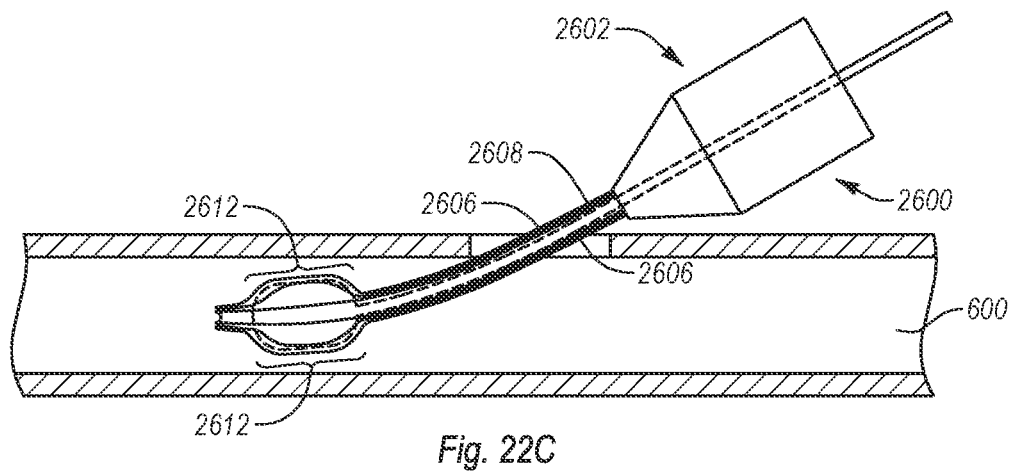
FIG. 22C illustrates an embodiment of the introducer sheath during removal of the medical device that has changed size during use.

With continued reference to FIG. 22B, once the medical procedure is complete, the medical device 2620 can be withdrawn until the medical device 2620 contacts the distal end of the introducer sheath 2600 and/or the entry portion 2628 that facilitates entry of the medical device 2620 back through the sheath 2616. As the medical device 2620 is withdrawn, its size introduces a force that causes the tubular body 2604 to expand as the first elastomeric material 2606 flexes, expands, or deforms accommodate the pump 2604, as illustrated in FIG. 22C.

As the medical device 2620 is withdrawn through the tubular body 2604, regions of the first elastomeric material 2606 expand, such as in region 2612, such that a cross-sectional area of the lumen of the sheath 2600 may increase, for example at least at this location. The medical device 2620 can therefore be withdrawn without splitting the sheath 2600 or without having to remove the sheath 2600 from the vasculature 600 during removal of the medical device 2620.

Figure 22D:
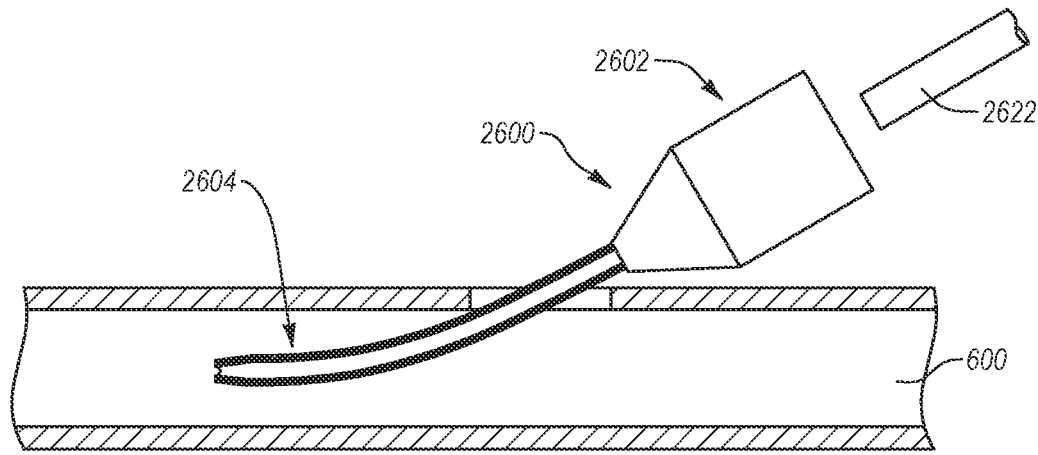
FIG. 22D illustrates the use of a vessel closure device that is introduced through the sheath after the medical device illustrated in FIGS. 6A and 6B has been withdrawn.

After the medical device 2620 is withdrawn, FIG. 22D illustrates that another medical device 422, such as a vessel closure device, a stent delivery device, or other medical device, can be introduced into the vasculature 600 via the sheath 2600. Without the expansion capability enabled by the embodiments disclosed herein, the sheath may need to be removed earlier than desired, which could preclude use of other medical devices, such as, but not limited to, the vessel closure device.

FIGS. 23-26 illustrate cross-sections of various embodiments of a tubular body of an alternative introducer sheath. Referring to the embodiment of FIG. 23, the tubular body 2700 may include a lumen 2712. The lumen 2712 may be defined by a wall 2710 similar to the lumen 2112 in the embodiment of FIG. 17. The lumen 2712 may be defined at least partially by the wall 2710. For example, the lumen 2712 may be defined partially by the wall 2710 and partially by at least one deformable expandable portion 2780. In other embodiments, the lumen 2712 may be entirely defined by the wall 2710. The wall 2710 may include two deformable expandable portions 2780a, 2780b.

The tubular body 2700 may include a secondary channel 2770. The secondary channel 2770 may be disposed within the wall 2710. For example, the secondary channel 2770 may be at least partially defined by the wall 2710. The secondary channel 2770 may be defined partially by the wall 2710 and partially by at least one of the deformable expandable portions 2780a, 2780b. In other embodiments, the secondary channel 2770 may be entirely defined by the wall 2710.

The secondary channel 2770 may be configured to receive a guidewire (not shown) in a manner similar to that described above. For example, the secondary channel 2770 may include at least one measurement or dimension, i.e. a diameter, width, etc., that is of sufficient size to receive a guidewire. In embodiments where a guidewire is, for example, a cylindrical guidewire with a diameter of about 1 mm, the secondary channel 2770 may have a diameter of more than about 1 mm (for a cylindrical channel) or a height and width of more than about 1 mm (for a rectangular channel). Furthermore, the secondary channel 2770 may have other measurements or dimensions to accommodate various shapes (for example, oval, polygonal, and/or other shapes) and sizes of guidewires.

The deformable expandable portions 2780 may be configured to increase a cross-sectional area of the tubular body 2700. It may be desirable to increase a cross-sectional area of the tubular body 2700 to facilitate the insertion and/or removal of apparatuses, i.e. medical devices or other apparatuses, into and/or from the tubular body 2700. Increasing a cross-sectional area of the tubular body 2700 may include increasing the cross-sectional area of the lumen 2712 and/or the cross-sectional area of the secondary channel 2770. In some embodiments, the deformable expandable portions 2780 may include an elastic portion as described in connection with FIGS. 18-20. In other embodiments, the deformable expandable portions 2780 may include a sheath portion as described in connection with FIGS. 18-20. In further embodiments, the deformable expandable portions 2780 may include expandable lumens 2720 in the tubular body 2700 as described in connection with FIG. 21.

In some embodiments, increasing the cross-sectional area of the tubular body 2700 may include breaching the wall 2710 of the tubular body 2700 such that the cross-sectional area is theoretically unbounded (though likely bounded by the surrounding tissue of the body lumen). In these embodiments, the deformable expandable portions 2780 may include portions of weakened structural integrity. These portions of weakened structural integrity may facilitate breaching the wall 2710 by splitting the tubular body 2700.

The deformable expandable portions 2780 may be positioned anywhere along the wall 2710 of the tubular body 2700. The locations of the deformable expandable portions 2780 may be selected depending on the application of the sheath. For example, if it is desirable that the outer surface of the tubular body 2700 remain intact (i.e. not split), one deformable expandable portion 2780 (i.e. the second deformable expandable portion 2780b) may be used between the lumen 2712 and secondary channel 2770, such that when an apparatus of larger size than the lumen 2712 or a guidewire of larger size than the secondary channel 2770 is used, the deformable expandable portion 2780 may expand and/or split so that the lumen 2712 and secondary channel 2770 are no longer separated, thereby increasing the cross-sectional area of both the lumen 2712 and the secondary channel 2770.

In the present embodiment, the deformable expandable portions 2780 may be configured to increase a cross-sectional area of the tubular body 2700 by having a smaller thickness $t_2$ than the thickness (for example $t_1$) of the rest of the wall 2710. The thickness of the deformable expandable portions 2780 may be uniform or non-uniform. The thickness of the wall 2710 may be uniform or non-uniform.

The first deformable expandable portion 2780a may increase a cross-sectional area of the tubular body 2700 by increasing a cross-sectional area of the lumen 2712. For example, if the first deformable expandable portion 2780a were the only deformable expandable portion 2780 in the tubular body 2700 of FIG. 23, when an apparatus of larger diameter than the lumen 2712 is inserted into the lumen, the first deformable expandable portion 2780a may expand. If the first deformable expandable portion 2780a expands up to a predetermined diameter and/or by a predetermined amount, the first deformable expandable portion 2780a may only expand a certain distance thereby increasing the cross-sectional area of the lumen 2712. If the first deformable expandable portion 2780a expands to and/or beyond a predetermined diameter and/or by a predetermined amount, the first deformable expandable portion 2780a may split thereby increasing the cross-sectional area of the lumen 2712.

The second deformable expandable portion 2780b may increase a cross-sectional area of the tubular body 2700 by increasing a cross-sectional area of the lumen 2712 and/or secondary channel 2770. For example, if the second deformable expandable portion 2780 were the only deformable expandable portion 2780 in the tubular body 2700 of FIG. 23, when an apparatus and/or a guidewire of larger diameter than the lumen 2712 and/or secondary channel 2770 is inserted into the lumen 2712 and/or secondary channel 2770, the second deformable expandable portion 2780b may expand. If the second deformable expandable portion 2780 expands up to a predetermined diameter and/or by a predetermined amount, the second deformable expandable portion 2780 may only expand a certain distance thereby increasing the cross-sectional area of the lumen 2712 and/or secondary channel 2770. If the second deformable expandable portion 2780 expands to and/or beyond a predetermined diameter and/or by a predetermined amount, the second deformable expandable portion 2780 may split thereby increasing the cross-sectional area of the lumen 2712 and/or secondary channel 2770 (by joining the lumen 2712 and secondary channel 2770).

The tubular body 2700 may be formed using one or more materials as described above. The deformable expandable portions 2780 may include the same material as the remainder of the wall 2710, as in the present embodiment. In other embodiments, at least one deformable expandable portion 2780 may include different materials.

FIGS. 24-26 illustrate cross-sections of various embodiments of a tubular body of an introducer sheath, in accordance with the present invention. The introducer sheaths of these alternative embodiments may be functionally similar to that of the device previously described above and shown in FIG. 23 in most respects, wherein certain features will not be described in relation to the alternative embodiments wherein those components may function in the manner as described above and are hereby incorporated into the alternative embodiments described below.

Referring to the embodiment of FIG. 24, the tubular body 2800 may include two deformable expandable portions 2880a, 2880b. In the present embodiment, the deformable expandable portions 2880 may be configured to increase a cross-sectional area of the tubular body 2800 by having overlapping portions 2890. In the present embodiment, the tubular body 2800 includes two deformable expandable portions 2880a, 2880b in the form of two pairs of overlapping portions 2890a, 2890b.

The first overlapping portions 2890a may increase a cross-sectional area of the tubular body 2800 by increasing a cross-sectional area of the lumen 2812. For example, if the first overlapping portions 2890a were the only deformable expandable portion 2880 in the tubular body 2800 of FIG. 24, when an apparatus of larger diameter than the lumen 2812 is inserted into the lumen 2812, the first overlapping portions 2890a may expand. If the first overlapping portions 2890a expands up to a predetermined diameter and/or by a predetermined amount, the first overlapping portions 2890a may only expand a certain distance (i.e. the two arms of the first overlapping portions 2890a may begin to separate while still overlapping) thereby increasing the cross-sectional area of the lumen 2812. If the first overlapping portions 2890a expand to and/or beyond a predetermined diameter and/or by a predetermined amount, the first overlapping portions 2890 may split (i.e. the two arms may open to allow the medical device to exit the lumen 2812) thereby increasing the cross-sectional area of the lumen 2812.

The second overlapping portions 2890b may increase a cross-sectional area of the tubular body 2800 by increasing a cross-sectional area of the secondary channel 2870 in a manner similar to the first overlapping portions 2890a. For example, if the second overlapping portions 2890b were the only deformable expandable portion 2880 in the tubular body 2800, when a guidewire of larger diameter than the secondary channel 2870 is inserted into the secondary channel 2870, the second overlapping portions 2890b may expand. If the second overlapping portions 2890 expand up to a predetermined diameter and/or by a predetermined amount, the second overlapping portions 2890 may only expand a certain distance (i.e. the two arms of the second overlapping portions 2890b may begin to separate while still overlapping) thereby increasing the cross-sectional area of the secondary channel 2870. If the second overlapping portions 2890 expands to and/or beyond a predetermined diameter and/or by a predetermined amount, the second overlapping portions 2890 may split (i.e. the two arms may open to allow the guidewire to exit the secondary channel 2870) thereby increasing the cross-sectional area of the secondary channel 2870.

Referring to the embodiment of FIG. 25, the tubular body 2900 may include six deformable expandable portions 2980. The deformable expandable portions 2980 may be configured to increase a cross-sectional area of the tubular body 2900 by including geometric patterns 2932 that are similar to the geometric patterns 2232 described in connection with FIG. 19. Additional examples of geometric patterns 2232 are illustrated in FIGS. 25A and 25B.

In the present embodiment, the geometric patterns 2932 may be configured to facilitate splitting of at least a portion of the tubular body 2900. For example, the geometric patterns 2932 may be configured to facilitate splitting the tubular body 2900 near the secondary channel 2970 and/or lumen 2912.

The geometric patterns 2932, in the present embodiment, may be located on both sides of the wall 2910 of the tubular body 2900. For example, the first and second geometric patterns 2932a, 2932b, in the present embodiment, are located on both sides of the wall 2910 at a location near the lumen 2912 farthest from the secondary channel 2970. In other embodiments, only one geometric pattern 2932 may be positioned at this location. For example, only the first geometric pattern 2932a located on an outside surface of the wall 2910 farthest from the secondary channel 2970 may be used. Alternatively, only the second geometric pattern 2932b located on an inside surface of the wall 2910 farthest from the secondary channel 2970 may be used.

Referring to the geometric patterns (not shown) illustrated in FIGS. 25A and 25B, FIG. 25A includes longitudinal grooves 2934 as geometric patterns. The longitudinal grooves 2934 may be formed as deformable expandable portions. For example, the tubular body 2700' may be extruded with the longitudinal grooves 2934. In another example, the longitudinal grooves 2934 may be a separation line, such as a line that is pre-scored in the deformable expandable portions. In the present embodiment, multiple longitudinal grooves 2934 may be included. In other embodiments, a single longitudinal groove 2934 may be included.

FIG. 25B illustrates another embodiment of a geometric pattern. The geometric pattern shown in FIG. 25B may be a longitudinal groove 2934'. The longitudinal groove 2934', in the present embodiment, may be a spiral shaped longitudinal groove 2934'. In other embodiments, a plurality of longitudinal grooves 2934' may be used. In further embodiments, a plurality of longitudinal grooves 2934' may be used.

Referring to the embodiment of FIG. 26, the tubular body 3000 may include three deformable expandable portions 3080. The deformable expandable portions 3080 may be configured to increase a cross-sectional area of the tubular body 3000 by being formed of a weaker material than the other portions of the tubular body 3000.

Similar to the first deformable expandable portion 2780a described in connection with FIG. 23, the first deformable expandable portion 3080a, in the present embodiment, may increase a cross-sectional area of the tubular body 3000 by increasing a cross-sectional area of the lumen 3012. However, rather than having a smaller thickness compared to other portions of the tubular body 3000, the deformable expandable portions 3080 of the present embodiment may have the same and/or greater thickness compared to other portions of the tubular body 3000. A cross-sectional area of the tubular body 3000 may still be increased because the deformable expandable portions 3080 may include material that is of weakened structural integrity than the remaining portions of the tubular body 3000. The weaker material may facilitate expansion and/or splitting of the deformable expandable portions 3080 when the deformable expandable portions 3080 expand up to and/or beyond a predetermined diameter and/or by a predetermined amount thereby increasing the cross-sectional area of the tubular body 3000.

In some embodiments, the deformable expandable portions 3080 may be coextruded with the rest of the tubular body 3000. In other embodiments, the deformable expandable portions 3080 may be bonded to the rest of the tubular body 3000 through, for example, a friction fit, mechanical bonding, adhesives, thermal or chemical bonding, combinations thereof or other bonding methods.

FIGS. 27A-29B illustrate cross-sections of further embodiments of a tubular body of an introducer sheath, in accordance with the present disclosure. The introducer sheaths of these further embodiments may be functionally similar to that of the device previously described above and shown in FIGS. 23-26 in most respects, wherein certain features will not be described in relation to the alternative embodiments wherein those components may function in the manner as described above and are hereby incorporated into the alternative embodiments described below.

Referring to the embodiment shown in FIGS. 27A-27E, the tubular body 3100 may include a lumen 3112. The lumen 3112 may be defined by a wall 3110 similar to the lumen 2112, 2712 in the embodiments of FIGS. 17 and 23, respectively. The lumen 3112 may be defined at least partially by the wall 3110. For example, the lumen 3112 may be defined partially by the wall 3110 and partially by at least one expandable divider, such as expandable divider 3180b. In other embodiments, the lumen 3112 may be entirely defined by the wall 3110.

The tubular body 3100 may include a channel 3170. The channel 3170 may be disposed within the wall 3110. For example, the channel 3170 may be at least partially defined by the wall 3110. The channel 3170 may be defined partially by the wall 3110 and partially by the expandable divider 3180b. In other embodiments, the channel 3170 may be entirely defined by the wall 3110.

The channel 3170 may be configured to receive a guidewire (not shown) in a manner similar to that described above. For example, the channel 3170 may include at least one measurement or dimension, i.e. a diameter, width, area, other dimension, or combinations thereof, that is of sufficient size to receive a guidewire. In embodiments where a guidewire is, for example, a cylindrical guidewire with a diameter of about 1 mm, the channel 3170 may have a diameter of more than about 1 mm (for a cylindrical channel) or a height and width of more than about 1 mm (for a rectangular channel). Furthermore, the channel 3170 may have other measurements or dimensions to accommodate various shapes (for example, oval, polygonal, other shapes, or combinations thereof) and/or sizes of guidewires.

Figure 27A:
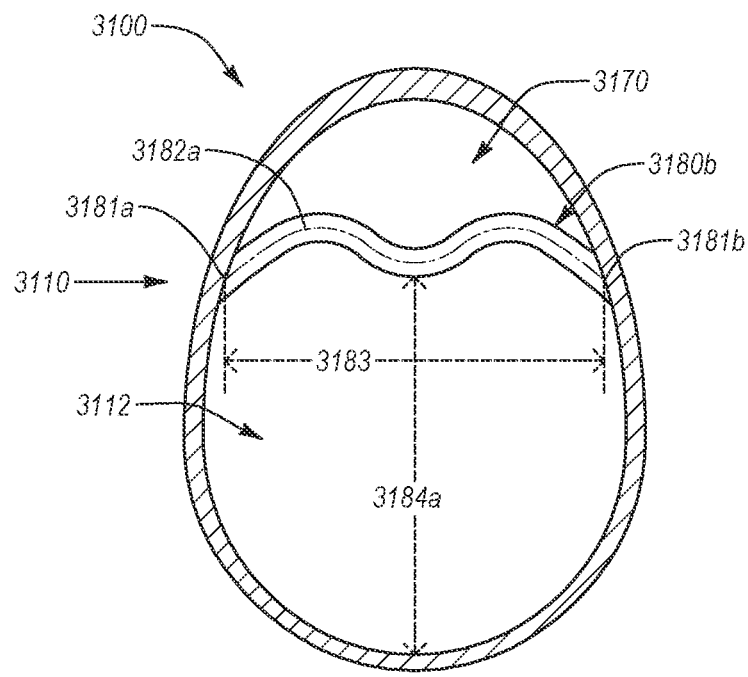
FIGS. 27A-29B illustrate cross-sections of further embodiments of a tubular body of an introducer sheath.
Figure 27B:
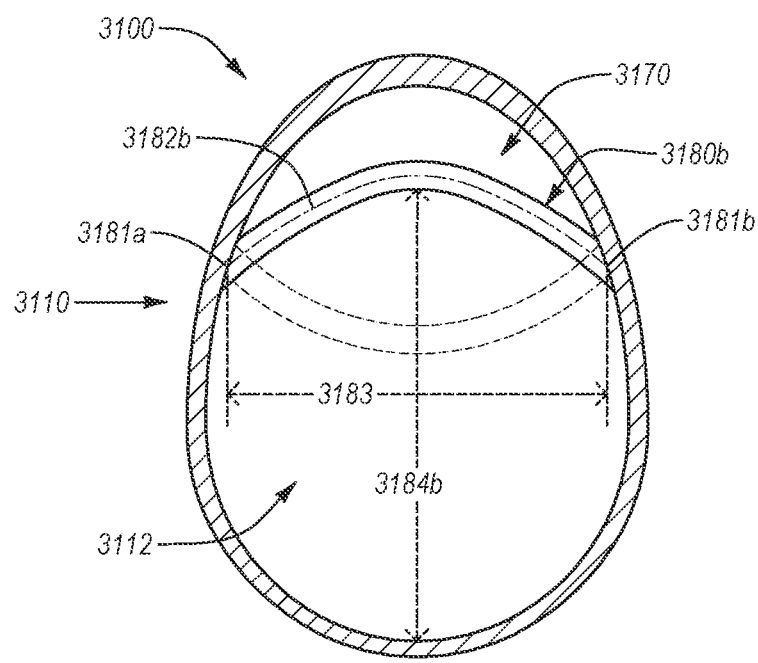
Figure 27C:
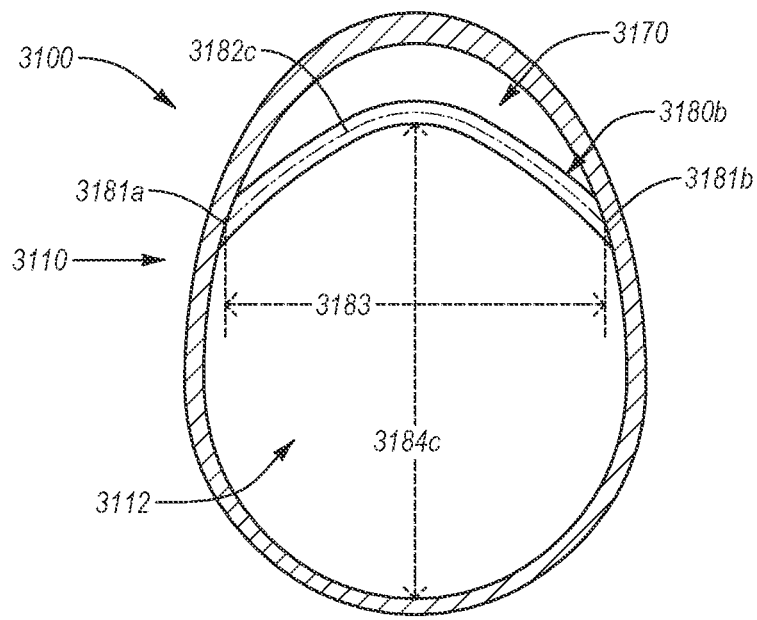
Figure 27D:
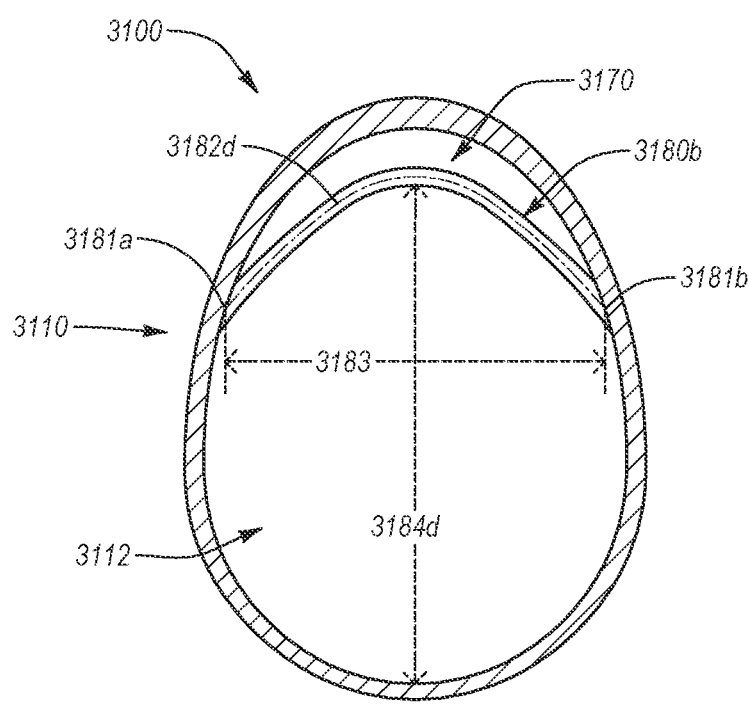
Figure 27E:
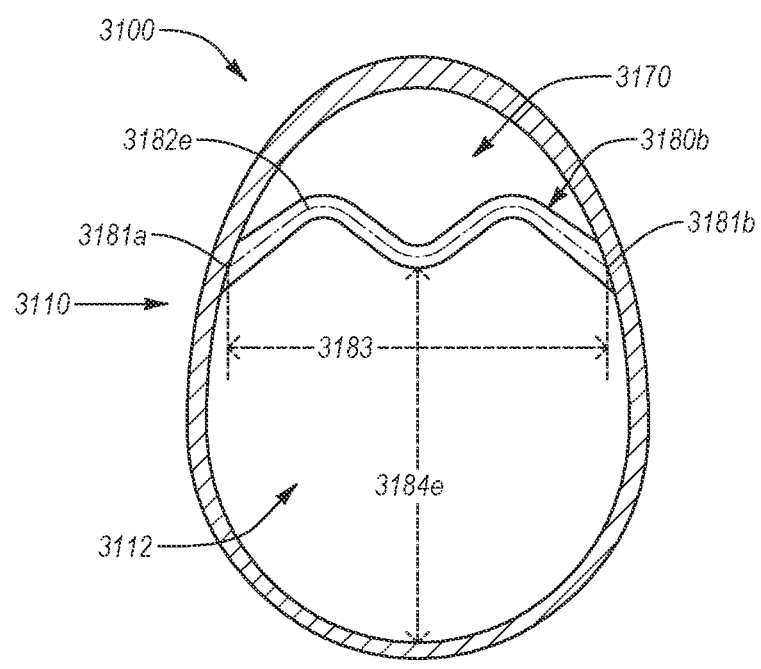

The expandable divider 3180b may be configured to increase a cross-sectional area of the lumen 3112 from a pre-expanded configuration toward an expanded configuration. FIG. 27A illustrates the expandable divider 3180b in the pre-expanded configuration; FIG. 27B illustrates the expandable divider 3180b in the expanded configuration; FIG. 27C illustrates the expandable divider 3180c in an elastically deformed configuration; FIG. 27D illustrates the expandable divider 3180c in a plastically deformed configuration; and FIG. 27E illustrates the expandable divider 3180c in the pre-expanded configuration after being transitioned to the plastically deformed configuration shown in FIG. 27D. It may be desirable to increase a cross-sectional area of the lumen 3112 to facilitate the insertion and/or removal of apparatuses, i.e. medical devices or other apparatuses, into and/or from the lumen 3112. The expandable divider 3180b may be configured to increase a cross-sectional area of the channel 3170.

In the present configuration, the expandable divider 3180b may include a first end 3181a and a second end 3181b. The expandable divider 3180b, as shown in FIG. 27A, may have a generally sinusoidal shape from the first end 3181a toward the second end 3181b. In other embodiments, the expandable divider 3180b may have a sinusoidal shape, a concertina shape, an overlapping shape, a serpentine shape, other shapes, or combinations thereof.

A first linear length 3183 may be defined from the first end 3181a toward the second end 3181b. A linear length may include the shortest distance between two points, for example the shortest distance between the first end 3181a and the second end 3181b.

If the expandable divider 3180b expands up to a predetermined dimension and/or by a predetermined amount, the expandable divider 3180b may only expand a certain distance thereby increasing the cross-sectional area of the lumen 3112 and/or channel 3170. The expandable divider 3180b may transition beyond a predetermined dimension and/or a predetermined amount. For instance, the expandable divider 3180b may elastically and/or plastically deform when an instrument and/or guidewire expands the expandable divider beyond its unfurled or expanded size.

The predetermined dimension may include a first divider length, shown as 3182a, 3182b, 3182c, 3182d, 3182e in FIGS. 27A-27E, respectively. The first divider length 3182a, 3182b, 3182c, 3182d, 3182e may be defined from the first end 3181a toward the second end 3181b along the expandable divider 3180b. A divider length may include the distance along a divider between two points, for example the distance along the expandable divider 3180b between the first end 3181a and the second end 3181b. A divider length may include the distance along a length of a curved, stepped, concertina shape, and/or another divider.

The first divider length 3182a, shown in FIG. 27A, may be about the same as the first divider length 3182b, shown in FIG. 27B. The first divider length 3182c in the elastically deformed configuration may be longer than the first divider length 3182a in the pre-expanded configuration and/or the first divider length 3182b in the expanded configuration. The first divider length 3182*d* in the plastically deformed configuration is generally longer than the first divider length 3182*a* in the pre-expanded configuration, the first divider length 3182*b* in the expanded configuration, the first divider length 3182*c* in the elastically deformed configuration, or combinations thereof. The first divider length 3182*e* in the pre-expanded configuration after being transitioned to the plastically deformed configuration shown in FIG. 27D may be longer than the first divider length 3182*a* in the pre-expanded configuration, the first divider length 3182*b* in the expanded configuration, the first divider length 3182*c* in the elastically deformed configuration, or combinations thereof.

The first linear length 3183 may be related to the first divider length 3182*a*, 3182*b*, 3182*c*, 3182*d*, 3182*e*. For instance, the first linear length 3183 may be a chord length with respect to the first divider length 3182*b*, 3182*c*, 3182*d*, when in the expanded, elastically deformed, or plastically deformed configurations. In another example, the first linear length 3183 may be directly proportional to the first divider length 3182*a*, 3182*b*, 3182*c*, 3182*d*, 3182*e*. In the present configuration, the first divider length 3182*a*, 3182*b* in the pre-expanded and expanded configurations may be about fifty percent longer than the first linear length 3183. For example, an inner dimension 3184*a* of the lumen 3112 in the pre-expanded configuration may be about eight French compared to a ten French inner dimension 3184*b* in the expanded configuration.

In other embodiments, the first divider length 3182*a*, 3182*b*, 3182*c*, 3182*d*, 3182*e* may be more or less than about fifty percent longer than the first linear length 3183. For instance, the first divider length 3182*a*, 3182*b*, 3182*c*, 3182*d*, 3182*e* may be between about five percent and about ninety-five percent, twenty percent and about eighty percent, forty percent and about seventy percent, or other ranges longer than the first linear length 3183. In another example, the ratio of an inner dimension 3184*a* of the lumen 3112 in the pre-expanded configuration to an inner dimension 3184*b* in the expanded configuration may be about six French compared to about twelve French, about seven French to about twelve French, about eight French to about twelve French, about eight French to about eleven French, about eight French to about ten French, about eight French to about nine French, or other ratios.

The inner dimension 3184*a* in the pre-expanded configuration shown in FIG. 27A is generally smaller than the inner dimension 3184*b* in the expanded state shown in FIG. 27B. The inner dimension 3184*c* in the elastically deformed configuration may be larger than the inner dimension 3184*a* in the pre-expanded configuration and/or the inner dimension 3184*b* in the expanded configuration. The inner dimension 3184*d* in the plastically deformed configuration is generally larger than the inner dimension 3184*a* in the pre-expanded configuration, the inner dimension 3184*b* in the expanded configuration, the inner dimension 3184*c* in the elastically deformed configuration, or combinations thereof. The inner dimension 3184*e* in the pre-expanded configuration after being transitioned to the plastically deformed configuration shown in FIG. 27D may be larger than the inner dimension 3184*a* in the pre-expanded configuration, the inner dimension 3184*b* in the expanded configuration, the inner dimension 3184*c* in the elastically deformed configuration, or combinations thereof.

In some embodiments, increasing the cross-sectional area of the tubular body 3100 may include breaching the wall 3110 of the tubular body 3100 such that the cross-sectional area is theoretically unbounded (though likely bounded by the surrounding tissue of the body lumen). In these embodiments, the deformable expandable dividers 3180 may include portions of weakened structural integrity. These portions of weakened structural integrity may facilitate breaching the wall 3110 by splitting the tubular body 3100. As shown in FIGS. 27A-27B, the expandable divider 3180*b* is not configured to be breached, but rather is configured to unfurl or expand toward the expanded configuration, as shown in FIG. 27B.

The expandable divider 3180*b* may be positioned between the lumen 3112 and channel 3170, such that when an apparatus of larger size than the lumen 3112 or a guidewire of larger size than the channel 3170 is used, the expandable divider 3180*b* may unfurl or expand to accommodate an apparatus of larger size than the lumen 3112 and/or may split so that the lumen 3112 and channel 3170 are no longer separated, thereby increasing the cross-sectional area of both the lumen 3112 and the channel 3170.

The expandable divider 3180*b* may increase a cross-sectional area of the lumen 3112 and/or channel 3170. For example, if the expandable divider 3180*b* were the only expandable divider in the tubular body 3100 of FIG. 27, when an apparatus and/or a guidewire of larger diameter than the lumen 3112 and/or channel 3170 is inserted into the lumen 3112 and/or channel 3170, the expandable divider 3180*b* may expand (i.e. without deforming, elastically deforming, plastically deforming, or combinations thereof) from the lumen 3112 toward the channel 3170 or vice versa. For instance, FIG. 27B illustrates (in phantom) the expansion of the expandable divider 3180*b* into the lumen 3112.

The tubular body 3100 may be formed using one or more materials as described above. The expandable divider 3180*b* may include the same material as the remainder of the wall 3110, as in the present embodiment. In other embodiments, the expandable divider 3180*b* may include different materials. The expandable divider 3180*b* and/or wall 3110 may be extruded or otherwise formed in their unexpanded shape, as shown in FIG. 27A. In embodiments where the expandable divider 3180*b* may be elastically deformable, the expandable divider 3180*b* may return to its original shape after a medical instrument and/or guidewire is removed from the lumen 3112 and/or channel 3170.

Figure 28A:
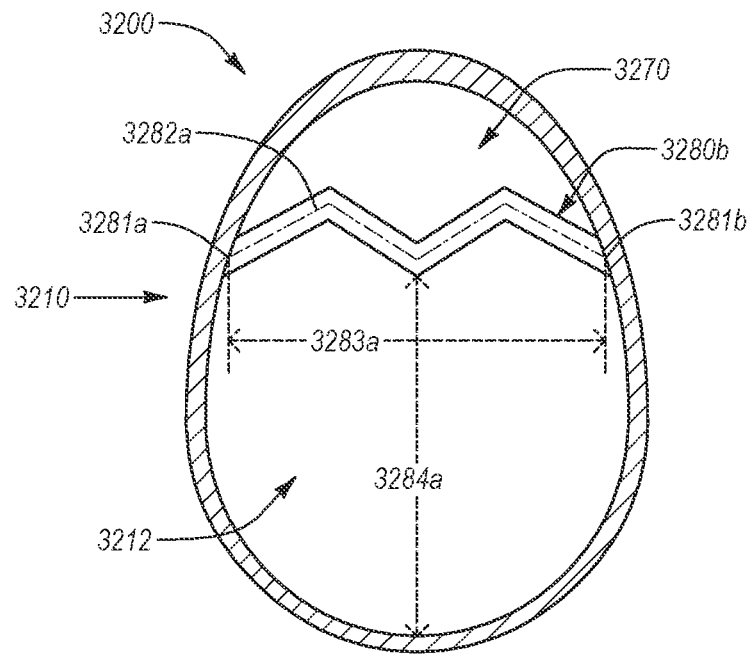
Figure 28B:
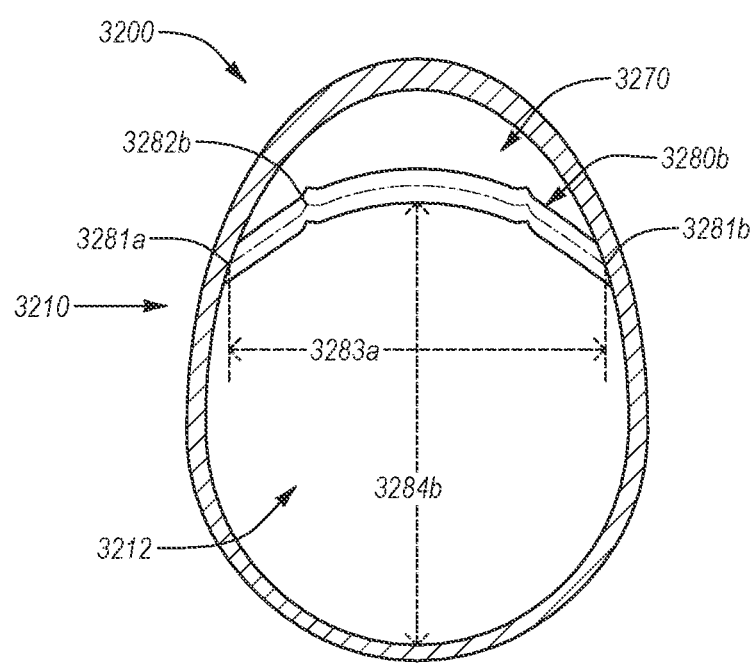

Referring to the embodiment shown in FIGS. 28A-28B, the tubular body 3200 may include a lumen 3212. The lumen 3212 may be defined by a wall 3210 similar to the lumen in the embodiments of FIGS. 17 and 23, respectively. The lumen 3212 may be defined at least partially by the wall 3210. For example, the lumen 3212 may be defined partially by the wall 3210 and partially by at least one expandable divider, such as expandable divider 3280*b*. In other embodiments, the lumen 3212 may be entirely defined by the wall 3210.

The tubular body 3200 may include a channel 3270. The channel 3270 may be disposed within the wall 3210. For example, the channel 3270 may be at least partially defined by the wall 3210. The channel 3270 may be defined partially by the wall 3210 and partially by the expandable divider 3280*b*. In other embodiments, the channel 3270 may be entirely defined by the wall 3210. The channel 3270 may be configured to receive a guidewire (not shown) in a manner similar to that described above.

The expandable divider 3280*b* may be configured to increase a cross-sectional area of the lumen 3212 from a pre-expanded configuration toward an expanded configuration. FIG. 28A illustrates the expandable divider 3280*b* in the pre-expanded configuration while FIG. 28B illustrates the expandable divider 3280*b* in the expanded configuration.

The expandable divider 3280*b* may be configured to increase a cross-sectional area of the channel 3270.

In the present configuration, the expandable divider 3280*b* may include a first end 3281*a* and a second end 3281*b*. The expandable divider 3280*b*, as shown in FIG. 28A, may have a generally concertina shape from the first end 3281*a* toward the second end 3281*b*. In other embodiments, the expandable divider 3280*b* may have a sinusoidal shape, a concertina shape, an overlapping shape, a serpentine shape, other shapes, or combinations thereof.

A first linear length 3283*a* may be defined from the first end 3281*a* toward the second end 3281*b* along the expandable divider 3280*b*. A first curve length 3282*a* may be defined from the first end 3281*a* toward the second end 3281*b*. The first linear length 3283*a* may be related to the first curve length 3282*a*. In the present configuration, the first curve length 3282*a* may be about fifty percent longer than the first linear length 3283*a*. In other embodiments, the first divider length 3282*a* may be more or less than about fifty percent longer than the first linear length 3283*a*. For instance, the first divider length 3282*a* may be between about five percent and about ninety-five percent, twenty percent and about eighty percent, forty percent and about seventy percent, or other ranges longer than the first linear length 3283*a*. In another example, an inner dimension 3284*a* of the lumen 3112 in the pre-expanded configuration may be about eight French compared to a ten French inner dimension 3284*b* in the expanded configuration.

In some embodiments, increasing the cross-sectional area of the tubular body 3200 may include breaching the wall 3210 of the tubular body 3200 such that the cross-sectional area is theoretically unbounded (though likely bounded by the surrounding tissue of the body lumen). In these embodiments, the deformable expandable dividers 3280 may include portions of weakened structural integrity. These portions of weakened structural integrity may facilitate breaching the wall 3210 by splitting the tubular body 3200. As shown in FIGS. 28A-28B, the expandable divider 3280*b* is not configured to be breached, but rather is configured to unfurl or expand toward the expanded configuration, as shown in FIG. 28B.

The expandable divider 3280*b* may be positioned between the lumen 3212 and channel 3270, such that when an apparatus of larger size than the lumen 3212 or a guidewire of larger size than the channel 3270 is used, the expandable divider 3280*b* may unfurl or expand to accommodate an apparatus of larger size than the lumen 3212 and/or may split so that the lumen 3212 and channel 3270 are no longer separated, thereby increasing the cross-sectional area of both the lumen 3212 and the channel 3270.

The expandable divider 3280*b* may increase a cross-sectional area of the lumen 3212 and/or channel 3270. If the expandable divider 3280*b* expands up to a predetermined diameter and/or by a predetermined amount, the expandable divider 3280*b* may only expand a certain distance thereby increasing the cross-sectional area of the lumen 3212 and/or channel 3270. The expandable divider 3280*b* may deform beyond its expanded or unfurled capacity. For instance, the expandable divider 3280*b* may elastically and/or plastically deform when an instrument and/or guidewire expands the expandable divider beyond its unfurled or expanded size.

The predetermined dimension may include a first divider length, shown as 3282*a*, 3282*b* in FIGS. 28A-28B, respectively. The first divider length 3282*a*, 3282*b* may be defined from the first end 3281*a* toward the second end 3281*b* along the expandable divider 3280*b*. A divider length may include the distance along a divider between two points, for example the distance along the expandable divider 3280*b* between the first end 3281*a* and the second end 3281*b*. A divider length may include the distance along a length of a curved, stepped, concertina shape, and/or another divider.

The first divider length 3282*a*, shown in FIG. 28A, may be about the same as the first divider length 3282*b*, shown in FIG. 28B. The expandable divider 3280*b* may transition to an elastically deformed configuration (similar to the elastically deformed configuration shown in FIG. 27C), to a plastically deformed configuration (similar to the plastically deformed configuration shown in FIG. 27D), to a pre-expanded configuration after being transitioned to the plastically deformed configuration (similar to the pre-expanded configuration after being transitioned to the plastically deformed configuration shown in FIG. 27D).

The tubular body 3200 may be formed using one or more materials as described above. The expandable divider 3280*b* may include the same material as the remainder of the wall 3210, as in the present embodiment. In other embodiments, the expandable divider 3280*b* may include different materials. The expandable divider 3280*b* and/or wall 3210 may be extruded or otherwise formed in their unexpanded shape, as shown in FIG. 28A. In embodiments where the expandable divider 3280*b* may be elastically deformable, the expandable divider 3280*b* may return to its original shape after a medical instrument and/or guidewire is removed from the lumen 3212 and/or channel 3270.

Figure 29A:
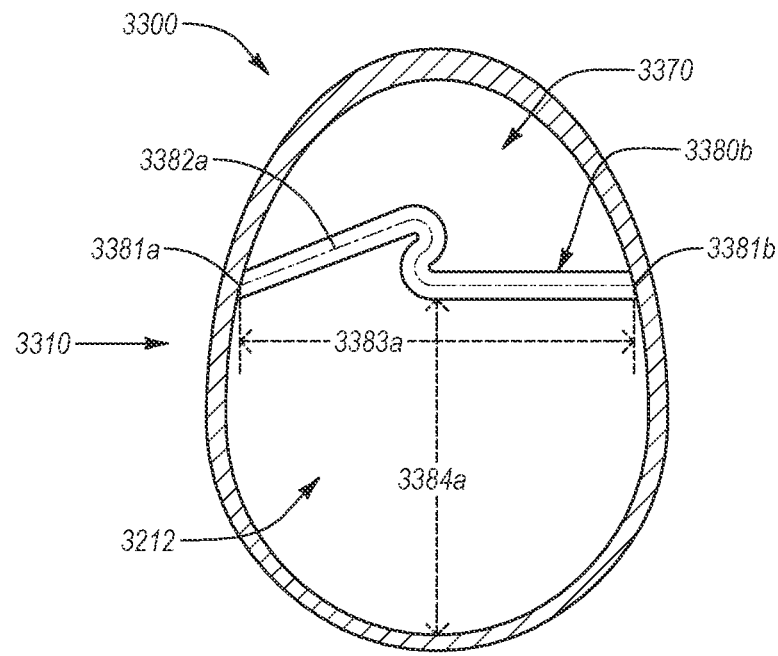
Figure 29B:
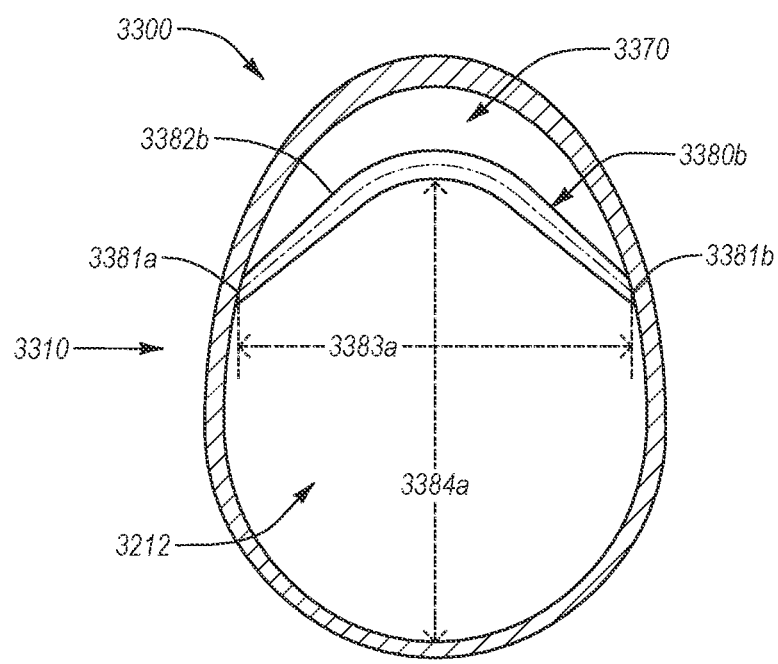

Referring to the embodiment shown in FIGS. 29A-29B, the tubular body 3300 may include a lumen 3312. The lumen 3312 may be defined by a wall 3310 similar to the lumen 2112, 2712 in the embodiments of FIGS. 17 and 23, respectively. The lumen 3312 may be defined at least partially by the wall 3310. For example, the lumen 3312 may be defined partially by the wall 3310 and partially by at least one expandable divider, such as expandable divider 3380*b*. In other embodiments, the lumen 3312 may be entirely defined by the wall 3310.

The tubular body 3300 may include a channel 3370. The channel 3370 may be disposed within the wall 3310. For example, the channel 3370 may be at least partially defined by the wall 3310. The channel 3370 may be defined partially by the wall 3310 and partially by the expandable divider 3380*b*. In other embodiments, the channel 3370 may be entirely defined by the wall 3310. The channel 3370 may be configured to receive a guidewire (not shown) in a manner similar to that described above.

The expandable divider 3380*b* may be configured to increase a cross-sectional area of the lumen 3312 from a pre-expanded configuration toward an expanded configuration. FIG. 29A illustrates the expandable divider 3380*b* in the pre-expanded configuration while FIG. 29B illustrates the expandable divider 3380*b* in the expanded configuration. The expandable divider 3380*b* may be configured to increase a cross-sectional area of the channel 3370.

In the present configuration, the expandable divider 3380*b* may include a first end 3381*a* and a second end 3381*b*. The expandable divider 3380*b*, as shown in FIG. 29A, may have a generally overlapping shape from the first end 3381*a* toward the second end 3381*b*. In other embodiments, the expandable divider 3380*b* may have a sinusoidal shape, a concertina shape, an overlapping shape, a serpentine shape, other shapes, or combinations thereof.

A first linear length 3382*a* may be defined from the first end 3381*a* toward the second end 3381*b* along the expandable divider 3380*b*. A first curve length 3382*b* may be defined from the first end 3381*a* toward the second end 3381*b*. The first linear length 3382*a* may be related to the first curve length 3382b. In the present configuration, the first curve length 3382b may be about fifty percent longer than the first linear length 3382a. In other embodiments, the first divider length 3382b may be more or less than about fifty percent longer than the first linear length 3382a. For instance, the first divider length 3382b may be between about five percent and about ninety-five percent, twenty percent and about eighty percent, forty percent and about seventy percent, or other ranges longer than the first linear length 3382a.

In some embodiments, increasing the cross-sectional area of the tubular body 3300 may include breaching the wall 3310 of the tubular body 3300 such that the cross-sectional area is theoretically unbounded (though likely bounded by the surrounding tissue of the body lumen). In these embodiments, the deformable expandable dividers 3380 may include portions of weakened structural integrity. These portions of weakened structural integrity may facilitate breaching the wall 3310 by splitting the tubular body 3300. As shown in FIGS. 29A-29B, the expandable divider 3380b is not configured to be breached, but rather is configured to unfurl or expand toward the expanded configuration, as shown in FIG. 29B.

The expandable divider 3380b may be positioned between the lumen 3312 and channel 3370, such that when an apparatus of larger size than the lumen 3312 or a guidewire of larger size than the channel 3370 is used, the expandable divider 3380b may unfurl or expand to accommodate an apparatus of larger size than the lumen 3312 and/or may split so that the lumen 3312 and channel 3370 are no longer separated, thereby increasing the cross-sectional area of both the lumen 3312 and the channel 3370.

The expandable divider 3380b may increase a cross-sectional area of the lumen 3312 and/or channel 3370. If the expandable divider 3380b expands up to a predetermined diameter and/or by a predetermined amount, the expandable divider 3380b may only expand a certain distance thereby increasing the cross-sectional area of the lumen 3312 and/or channel 3370. The expandable divider 3380b may deform beyond its expanded or unfurled capacity. For instance, the expandable divider 3380b may elastically and/or plastically deform when an instrument and/or guidewire expands the expandable divider beyond its unfurled or expanded size.

The predetermined dimension may include a first divider length, shown as 3382a, 3382b in FIGS. 29A-29B, respectively. The first divider length 3382a, 3382b may be defined from the first end 3381a toward the second end 3381b along the expandable divider 3380b. A divider length may include the distance along a divider between two points, for example the distance along the expandable divider 3380b between the first end 3381a and the second end 3381b. A divider length may include the distance along a length of a curved, stepped, concertina shape, and/or another divider.

The first divider length 3382a, shown in FIG. 29A, may be about the same as the first divider length 3382b, shown in FIG. 29B. The expandable divider 3380b may transition to an elastically deformed configuration (similar to the elastically deformed configuration shown in FIG. 27C), to a plastically deformed configuration (similar to the plastically deformed configuration shown in FIG. 27D), to a pre-expanded configuration after being transitioned to the plastically deformed configuration (similar to the pre-expanded configuration after being transitioned to the plastically deformed configuration shown in FIG. 27D).

The tubular body 3300 may be formed using one or more materials as described above. The expandable divider 3380b may include the same material as the remainder of the wall 3310, as in the present embodiment. In other embodiments, the expandable divider 3380b may include different materials. The expandable divider 3380b and/or wall 3310 may be extruded or otherwise formed in their unexpanded shape, as shown in FIG. 29A. In embodiments where the expandable divider 3380b may be elastically deformable, the expandable divider 3380b may return to its original shape after a medical instrument and/or guidewire is removed from the lumen 3312 and/or channel 3370.

Figure 30:
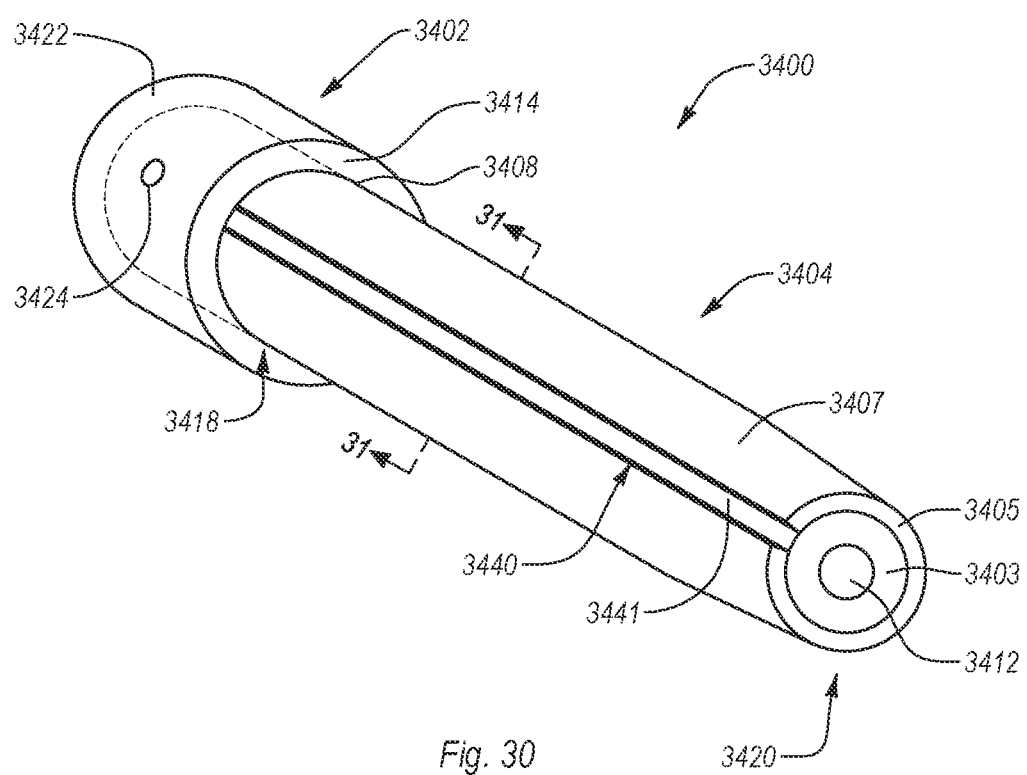
FIG. 30 illustrates a perspective view of an embodiment of an introducer sheath.

FIG. 30 illustrates a perspective view of an embodiment of an introducer sheath 3000. The introducer sheath 3400 of the embodiment described herein and shown in FIG. 30 may be functionally similar to the introducer sheaths described herein in most respects, wherein certain features may not be described in relation to this embodiment wherein those components may function in the manner as described above and are hereby incorporated into this embodiment described below. Like structures and/or components are given like reference numerals.

The introducer sheath 3400 may include a hub portion 3402 with an elongate or tubular portion 3404 extending therefrom. As illustrated, the hub portion 3402 may include a strain relief portion 3408 to provide additional support to a proximal end 3418 of the elongate portion 3404 to prevent kinking at the transition between the proximal end 3418 of the elongated portion 3404 and a distal end 3414 of the hub portion 3402. The hub portion 3402 may also include a valve member 3422, such as a hemostatis valve, and a fluid port 3424 configured to permit fluid (e.g., blood, antibiotics, plasma, saline, etc.) to be introduced and/or extracted through the hub portion 3402. The fluid port 3424 may be configured to align and/or selectively lock any device (e.g., a vessel closure device, a catheter) used in conjunction with the sheath 3400. Other combinations of structures of the hub portion 3402 are possible.

The elongate portion 3404 may extend between the proximal end 3418 and a distal end 3420. The elongate portion 3404 may include an inner portion 3403 and an outer portion 3405, with the inner portion 3403 and/or the outer portion 3405 extending between the proximal end 3418 and the distal end 3420 of the tubular portion 3404.

As illustrated, the inner portion 3403 may form a lumen 3412. The lumen 3412 may include an entry portion, such as entry portion 2228 shown in FIG. 18. The outer portion 3405 of the lumen 3412 may be disposed partially around the inner portion 3403. For example, at least a portion of the inner portion 3403 may be exposed between the proximal end 3418 and the distal end 3420 of the tubular portion 3404 by way of at least one aperture 3440. In the present embodiment, the aperture 3440 may extend from the proximal end 3418 toward the distal end 3420 and terminate at the distal end 3420. In other embodiments, the aperture 3440 may extend from the proximal end 3418 and terminate proximal the distal end 3420. In still another configuration, the aperture 3440 may be disposed between and spaced apart from either or both the proximal end 3418 and the distal end 3420. The aperture 3440 may extend from an outer surface 3407 of the outer portion 3405 to an outer surface 3441 of the inner portion 3403. The aperture 3440 may vary in size. For example, the aperture 3440 as shown in FIG. 30 may define a gap. In other embodiments, the aperture 3440 may be smaller, like a slit. Although, regardless of the size of the aperture 3440, as the sheath 3400 expands, the aperture 3440 will increase in size.

Figure 31:
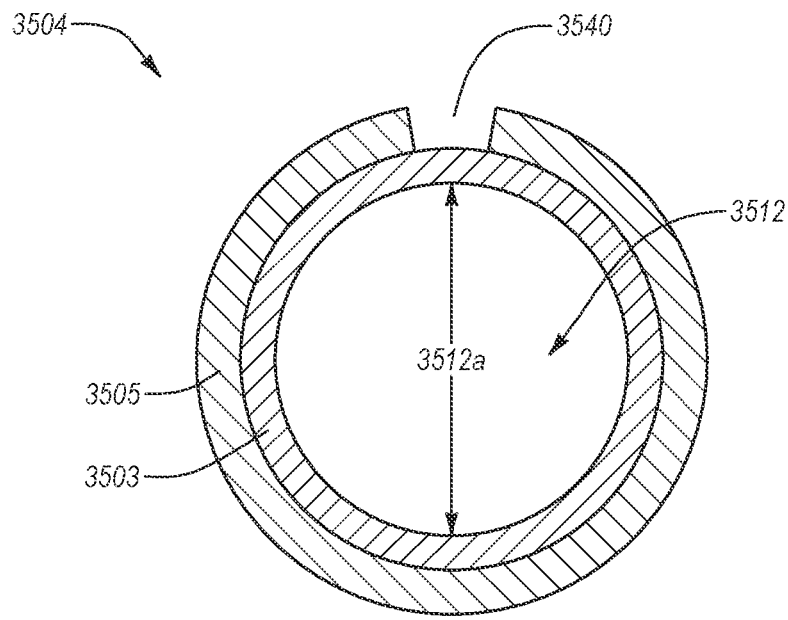
FIG. 31 illustrates a cross-sectional view of the tubular portion of the introducer sheath of FIG. 30 along line 31-31 of FIG. 30 in an unexpanded state.

FIG. 31 illustrates a cross-sectional view of the elongate portion 3404 of the introducer sheath 3400 of FIG. 30 along line 31-31 of FIG. 30 in an unexpanded state. The lumen

3512 of the introducer sheath 3500 illustrated in FIG. 31 is in an unexpanded state. The lumen 3512 may include a first inner dimension 3512*a*. The first inner dimension 3512*a* may include a diameter, a cross-sectional area, a radius, an arc length, other dimensions, or combinations thereof. For example, the first inner dimension 3512*a* may be a diameter of about six French.

The inner portion 3503 may include a first material that may include at least one relatively expandable material. The first material may provide lubricious properties to facilitate medical devices being inserted and/or removed through the lumen 3512. For example, the first material may include ePTFE, which may provide both expandability and lubricity.

The outer portion 3505 may include a second material that may provide expandability and/or lubricity. For example, the second material may include an elastomeric material. In the present embodiment, the second material may be less expandable (i.e. may have a lower modulus of elasticity) than the first material of the inner portion 3503. In embodiments where the second material may be less expandable than the first material and despite the reduced expandability of the second material, the exposure of the inner portion 3503 through at least a portion of the outer portion 3505 may facilitate expansion of the inner portion 3503. A less expandable second material may increase the longitudinal strength (i.e. resistance to buckling in the longitudinal direction) and/or pushability of the introducer sheath while providing radial and/or other expandability of the introducer sheath through the more expandable first material.

The inner portion 3503 and/or the outer portion 3505 may be arranged to facilitate entry and/or exit of a medical device through the lumen 3512 by expanding to accommodate the medical device without creating further apertures (not shown) in the outer surface 3507 of the tubular portion 3504.

FIG. 31 illustrates a cross-sectional view of the elongate or tubular portion 3504' of the introducer sheath 3400 along line 31-31 of FIG. 30 in an expanded state. The elongate portion 3504' of the embodiment described herein and shown in FIG. 9 may be functionally similar to the introducer sheaths and/or tubular portions described herein in most respects, wherein certain features may not be described in relation to this embodiment wherein those components may function in the manner as described above and are hereby incorporated into this embodiment described below. Like structures and/or components are given like reference numerals.

The elongate portion 3504', the inner portion 703', the outer portion 3505', the lumen 3512', the aperture 3540', other components of the introducer sheath 3400, or combinations thereof, may increase in at least one dimension in the expanded state. The inner portion 3503' and the outer portion 3505' may expand in conjunction with the lumen 3512'. The aperture 3540' may expand circumferentially. Expansion of the aperture 3540' may increase the size of the exposed portion of the inner portion 3503' of the elongate portion 3504'. The outer portion 3505' may be disposed around less of the inner portion 3503' in the expanded state.

Figure 32:
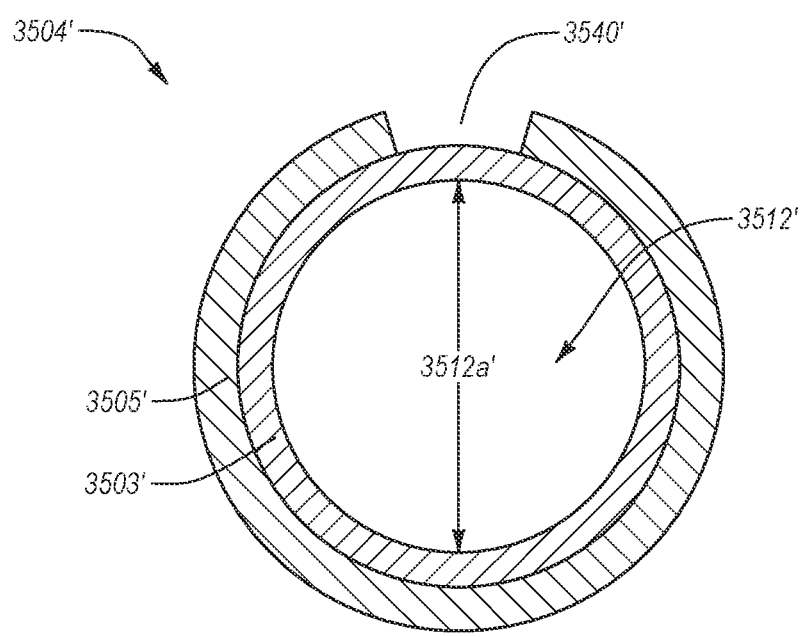
FIG. 32 illustrates a cross-sectional view of the tubular portion of the introducer sheath along line 31-31 of FIG. 30 in an expanded state.

The lumen 3512' is shown in FIG. 32 in the expanded state. The lumen 3512' may include a second inner dimension 3512*a'*. The second inner dimension 3512*a'* may include a diameter, a cross-sectional area, a radius, an arc length, other dimensions, or combinations thereof. For example, the second inner dimension 3512*a'* may be a diameter of about ten French. The lumen 3512 (shown in FIG. 31) may expand from a first inner dimension 3512*a* to a second inner dimension 3512*a'* of the lumen 3512'. This expansion may be about sixty-five percent. For example, from about six French to about ten French. In other embodiments, the expansion may be more and/or less than about sixty-five percent. For example, it may be as little as about ten percent.

Figure 33:
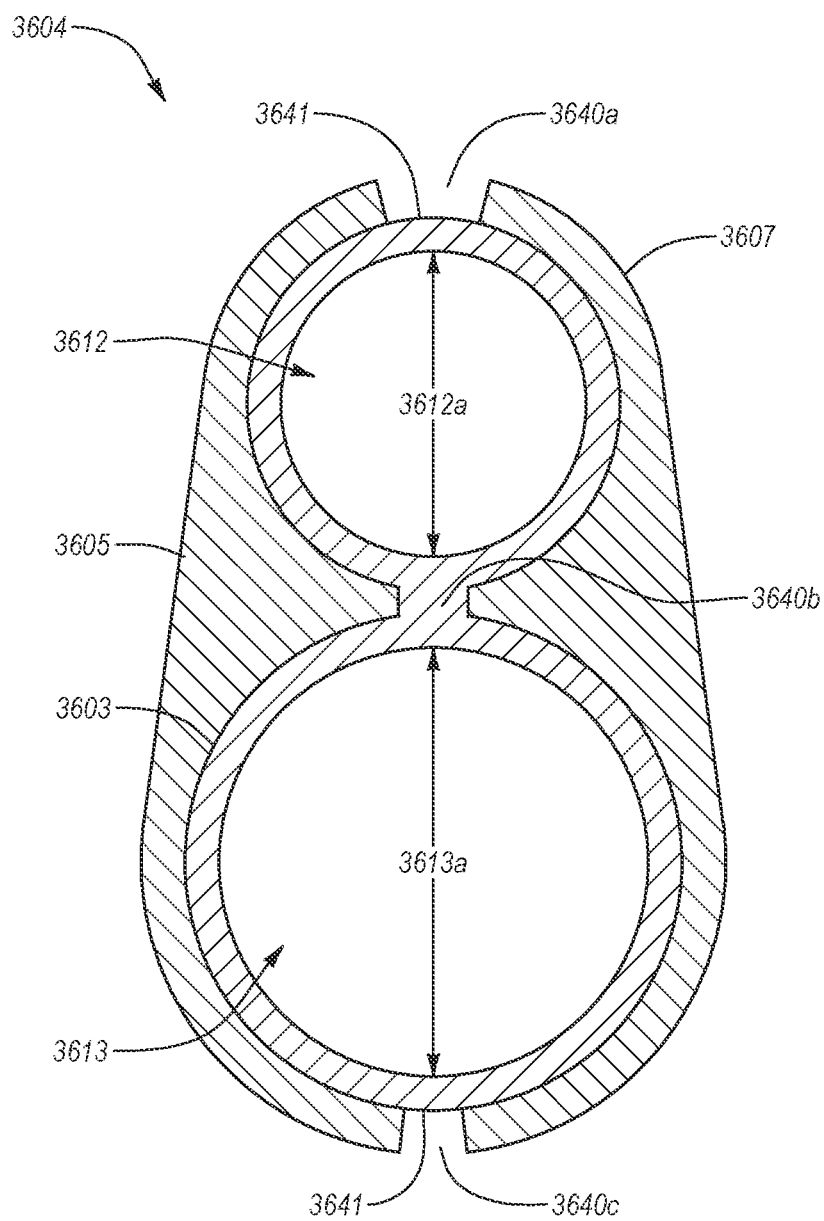
FIG. 33 illustrates a cross-sectional view of another embodiment of an introducer sheath in an unexpanded state.

FIG. 33 illustrates a cross-sectional view of another embodiment of an elongate or tubular portion 3604 of an introducer sheath in an unexpanded state. The tubular portion 3604 of the embodiment described herein and shown in FIG. 33 may be functionally similar to the introducer sheaths and/or tubular portions described herein in most respects, wherein certain features may not be described in relation to this embodiment wherein those components may function in the manner as described above and are hereby incorporated into this embodiment described below. Like structures and/or components are given like reference numerals. For example, the tubular portion 3604 may be used with the introducer sheath 3400 to include a hub portion 3402.

The tubular portion 3604 may extend between a proximal end (such as proximal end 3418 shown in FIG. 30) and a distal end (such as distal end 3420 shown in FIG. 30). The tubular portion 3604 may include an inner portion 3603 and an outer portion 3605. The inner portion 3603 and/or the outer portion 3605 may extend between the proximal end (such as proximal end 3418 shown in FIG. 30) and the distal end (such as distal end 3420 shown in FIG. 30) of the tubular portion 3604.

In the present embodiment, the inner portion 3603 may form at least two lumens 3612, 3613. The lumens 3612, 3613 may include an entry portion, such as entry portion 2228 shown in FIG. 18. The outer portion 3605 may be disposed partially around the inner portion 3603. For example, at least a portion of the inner portion 3603 may be exposed between the proximal end and the distal end of the tubular portion 3604. In embodiments such as the present embodiment, multiple portions of the inner portion 3603 may be exposed.

The tubular portion 3604 may include at least one aperture 3640*a*. In the presently illustrated embodiment, the tubular portion 3604 may include a first aperture 3640*a*, a second aperture 3640*b*, and a third aperture 3640*c*. The apertures 3640*a*, 3640*b*, 3640*c* may expose at least a portion of the inner portion 3603 between the proximal end (shown as 3418 in FIG. 30) and the distal end (shown as 3420 in FIG. 30) of the tubular portion 3604.

For example, the first aperture 3640*a* may expose a portion of the inner portion 3603 shown above the first lumen 3612, the second aperture 3640*b* may expose a portion of the inner portion 3603 shown between the first lumen 3612 and the second lumen 3613, the third aperture 3640*c* may expose a portion of the inner portion 3603 shown below the second lumen 3613, or combinations thereof. In other embodiments, more or fewer portions of the inner portion 3603 may be exposed. In the present embodiment, at least one of the apertures 3640*a*, 3640*b*, 3640*c* may extend from the proximal end to the distal end. In other embodiments, the apertures 3640*a*, 3640*b*, 3640*c* may extend between but not including both the proximal end and the distal end. The apertures 3640*a*, 3640*c* may extend from an outer surface 3607 of the outer portion 3605 to an outer surface 3641 of the inner portion 3603.

The lumens 3612, 3613 are shown in FIG. 33 in an unexpanded state. The lumens 3612, 3613 may include first inner dimensions 3612*a*, 3613*a*, respectively. The first inner dimensions 3612*a*, 3613*a* may include a diameter, a cross-sectional area, a radius, an arc length, other dimensions, or combinations thereof. For example, the first inner dimension 3613a of the second lumen 3613 may be a diameter of about six French in an unexpanded state.

The inner portion 3603 may include a first material that may include at least one relatively expandable material. The first material may provide lubricious properties to facilitate medical devices being inserted and/or removed through the lumen 3612. For example, the first material may include ePTFE, which may provide both expandability and lubricity.

The outer portion 3605 may include a second material that may provide expandability and/or lubricity. For example, the second material may include an elastomeric material. In the present embodiment, the second material may be less expandable (i.e. may have a lower modulus of elasticity) than the first material of the inner portion 3603. In embodiments where the second material may be less expandable than the first material and despite the reduced expandability of the second material, the exposure of the inner portion 3603 through at least a portion of the outer portion 3605 may facilitate expansion of the inner portion 3603. A less expandable second material may increase the longitudinal strength (i.e. resistance to buckling in the longitudinal direction) and/or pushability of the introducer sheath while providing radial expandability of the introducer sheath through the more expandable first material.

The tubular portion 3604, the inner portion 3603, the outer portion 3605, the first lumen 3612, the second lumen 3613, the first aperture 3640a, the second aperture 3640b, the third aperture 3640c, other components of the introducer sheath (such as introducer sheath 3400 shown in FIG. 30), or combinations thereof, may increase in at least one dimension in the expanded state. The inner portion 3603 and the outer portion 3605 may expand in conjunction with the first lumen 3612 and/or the second lumen 3613. The apertures 3640a, 3640b, 3640c may expand circumferentially. Expansion of the apertures 3640a, 3640b, 3640c may increase the size of at least one of the exposed portions of the inner portion 3603 of the tubular portion 3604. The outer portion 3605 may be disposed around less of the inner portion 3603 in the expanded state.

The lumens 3612, 3613 may include second inner dimensions (not shown) in an expanded state. The second inner dimensions may include a diameter, a cross-sectional area, a radius, an arc length, other dimensions, or combinations thereof. For example, the second inner dimension of the second lumen 3613 may include a diameter of about ten French. The second lumen 3613 may expand from the first inner dimension 3613a to a second inner dimension (not shown) of the second lumen 3613. This expansion may be about sixty-five percent. For example, from about six French to about ten French. In other embodiments, the expansion may be more and/or less than about sixty-five percent. For example, it may be as little as about ten percent. The first inner dimension 3612a of the first lumen 3612 may expand in similar fashion.

The inner portion 3603 and/or the outer portion 3605 may be arranged to facilitate entry and/or exit of a medical device through the lumens 3612, 3613 by expanding to accommodate the medical device without creating further apertures (not shown) in the outer surface (not shown) of the tubular portion 3604.

Figure 34:
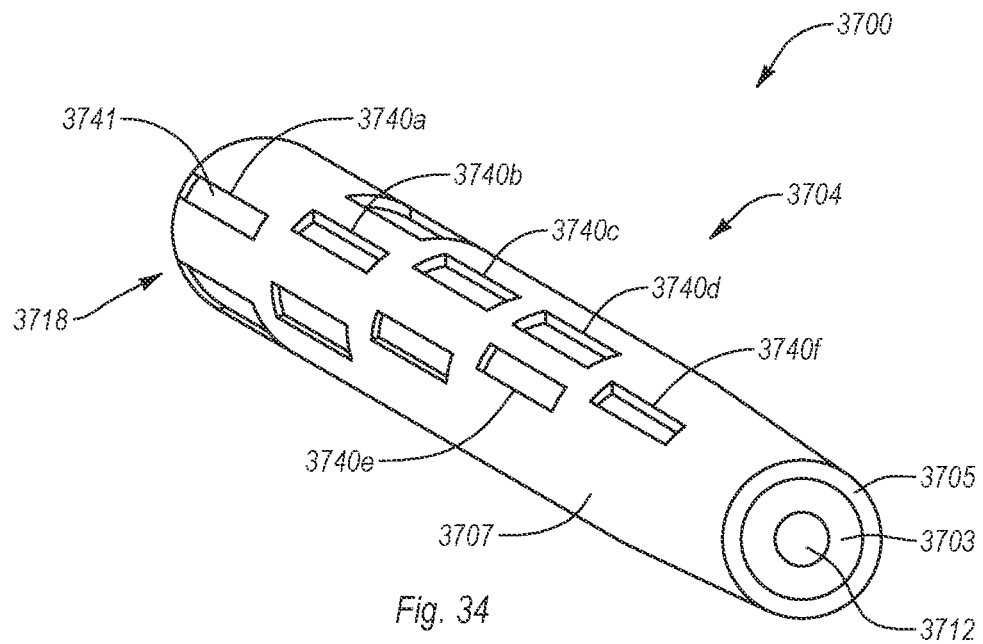
FIG. 34 illustrates a perspective view of a further embodiment of an introducer sheath.

FIG. 34 illustrates a perspective view of a further embodiment of an introducer sheath 3700. The introducer sheath 3700 of the embodiment described herein and shown in FIG. 33 may be functionally similar to the introducer sheaths and/or tubular portions described herein in most respects, wherein certain features may not be described in relation to this embodiment wherein those components may function in the manner as described above and are hereby incorporated into this embodiment described below. Like structures and/or components are given like reference numerals.

The elongate or tubular portion 3704 may extend between a proximal end 3718 and a distal end 3720. The tubular portion 3704 may include an inner portion 3703 and an outer portion 3705. The inner portion 3703 and/or the outer portion 3705 may extend between the proximal end 3718 and the distal end 3720 of the tubular portion 3704.

In the present embodiment, the inner portion 3703 may form a lumen 3712. In other embodiments, the inner portion 3703 may form a plurality of lumens. The lumen 3712 may include an entry portion, such as entry portion 2228 shown in FIG. 18. The outer portion 3705 may be disposed partially around the inner portion 3703. For example, at least a portion of the inner portion 3703 may be exposed between the proximal end and the distal end of the tubular portion 3704. In the present embodiment, multiple portions of the inner portion 3703 may be exposed.

The tubular portion 3704 may include at least one aperture. In the present embodiment, the tubular portion 3704 may include a first aperture 3740a, a second aperture 3740b, a third aperture 3740c, a fourth aperture 3740d, a fifth aperture 3740e, and a sixth aperture 3740f. The apertures 3740a, 3740b, 3740c, 3740d, 3740e, 3740f may expose at least a portion of the inner portion 3703 between the proximal end 3718 and the distal end 3720 of the tubular portion 3704.

The apertures 3740a, 3740b, 3740c, 3740d, 3740e, 3740f may expose various portions of the inner portion 3703. The apertures 3740a, 3740b, 3740c, 3740d, 3740e, 3740f may be longitudinally and/or axially oriented with respect to the lumen 3712 and/or circumferentially oriented with respect to the proximal end 3718 and/or the distal end 3720 of the tubular portion 3704.

For example and as shown in FIG. 34, the first aperture 3740a may expose a portion of the inner portion 3703 from the proximal end 3718 toward the distal end 3720, the second aperture 3740b may expose a portion of the inner portion 3703 longitudinally and circumferentially offset from the first aperture 3740a, the third aperture 3740c may expose a portion of the inner portion 3703 longitudinally and circumferentially offset from the first aperture 3740 and the second aperture 3740b, the fourth aperture 3740d may expose a portion of the inner portion 3703 longitudinally but not circumferentially offset from the third aperture 3740c, the fifth aperture 3740e may expose a portion of the inner portion 3703 longitudinally and circumferentially offset from the third aperture 3740c and circumferentially but not longitudinally offset from the fourth aperture 3740d, and the sixth aperture 3740f may expose a portion of the inner portion 3703 longitudinally but not circumferentially offset from the second aperture 3740b with a larger longitudinal offset from the second aperture 3740b than the third aperture 3740c though still longitudinally offset from the distal end 3720, such that nearly the entire length of the tubular portion 3704 may be exposed from the proximal end 3718 to the distal end 3720. In other embodiments, more or fewer portions of the inner portion 3703 may be exposed using more or fewer apertures in varying longitudinal and/or circumferential offsets and/or axial orientations with respect to the proximal end 3718, the distal end 3720, other apertures, or combinations thereof. In the present embodiment, none of the apertures 3740a, 3740b, 3740c, 3740d, 3740e, 3740f extend from the proximal end 3718 to the distal end 3720. In other embodiments, at least one of the apertures 3740a, 3740b, 3740c, 3740d, 3740e, 3740f may extend from the proximal end to the distal end. The apertures 3740a, 3740b, 3740c, 3740d, 3740e, 3740f may extend from an outer surface 3707 of the outer portion 3705 to an outer surface 3741 of the inner portion 3703.

The inner portion 3703 may include a first material that may include at least one relatively expandable material. The first material may provide lubricious properties to facilitate medical devices being inserted and/or removed through the lumen 3712. For example, the first material may include ePTFE, which may provide both expandability and lubricity.

The outer portion 3705 may include a second material that may provide expandability and/or lubricity. For example, the second material may include an elastomeric material. In the present embodiment, the second material may be less expandable (i.e. may have a lower modulus of elasticity) than the first material of the inner portion 3703. In embodiments where the second material may be less expandable than the first material and despite the reduced expandability of the second material, the exposure of the inner portion 3703 through at least a portion of the outer portion 3705 may facilitate expansion of the inner portion 3703. A less expandable second material may increase the longitudinal strength (i.e. resistance to buckling in the longitudinal direction) and/or pushability of the introducer sheath while providing radial expandability of the introducer sheath through the more expandable first material.

The inner portion 3703 and/or the outer portion 3705 may be arranged to facilitate entry and/or exit of a medical device through the lumen 3712 by expanding to accommodate the medical device without creating further apertures (not shown) in the outer surface (not shown) of the tubular portion 3704.

Figure 35:
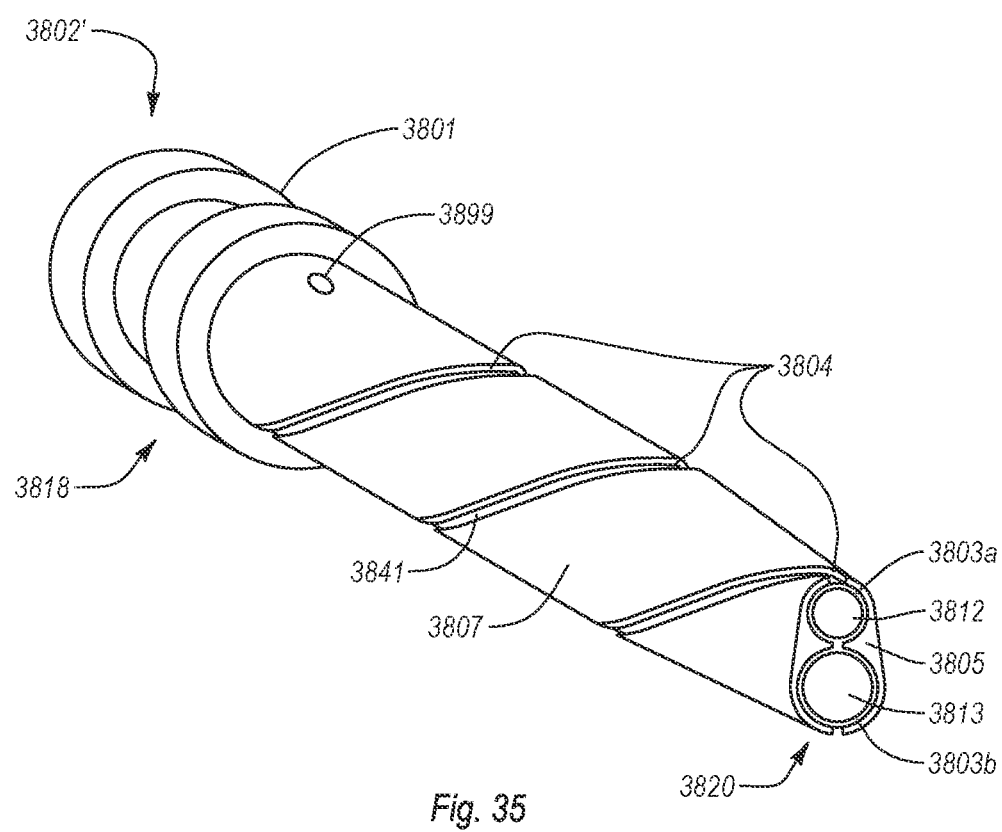
FIG. 35 illustrates a perspective view of yet another embodiment of an introducer sheath.

FIG. 35 illustrates a perspective view of yet another embodiment of an introducer sheath. The introducer sheath 3800 of the embodiment described herein and shown in FIG. 35 may be functionally similar to the introducer sheaths and/or tubular portions described herein in most respects, wherein certain features may not be described in relation to this embodiment wherein those components may function in the manner as described above and are hereby incorporated into this embodiment described below. Like structures and/or components are given like reference numerals.

The introducer sheath 3800 may include a hub portion 3802. The hub portion 3802 may include a flange 3801. The hub portion 3802 and/or the flange 3801 May configured to selectively connect to a medical device (not shown) to limit longitudinal and/or axial motion of the introducer sheath 3800 with respect to the medical device.

The elongate or tubular portion 3804 may extend between a proximal end 3818 and a distal end 3820. The tubular portion 3804 may include at least one inner portion 3803a, 3803b and an outer portion 3805. The inner portions 3803a, 3803b and/or the outer portion 3805 may extend between the proximal end 3818 and the distal end 3820 of the tubular portion 3804.

In the present embodiment, the inner portion 1003 may form at least two lumens 3812, 3813. In other embodiments, the inner portions 3803a, 3803b may form more or fewer lumens. The outer portion 3805 may be disposed at least partially around the inner portions 3803a, 3803b. For example, at least a portion of at least one inner portion 3803a, 3803b may be exposed between the proximal end and the distal end of the tubular portion 3804. In other embodiments, multiple portions of the more or fewer inner portions may be exposed. For example, in some embodiments, it may be desirable for a lumen, such as lumen 3812 to be less expandable than another lumen, such as lumen 3813 such that no portion or fewer portions of the inner portion, such as inner portion 3803a, may be exposed.

The tubular portion 3804 may include an aperture 3840. The aperture 3840 may be longitudinally and/or axially oriented with respect to the lumen 1012 and/or circumferentially oriented with respect to the proximal end 3818 and/or the distal end 3820 of the tubular portion 3804. In the present embodiment, the aperture 3840 may expose a portion of the inner portions 3803a, 3803b from the proximal end 3818 to the distal end 3820 in a generally helical manner. The axial orientation (i.e. pitch) of the aperture 3840 may be constant and/or vary along the length of the tubular portion 3804.

In other embodiments, more or fewer portions of the inner portions 3803a, 3803b may be exposed using more or fewer apertures in varying longitudinal and/or circumferential offsets and/or axial orientations with respect to the proximal end 3818, the distal end 3820, other apertures, or combinations thereof. In the present embodiment, the aperture 3840 extends from the proximal end 3818 to the distal end 3820. The aperture 3840 may extend from an outer surface (not shown) of the outer portion 3805 to an outer surface (not shown) of the inner portions 3803a, 3803b.

The inner portions 3803a, 3803b may include a first material. The first material may include at least one relatively expandable material. The first material may provide lubricious properties to facilitate medical devices being inserted and/or removed through the lumen 3812. For example, the first material may include ePTFE, which may provide both expandability and lubricity. The present embodiment, the inner portions 3803a, 3803b may include the same first material. In other embodiments, the inner portions 3803a, 3803b may include different materials.

The outer portion 3805 may include a second material. The second material may provide expandability and/or lubricity. For example, the second material may include an elastomeric material. In the present embodiment, the second material may be less expandable (i.e. may have a lower modulus of elasticity) than the first material of the inner portions 3803a, 3803b. In embodiments where the second material may be less expandable than the first material and despite the reduced expandability of the second material, the exposure of the inner portions 3803a, 3803b through at least a portion of the outer portion 3805 may facilitate expansion of the inner portions 3803a, 3803b. A less expandable second material may increase the longitudinal strength (i.e. resistance to buckling in the longitudinal direction) and/or pushability of the introducer sheath while providing radial expandability of the introducer sheath through the more expandable first material.

The first inner portion 3803a, the second inner portion 3803b, the outer portion 3805, or combinations thereof may be arranged to facilitate entry and/or exit of a medical device through the lumen 3812 by expanding to accommodate the medical device without creating further apertures (not shown) in the outer surface (not shown) of the tubular portion 3804.

The various introducer sheaths described herein that include an inner portion and an outer portion may be manufactured by forming the inner portion and forming the outer portion around the inner portion such that the outer portion encloses less than the entirety of the outer surface of the inner portion between the proximal end and a distal end. The tubular portion and/or hub portion of an introducer sheath may be manufactured using various processes. For example, the tubular portion and/or hub portion of an introducer sheath may be manufactured using an injection molding process, an overmolding process, an extrusion process, a coextrusion process, a bump extrusion process, other processes, or combinations thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device comprising:
    a hub portion with a port, a tapered distal end, and a hub lumen extending from the port to the tapered distal end; and
    an elongate member extending from the hub portion, the elongate member comprising:
        a plurality of elastic portions; and
        a plurality of sheath portions that are stiffer than the plurality of elastic portions, the plurality of elastic portions and the plurality of sheath portions being disposed in alternating fashion circumferentially around the elongate member,
        wherein, the plurality of elastic portions and the plurality of sheath portions extend into the tapered distal end of the hub portion.

2. The medical device of claim 1, wherein the plurality of elastic portions are elastic strips extending from a distal end to towards a proximal end of the elongate member.

3. The medical device of claim 1, wherein the plurality of elastic portions is configured to reduce in thickness upon expansion of the elongate member.

4. The medical device of claim 1, wherein a sheath portion of the plurality of sheath portions comprises a radially extending surface, a circumferentially extending surface, and an inner circumferentially extending surface forming at least a portion of a lumen of the elongate member.

5. The medical device of claim 4, wherein an elastic portion of the plurality of elastic portions overlaps the radially extending surface and the circumferentially extending surface.

6. The medical device of claim 4, wherein an elastic portion of the plurality of elastic portions forms an outer surface of the elongate member.

7. The medical device of claim 1, wherein each of the plurality of elastic portions has a uniform thickness.

8. The medical device of claim 1, wherein each of the plurality of elastic portions is configured to stretch elastically along an arc that curves from a first surface of a wall of the elongate member to a second surface of the wall.

9. A method comprising: deploying a first medical device into a body lumen, the first medical device comprising: a device receiving hub portion with a port, a tapered distal end, a hub lumen extending from the port to the tapered distal end, and a valve; and an elongate member extending from the hub portion and forming a lumen extending to a distal end of the elongate member, the elongate member comprising: a plurality of elastic portions forming a surface of the lumen, wherein deformation of the plurality of elastic portions changes a shape of the surface of the lumen and an outer surface of the elongate member; and a plurality of sheath portions that are stiffer than the plurality of elastic portions, the plurality of elastic portions and the plurality of sheath portions being disposed in alternating fashion circumferentially around the elongate member, wherein the plurality of elastic portions and the plurality of sheath portions extend into the tapered distal end of the hub portion; and deploying a second medical device through the hub and the lumen of the elongate member.

10. The method as recited in claim 9, wherein deploying the second medical device further comprises expanding the lumen from a first diameter to a second diameter.

11. The method as recited in claim 9, wherein the second medical device comprises an expandable balloon.

12. The method as recited in claim 9, wherein a sheath portion of the plurality of sheath portions comprises a radially extending surface, a circumferentially extending surface, and an inner circumferentially extending surface forming at least a portion of a lumen of the elongate member.

13. The method as recited in claim 9, wherein an elastic portion of the plurality of elastic portions overlaps the radially extending surface and the circumferentially extending surface.

14. The method as recited in claim 9, wherein an elastic portion of the plurality of elastic portions forms an outer surface of the elongate member.

* * * * *